US010758623B2

(12) United States Patent
Sekar et al.

(10) Patent No.: US 10,758,623 B2
(45) Date of Patent: Sep. 1, 2020

(54) PHARMACEUTICALLY ACTIVE AGENT COMPLEXES, POLYMER COMPLEXES, AND COMPOSITIONS AND METHODS INVOLVING THE SAME

(71) Applicant: Durect Corporation, Cupertino, CA (US)

(72) Inventors: Michael Sekar, Palo Alto, CA (US); Felix Theeuwes, Los Altos Hills, CA (US); Keith E Branham, Pelham, AL (US); John Gibson, Springville, AL (US); James Matriano, Mountain View, CA (US); Whitney Moro, Birmingham, AL (US); John Tipton, Leeds, AL (US); William Van Osdol, Mountain View, CA (US); Su Il Yum, Los Altos, CA (US)

(73) Assignee: DURECT CORPORATION, Cupertino, CA (US)

( * ) Notice: Subject to any disclaimer, the term of this patent is extended or adjusted under 35 U.S.C. 154(b) by 86 days.

(21) Appl. No.: 15/887,916

(22) Filed: Feb. 2, 2018

(65) Prior Publication Data
US 2018/0256727 A1  Sep. 13, 2018

Related U.S. Application Data

(63) Continuation of application No. 15/102,519, filed as application No. PCT/US2014/069156 on Dec. 8, 2014, now abandoned.

(60) Provisional application No. 61/913,827, filed on Dec. 9, 2013.

(51) Int. Cl.
| | |
|---|---|
| *A61K 31/352* | (2006.01) |
| *A61K 31/706* | (2006.01) |
| *A61K 31/785* | (2006.01) |
| *A61K 38/26* | (2006.01) |
| *A61K 38/27* | (2006.01) |
| *A61K 47/54* | (2017.01) |
| *A61K 9/16* | (2006.01) |
| *A61K 9/19* | (2006.01) |
| *A61K 9/00* | (2006.01) |
| *A61K 47/59* | (2017.01) |
| *A61K 38/28* | (2006.01) |
| *A61K 38/31* | (2006.01) |
| *A61K 39/395* | (2006.01) |

(52) U.S. Cl.
CPC ............ *A61K 47/54* (2017.08); *A61K 9/0019* (2013.01); *A61K 9/1647* (2013.01); *A61K 9/19* (2013.01); *A61K 31/352* (2013.01); *A61K 31/706* (2013.01); *A61K 31/785* (2013.01); *A61K 38/26* (2013.01); *A61K 38/27* (2013.01); *A61K 38/28* (2013.01); *A61K 38/31* (2013.01); *A61K 39/39516* (2013.01); *A61K 47/593* (2017.08)

(58) Field of Classification Search
CPC .... A61K 47/54; A61K 47/593; A61K 9/0019; A61K 9/1647; A61K 31/352; A61K 31/706; A61K 31/785; A61K 38/26; A61K 38/27; A61K 38/28; A61K 38/31
See application file for complete search history.

(56) References Cited

U.S. PATENT DOCUMENTS

| | | | |
|---|---|---|---|
| 3,797,492 A | 3/1974 | Place | |
| 3,868,358 A | 2/1975 | Jackson | |
| 3,923,939 A | 12/1975 | Baker et al. | |
| 3,987,790 A | 10/1976 | Eckenhoff et al. | |
| 4,008,719 A | 2/1977 | Theeuwes et al. | |
| 4,257,938 A | 3/1981 | Hosoi et al. | |
| 4,374,932 A | 2/1983 | Pitzele et al. | |
| 4,443,340 A | 4/1984 | May et al. | |
| 4,586,559 A | 2/1986 | Nuwayser et al. | |
| 4,623,588 A | 11/1986 | Nuwayser et al. | |
| 4,668,506 A | 5/1987 | Bawa | |
| 4,708,861 A | 11/1987 | Popescu et al. | |
| 4,711,782 A | 12/1987 | Okada et al. | |
| 4,713,244 A | 12/1987 | Bawa et al. | |
| 4,784,845 A | 11/1988 | Desai et al. | |
| 4,789,516 A | 12/1988 | Lim | |
| 4,806,345 A | 1/1989 | Bhattacharyya | |
| 4,808,411 A | 2/1989 | Lu et al. | |
| 4,816,568 A | 3/1989 | Hamilton, Jr. et al. | |
| 4,834,965 A | 5/1989 | Martani et al. | |

(Continued)

FOREIGN PATENT DOCUMENTS

| | | |
|---|---|---|
| EP | 0216485 | 1/1987 |
| EP | 0402070 | 12/1990 |

(Continued)

OTHER PUBLICATIONS

Lele et al. (J. Biomater. Sci. Edn., vol. 11, No. 12, pp. 1319-1331, published in 2000) (Year: 2000).*

(Continued)

*Primary Examiner* — Alma Pipic

(57) ABSTRACT

The present disclosure generally provides complexes including a pharmaceutically active agent and a functionalized polymer, wherein the functionalized polymer includes repeat units, the repeat units including ionizable repeat units having at least one ionizable side group and/or ionizable end group, a plurality of the at least one ionizable groups forming non-covalent bonds with the pharmaceutically active agent. Polymers which may be used to form such complexes as well as methods of making and using the complexes and related compositions are also provided.

16 Claims, 22 Drawing Sheets

(56) References Cited

U.S. PATENT DOCUMENTS

| | | |
|---|---|---|
| 4,853,218 A | 8/1989 | Yim et al. |
| 4,865,845 A | 9/1989 | Echenhoff et al. |
| 4,866,050 A | 9/1989 | Ben-Amoz |
| 4,871,538 A | 10/1989 | Yim et al. |
| 4,931,279 A | 6/1990 | Bawa et al. |
| 4,938,763 A | 7/1990 | Dunn et al. |
| 4,985,404 A | 1/1991 | Mitchell et al. |
| 5,019,400 A | 5/1991 | Gombols et al. |
| 5,057,318 A | 10/1991 | Magruder et al. |
| 5,059,423 A | 10/1991 | Magruder et al. |
| 5,061,492 A | 10/1991 | Okada et al. |
| 5,077,033 A | 12/1991 | Viegas et al. |
| 5,085,866 A | 2/1992 | Cowsar et al. |
| 5,112,614 A | 5/1992 | Magruder et al. |
| 5,137,727 A | 8/1992 | Eckenhoff et al. |
| 5,151,093 A | 9/1992 | Theeuwes et al. |
| 5,181,914 A | 1/1993 | Zook |
| 5,209,746 A | 5/1993 | Balaban et al. |
| 5,229,130 A | 7/1993 | Sharma et al. |
| 5,234,692 A | 8/1993 | Magruder et al. |
| 5,234,693 A | 8/1993 | Magruder et al. |
| 5,242,910 A | 9/1993 | Damanj |
| 5,244,655 A | 9/1993 | Viscomi et al. |
| 5,252,318 A | 10/1993 | Joshi et al. |
| 5,278,201 A | 1/1994 | Dunn et al. |
| 5,279,608 A | 1/1994 | Cheikh |
| 5,300,295 A | 4/1994 | Viegas et al. |
| 5,308,348 A | 5/1994 | Balaban et al. |
| 5,310,865 A | 5/1994 | Enomoto et al. |
| 5,324,519 A | 6/1994 | Dunn et al. |
| 5,330,452 A | 7/1994 | Zook |
| 5,336,057 A | 8/1994 | Fukida et al. |
| 5,340,614 A | 8/1994 | Perman et al. |
| 5,342,627 A | 8/1994 | Chopra et al. |
| 5,415,866 A | 5/1995 | Zook |
| 5,441,732 A | 8/1995 | Hoag et al. |
| 5,441,734 A | 8/1995 | Reichert et al. |
| 5,447,725 A | 9/1995 | Damani et al. |
| 5,456,679 A | 10/1995 | Balaban et al. |
| 5,461,031 A | 10/1995 | De Felippis |
| 5,487,897 A | 1/1996 | Polson et al. |
| 5,540,912 A | 7/1996 | Roorda et al. |
| 5,543,156 A | 8/1996 | Roorda et al. |
| 5,556,905 A | 9/1996 | Frappier et al. |
| 5,567,677 A | 10/1996 | Castensson et al. |
| 5,571,525 A | 11/1996 | Roorda et al. |
| 5,599,534 A | 2/1997 | Himmelstein et al. |
| 5,599,552 A | 2/1997 | Dunn et al. |
| 5,602,232 A | 2/1997 | Reichert et al. |
| 5,610,184 A | 3/1997 | Shahinian, Jr. |
| 5,618,563 A | 4/1997 | Berde et al. |
| 5,620,700 A | 4/1997 | Berggen et al. |
| 5,641,656 A | 6/1997 | Skellick et al. |
| 5,651,986 A | 7/1997 | Brem et al. |
| 5,653,992 A | 8/1997 | Bezwada et al. |
| 5,654,010 A | 8/1997 | Johnson et al. |
| 5,656,297 A | 8/1997 | Bernstein et al. |
| 5,660,817 A | 8/1997 | Masterman et al. |
| 5,667,808 A | 9/1997 | Johnson et al. |
| 5,674,292 A | 10/1997 | Tucker et al. |
| 5,681,873 A | 10/1997 | Norton et al. |
| 5,700,485 A | 12/1997 | Berde et al. |
| 5,707,664 A | 1/1998 | Mak |
| 5,708,011 A | 1/1998 | Bardsley et al. |
| 5,709,837 A | 1/1998 | Mori et al. |
| 5,716,981 A | 2/1998 | Hunter et al. |
| 5,721,206 A | 2/1998 | Tobe et al. |
| 5,733,950 A | 3/1998 | Dunn et al. |
| 5,744,153 A | 4/1998 | Yewey et al. |
| 5,744,166 A | 4/1998 | Illum |
| 5,747,058 A | 5/1998 | Tipton et al. |
| 5,747,060 A | 5/1998 | Sackler et al. |
| 5,759,563 A | 6/1998 | Yewey et al. |
| 5,760,077 A | 6/1998 | Shahinian, Jr. |
| 5,766,637 A | 6/1998 | Shine et al. |
| 5,770,217 A | 6/1998 | Kutilek, III et al. |
| 5,780,044 A | 7/1998 | Yewey et al. |
| 5,783,205 A | 7/1998 | Berggren et al. |
| 5,787,175 A | 7/1998 | Carter |
| 5,804,212 A | 9/1998 | Blum |
| 5,821,206 A | 10/1998 | Payne et al. |
| 5,846,763 A | 12/1998 | Lee et al. |
| 5,849,763 A | 12/1998 | Bardsley et al. |
| 5,885,567 A | 3/1999 | Sekellick et al. |
| 5,889,110 A | 3/1999 | Hutchinson |
| 5,891,478 A | 4/1999 | Johnson et al. |
| 5,910,502 A | 6/1999 | Gennery |
| 5,919,835 A | 7/1999 | Domb et al. |
| 5,922,340 A | 7/1999 | Berde et al. |
| 5,935,599 A | 8/1999 | Dadey |
| 5,942,241 A | 8/1999 | Chasin et al. |
| 5,955,479 A | 9/1999 | Bardsley et al. |
| 5,958,443 A | 9/1999 | Viegas et al. |
| 5,968,542 A | 10/1999 | Tipton et al. |
| 5,972,326 A | 10/1999 | Galin et al. |
| 5,972,366 A | 10/1999 | Haynes et al. |
| 5,977,308 A | 11/1999 | Cousens et al. |
| 5,985,305 A | 11/1999 | Peery et al. |
| 5,985,309 A | 11/1999 | Edwards |
| 5,990,194 A | 11/1999 | Dunn et al. |
| 6,004,295 A | 12/1999 | Langer et al. |
| 6,004,549 A | 12/1999 | Reichert et al. |
| 6,020,465 A | 2/2000 | Sekellick et al. |
| 6,045,794 A | 4/2000 | Cousens et al. |
| 6,046,187 A | 4/2000 | Berde et al. |
| 6,050,986 A | 4/2000 | Hektner |
| 6,051,259 A | 4/2000 | Johnson et al. |
| 6,063,370 A | 5/2000 | Dadey |
| 6,086,909 A | 7/2000 | Harrison et al. |
| 6,096,335 A | 8/2000 | Thierry |
| 6,102,205 A | 8/2000 | Greff et al. |
| 6,103,266 A | 8/2000 | Tapolski et al. |
| 6,106,301 A | 8/2000 | Merril |
| 6,113,938 A | 9/2000 | Chen et al. |
| 6,117,425 A | 9/2000 | McPhee et al. |
| 6,120,789 A | 9/2000 | Dunn |
| 6,120,804 A | 9/2000 | Drizen et al. |
| 6,129,933 A | 10/2000 | Oshlack et al. |
| 6,130,200 A | 10/2000 | Brodbeck et al. |
| 6,132,420 A | 10/2000 | Dionne et al. |
| 6,136,334 A | 10/2000 | Viegas et al. |
| 6,143,314 A | 11/2000 | Chandeashekar et al. |
| 6,156,331 A | 12/2000 | Peery et al. |
| 6,165,508 A | 12/2000 | Tracy et al. |
| 6,190,684 B1 | 2/2001 | Hench et al. |
| 6,193,991 B1 | 2/2001 | Shukla |
| 6,193,994 B1 | 2/2001 | Lee et al. |
| 6,197,327 B1 | 3/2001 | Harrison et al. |
| 6,210,717 B1 | 4/2001 | Choi et al. |
| 6,210,905 B1 | 4/2001 | Lee et al. |
| 6,214,387 B1 | 4/2001 | Berde et al. |
| 6,217,911 B1 | 4/2001 | Vaung et al. |
| 6,238,702 B1 | 5/2001 | Berde et al. |
| 6,248,345 B1 | 6/2001 | Goldenheim et al. |
| 6,255,502 B1 | 7/2001 | Penkler et al. |
| 6,258,995 B1 | 7/2001 | Gilding et al. |
| 6,261,547 B1 | 7/2001 | Bawa et al. |
| 6,280,742 B1 | 8/2001 | Seid et al. |
| 6,281,337 B1 | 8/2001 | Cannon-Carlson et al. |
| 6,309,375 B1 | 10/2001 | Glines et al. |
| 6,322,548 B1 | 11/2001 | Payne et al. |
| 6,331,309 B1 | 12/2001 | Jennings et al. |
| 6,331,311 B1 | 12/2001 | Brodbeck et al. |
| 6,335,383 B1 | 1/2002 | Scopelianos et al. |
| 6,352,667 B1 | 3/2002 | English |
| 6,355,273 B1 | 3/2002 | Carli et al. |
| 6,372,245 B1 | 4/2002 | Bowman et al. |
| 6,375,659 B1 | 4/2002 | Tracy et al. |
| 6,379,701 B1 | 4/2002 | Tracey et al. |
| 6,395,292 B2 | 5/2002 | Peery et al. |
| 6,395,293 B2 | 5/2002 | Polson et al. |
| 6,403,057 B1 | 6/2002 | Schneider et al. |
| 6,410,057 B1 | 6/2002 | Kweon-Choi |
| 6,413,536 B1 | 7/2002 | Gibson et al. |

(56) References Cited

U.S. PATENT DOCUMENTS

| | | |
|---|---|---|
| 6,417,201 B1 | 7/2002 | Bardsley et al. |
| 6,423,677 B1 | 7/2002 | Van Eenam |
| 6,423,818 B1 | 7/2002 | Matsuda et al. |
| 6,426,339 B1 | 7/2002 | Berde et al. |
| 6,432,415 B1 | 8/2002 | Osborne et al. |
| 6,432,438 B1 | 8/2002 | Shukla |
| 6,432,986 B2 | 8/2002 | Levin |
| 6,451,346 B1 | 9/2002 | Shah |
| 6,461,631 B1 | 10/2002 | Dunn et al. |
| 6,468,961 B1 | 10/2002 | Brodbeck et al. |
| RE37,950 E | 12/2002 | Dunn et al. |
| 6,500,448 B1 | 12/2002 | Johnson |
| 6,514,994 B2 | 2/2003 | Mather et al. |
| 6,528,080 B2 | 3/2003 | Dunn et al. |
| 6,528,086 B2 | 3/2003 | Zhang |
| 6,534,081 B2 | 3/2003 | Goldenheim et al. |
| 6,534,657 B2 | 3/2003 | Zhang |
| 6,566,345 B2 | 5/2003 | Miller et al. |
| 6,599,627 B2 | 7/2003 | Yeo et al. |
| 6,605,294 B2 | 8/2003 | Sawhney |
| 6,630,155 B1 | 10/2003 | Chandrashekar et al. |
| 6,645,525 B1 | 11/2003 | Woiszwillo |
| 6,664,234 B1 | 12/2003 | Heintz et al. |
| 6,669,958 B1 | 12/2003 | Trager |
| 6,673,767 B1 | 1/2004 | Brodbeck et al. |
| 6,703,477 B2 | 3/2004 | Pham |
| 6,733,788 B2 | 5/2004 | Mchride et al. |
| 6,823,084 B2 | 11/2004 | Zhang et al. |
| 6,825,343 B2 | 11/2004 | MacAlpine et al. |
| 6,899,731 B2 | 5/2005 | Li et al. |
| 6,939,538 B2 | 9/2005 | Prescott et al. |
| 6,989,138 B2 | 1/2006 | Cyr |
| 6,992,065 B2 | 1/2006 | Okumu |
| 7,138,105 B2 | 11/2006 | Bolotin |
| 7,160,931 B2 | 1/2007 | Cheng et al. |
| 7,163,701 B2 | 1/2007 | Cleland et al. |
| 7,205,378 B2 | 4/2007 | Ignatious |
| 7,258,869 B1 | 8/2007 | Berry et al. |
| 7,315,758 B2 | 1/2008 | Kwiatkowski et al. |
| 7,318,931 B2 | 1/2008 | Okumu |
| 7,319,004 B2 | 1/2008 | Harper et al. |
| 7,368,126 B2 | 5/2008 | Chen et al. |
| 7,456,147 B2 | 11/2008 | Kumar et al. |
| 7,491,537 B2 | 2/2009 | Fewell et al. |
| 7,682,630 B2 | 3/2010 | Maeda et al. |
| 7,687,054 B2 | 3/2010 | Stefely et al. |
| 7,709,655 B2 | 5/2010 | Zhang |
| 7,763,736 B2 | 7/2010 | Sharpless et al. |
| 7,772,182 B2 | 8/2010 | Liu et al. |
| 7,794,706 B2 | 9/2010 | Carpenter et al. |
| 7,794,836 B2 | 9/2010 | Vasishtha et al. |
| 7,795,031 B2 | 9/2010 | Demeneix et al. |
| 7,795,355 B2 | 9/2010 | Matyjaszewski et al. |
| 7,824,700 B2 | 11/2010 | Cleland et al. |
| 7,829,109 B2 | 11/2010 | Chen et al. |
| 7,829,659 B2 | 11/2010 | Grabstein et al. |
| 7,833,543 B2 | 11/2010 | Gibson et al. |
| 7,838,619 B2 | 11/2010 | Papisov |
| 7,964,219 B2 | 6/2011 | Li et al. |
| 7,985,424 B2 | 7/2011 | Tomalia et al. |
| 8,071,708 B2 | 12/2011 | Ritter et al. |
| 8,092,710 B2 | 1/2012 | Mohanty et al. |
| 8,128,952 B2 | 3/2012 | Metters et al. |
| 8,153,729 B2 | 4/2012 | Hawker et al. |
| 8,193,335 B2 | 6/2012 | Carell et al. |
| 8,206,735 B2 | 6/2012 | Li et al. |
| 8,207,174 B2 | 6/2012 | Tasler et al. |
| 8,236,353 B2 | 8/2012 | Checot et al. |
| 8,318,816 B2 | 11/2012 | Hoffman et al. |
| 8,318,856 B2 | 11/2012 | Oh et al. |
| 8,337,896 B2 | 12/2012 | Egashira |
| 8,343,710 B1 | 1/2013 | Anseth et al. |
| 8,344,116 B2 | 1/2013 | Kwon |
| 8,367,110 B2 | 2/2013 | Kohn et al. |
| 8,372,986 B2 | 2/2013 | Fokin et al. |
| 8,377,890 B2 | 2/2013 | Zur Wiesche et al. |
| 8,378,041 B2 | 2/2013 | Johnson et al. |
| 8,394,351 B2 | 3/2013 | Valdez et al. |
| 8,394,914 B2 | 3/2013 | Baker et al. |
| 8,399,024 B2 | 3/2013 | Kato et al. |
| 8,404,249 B2 | 3/2013 | Dake et al. |
| 8,420,802 B2 | 4/2013 | Jardine et al. |
| 8,425,892 B2 | 4/2013 | Bologna et al. |
| 8,425,900 B2 | 4/2013 | Yang et al. |
| 8,809,466 B2 | 8/2014 | Tang et al. |
| 9,080,144 B2 | 7/2015 | Yousaf |
| 9,572,857 B2 | 2/2017 | Li et al. |
| 9,737,605 B2 | 8/2017 | Wright et al. |
| 10,226,532 B2 | 3/2019 | Wright |
| 2001/0004644 A1 | 6/2001 | Levin |
| 2002/0001608 A1 | 1/2002 | Polson et al. |
| 2002/0010150 A1 | 1/2002 | Cortese et al. |
| 2002/0019336 A1 | 2/2002 | Kitagawa et al. |
| 2002/0028243 A1 | 3/2002 | Masters |
| 2002/0037358 A1 | 3/2002 | Barry et al. |
| 2002/0039594 A1 | 4/2002 | Unger et al. |
| 2002/0045668 A1 | 4/2002 | Dang et al. |
| 2002/0082237 A1 | 6/2002 | Sullivan et al. |
| 2002/0146829 A1 | 10/2002 | Hofland et al. |
| 2002/0173552 A1 | 11/2002 | Cleland |
| 2002/0176841 A1 | 11/2002 | Barker et al. |
| 2003/0021778 A1 | 1/2003 | Simon |
| 2003/0068277 A1 | 4/2003 | Vanbever et al. |
| 2003/0134811 A1 | 7/2003 | Jackson et al. |
| 2003/0170289 A1 | 9/2003 | Chen et al. |
| 2003/0180287 A1 | 9/2003 | Gombotz et al. |
| 2003/0211974 A1 | 11/2003 | Brodbeck et al. |
| 2003/0232824 A1 | 12/2003 | Schmees et al. |
| 2004/0001889 A1 | 1/2004 | Chen et al. |
| 2004/0013731 A1 | 1/2004 | Chen et al. |
| 2004/0022859 A1 | 2/2004 | Chen et al. |
| 2004/0024069 A1 | 2/2004 | Chen et al. |
| 2004/0057996 A1 | 3/2004 | Takada et al. |
| 2004/0076614 A1 | 4/2004 | Schur |
| 2004/0086481 A1 | 5/2004 | Garnett et al. |
| 2004/0136961 A1 | 7/2004 | Prokop et al. |
| 2004/0230183 A1 | 11/2004 | Breegi et al. |
| 2004/0241229 A1 | 12/2004 | Yamamoto et al. |
| 2004/0241239 A1 | 12/2004 | Bastian |
| 2004/0247561 A1 | 12/2004 | Seo et al. |
| 2004/0247672 A1 | 12/2004 | Tracy et al. |
| 2005/0008620 A1 | 1/2005 | Shimp et al. |
| 2005/0025717 A1 | 2/2005 | Dugger, III |
| 2005/0079202 A1 | 4/2005 | Chen et al. |
| 2005/0118718 A1 | 6/2005 | Bae et al. |
| 2005/0147581 A1 | 7/2005 | Zamiri et al. |
| 2005/0196559 A1 | 9/2005 | Nishio et al. |
| 2005/0266087 A1 | 12/2005 | Junnarkar et al. |
| 2005/0287057 A1 | 12/2005 | Richards |
| 2006/0013879 A9 | 1/2006 | Brodbeck et al. |
| 2006/0074019 A1 | 4/2006 | Bright et al. |
| 2006/0120973 A1 | 6/2006 | Dyer |
| 2006/0121121 A1 | 6/2006 | Jin et al. |
| 2006/0141046 A1 | 6/2006 | Cattaneo |
| 2006/0142234 A1 | 6/2006 | Chen et al. |
| 2006/0165800 A1 | 7/2006 | Chen et al. |
| 2006/0193825 A1 | 8/2006 | Musso et al. |
| 2006/0198873 A1 | 9/2006 | Chan et al. |
| 2006/0204533 A1 | 9/2006 | Hsu et al. |
| 2006/0233841 A1 | 10/2006 | Brodbeck et al. |
| 2006/0251618 A1 | 11/2006 | Dennis |
| 2006/0275251 A1 | 12/2006 | Santar et al. |
| 2006/0293217 A1 | 12/2006 | Barker et al. |
| 2007/0015689 A1 | 1/2007 | Rohloff et al. |
| 2007/0037891 A1 | 2/2007 | Esfand et al. |
| 2007/0059277 A1 | 3/2007 | Bhagat et al. |
| 2007/0086975 A1 | 4/2007 | Ignatious et al. |
| 2007/0134332 A1 | 6/2007 | Turnell et al. |
| 2007/0178159 A1 | 8/2007 | Chen et al. |
| 2007/0184084 A1 | 8/2007 | Chen et al. |
| 2007/0185032 A1 | 8/2007 | Gefter et al. |
| 2007/0185033 A1 | 8/2007 | Gefter et al. |
| 2007/0196415 A1 | 8/2007 | Chen et al. |
| 2007/0196416 A1 | 8/2007 | Li et al. |

(56) References Cited

U.S. PATENT DOCUMENTS

| | | |
|---|---|---|
| 2007/0244265 A1 | 10/2007 | Matyjaszewski et al. |
| 2008/0069801 A1 | 3/2008 | Lee et al. |
| 2008/0145419 A1 | 6/2008 | Gibson et al. |
| 2008/0146652 A1 | 6/2008 | Liggins et al. |
| 2008/0152708 A1 | 6/2008 | Gibson et al. |
| 2008/0152724 A1 | 6/2008 | Hirsh |
| 2008/0167630 A1 | 7/2008 | Verity |
| 2008/0176785 A1 | 7/2008 | Brown et al. |
| 2008/0213350 A1 | 9/2008 | Ko et al. |
| 2008/0220074 A1 | 9/2008 | Bosch et al. |
| 2008/0241257 A1 | 10/2008 | Popsecu et al. |
| 2008/0249049 A1 | 10/2008 | Kataoka et al. |
| 2008/0254086 A1 | 10/2008 | Brown et al. |
| 2008/0279954 A1 | 11/2008 | Davis et al. |
| 2008/0287464 A1 | 11/2008 | Wright et al. |
| 2008/0299046 A1 | 12/2008 | White et al. |
| 2008/0299168 A1 | 12/2008 | Dadey et al. |
| 2009/0012027 A1 | 1/2009 | Wang et al. |
| 2009/0022746 A1 | 1/2009 | Simon et al. |
| 2009/0036490 A1 | 2/2009 | Verity |
| 2009/0054619 A1 | 2/2009 | Baker et al. |
| 2009/0069561 A1 | 3/2009 | Fokin et al. |
| 2009/0069569 A1 | 3/2009 | Nolan et al. |
| 2009/0098200 A1 | 4/2009 | Temtsin Krayz et al. |
| 2009/0124535 A1 | 5/2009 | Markland et al. |
| 2009/0148384 A1 | 6/2009 | Fischer et al. |
| 2009/0176892 A1 | 7/2009 | Castillo et al. |
| 2009/0181068 A1 | 7/2009 | Dunn et al. |
| 2009/0203768 A1 | 8/2009 | Mori et al. |
| 2009/0240030 A1 | 9/2009 | Ju et al. |
| 2009/0263441 A1 | 10/2009 | McKay |
| 2009/0280181 A1 | 11/2009 | Slager |
| 2010/0004390 A1 | 1/2010 | Turnell et al. |
| 2010/0016267 A1 | 1/2010 | Theeuwes et al. |
| 2010/0022457 A1 | 1/2010 | Qian et al. |
| 2010/0022481 A1 | 1/2010 | Wang et al. |
| 2010/0029542 A1 | 2/2010 | Jezek |
| 2010/0034801 A1 | 2/2010 | Li et al. |
| 2010/0048736 A1 | 2/2010 | Liu et al. |
| 2010/0104638 A1 | 4/2010 | Dai et al. |
| 2010/0111829 A1 | 5/2010 | Drapeau et al. |
| 2010/0119593 A1 | 5/2010 | Liao et al. |
| 2010/0121022 A1 | 5/2010 | Musa et al. |
| 2010/0166820 A1 | 7/2010 | Boden et al. |
| 2010/0196280 A1 | 8/2010 | Fischer et al. |
| 2010/0197871 A1 | 8/2010 | Finn et al. |
| 2010/0210505 A1 | 8/2010 | Bossard et al. |
| 2010/0216705 A1 | 8/2010 | Chung |
| 2010/0280047 A1 | 11/2010 | Koller et al. |
| 2010/0285113 A1 | 11/2010 | Shoichet et al. |
| 2010/0329981 A1 | 12/2010 | Chang et al. |
| 2011/0009451 A1 | 1/2011 | Verity |
| 2011/0046181 A1 | 2/2011 | Chen et al. |
| 2011/0046606 A1 | 2/2011 | Chen et al. |
| 2011/0052697 A1 | 3/2011 | Farokhzad et al. |
| 2011/0077581 A1 | 3/2011 | Oyelere et al. |
| 2011/0111029 A1 | 5/2011 | Schmitz et al. |
| 2011/0129422 A1 | 6/2011 | Markland et al. |
| 2011/0142951 A1* | 6/2011 | Johnson |
| 2011/0143434 A1 | 6/2011 | Stayton |
| 2011/0189299 A1 | 8/2011 | Okubo et al. |
| 2011/0207834 A1 | 8/2011 | Kim et al. |
| 2011/0257253 A1 | 10/2011 | Seo et al. |
| 2011/0293522 A1 | 12/2011 | Wang et al. |
| 2012/0058139 A1 | 3/2012 | Pitard et al. |
| 2012/0134926 A1 | 5/2012 | Lynn et al. |
| 2012/0202263 A1 | 8/2012 | Blakely et al. |
| 2012/0225033 A1 | 9/2012 | Van Osdol et al. |
| 2012/0251607 A1 | 10/2012 | Coady et al. |
| 2012/0269895 A1 | 10/2012 | Sousa Herves et al. |
| 2012/0270927 A1 | 10/2012 | Reineke |
| 2012/0283187 A1 | 11/2012 | Yamamoto et al. |
| 2012/0321719 A1 | 12/2012 | McDonnell et al. |
| 2012/0330002 A1 | 12/2012 | Cordova et al. |
| 2013/0046084 A1 | 2/2013 | Brown et al. |
| 2013/0059007 A1 | 3/2013 | Mehta et al. |
| 2013/0071444 A1 | 3/2013 | Wang et al. |
| 2013/0090237 A1 | 4/2013 | Mohanty |
| 2013/0095186 A1 | 4/2013 | Na et al. |
| 2013/0115192 A1 | 5/2013 | Ali et al. |
| 2013/0259907 A1 | 10/2013 | Van Osdol et al. |
| 2014/0005341 A1 | 1/2014 | Tang et al. |
| 2014/0193365 A1 | 7/2014 | Van Osdol et al. |
| 2014/0322853 A1 | 10/2014 | Chochos et al. |
| 2015/0018520 A1 | 1/2015 | Houghland |
| 2015/0057419 A1 | 2/2015 | Asandei |
| 2015/0166507 A1 | 6/2015 | Kamal et al. |
| 2015/0240006 A1 | 8/2015 | Carlson et al. |
| 2015/0258102 A1 | 9/2015 | Bagrodia et al. |

FOREIGN PATENT DOCUMENTS

| | | |
|---|---|---|
| EP | 0551535 | 7/1993 |
| EP | 0565618 | 10/1993 |
| EP | 0285057 | 3/1995 |
| EP | 0958369 | 11/1999 |
| EP | 1108048 | 6/2001 |
| EP | 0949905 | 7/2001 |
| EP | 0862416 | 9/2002 |
| EP | 1348444 | 10/2003 |
| EP | 1477510 | 11/2004 |
| EP | 1274459 | 11/2005 |
| EP | 0959873 | 3/2006 |
| EP | 1526835 | 4/2008 |
| EP | 1581181 | 12/2008 |
| EP | 1539101 | 1/2009 |
| EP | 1446099 | 7/2009 |
| EP | 2136788 | 12/2009 |
| EP | 2267027 | 12/2010 |
| EP | 2311431 | 4/2011 |
| EP | 1446100 | 5/2011 |
| EP | 2316421 | 5/2011 |
| EP | 2348125 | 7/2011 |
| EP | 2516504 | 10/2012 |
| JP | 55/62902 | 5/1980 |
| JP | H8-3064 | 1/1996 |
| JP | 8-501064 A | 2/1996 |
| JP | 2001-509146 | 7/2001 |
| JP | 2004-536036 | 12/2004 |
| JP | 2008-525457 | 4/2008 |
| JP | 2008-535610 | 4/2008 |
| WO | 90/03768 | 4/1990 |
| WO | 91/18927 | 12/1991 |
| WO | 93/24150 | 12/1993 |
| WO | 94/19373 | 9/1994 |
| WO | 95/13799 | 5/1995 |
| WO | 95/17901 | 7/1995 |
| WO | 96/18417 | 6/1996 |
| WO | 96/03995 | 12/1996 |
| WO | 96/40072 | 12/1996 |
| WO | 98/27962 | 7/1998 |
| WO | 98/27963 | 7/1998 |
| WO | 99/29839 | 6/1999 |
| WO | 99/37757 | 7/1999 |
| WO | 99/47073 | 9/1999 |
| WO | 00/074650 | 12/2000 |
| WO | 01/13723 | 3/2001 |
| WO | 01/17522 | 3/2001 |
| WO | 01/18041 | 3/2001 |
| WO | 01/026677 | 4/2001 |
| WO | 01/28525 | 4/2001 |
| WO | 01/78683 | 10/2001 |
| WO | 02/000261 | 1/2002 |
| WO | 02/09699 | 2/2002 |
| WO | 02/15877 | 2/2002 |
| WO | 02/058670 | 8/2002 |
| WO | 02/067991 | 9/2002 |
| WO | 02/083166 | 10/2002 |
| WO | 03/041684 A2 | 5/2003 |
| WO | 03/041685 A1 | 5/2003 |
| WO | 03/041757 A2 | 5/2003 |
| WO | 03/058203 | 7/2003 |
| WO | 04/011054 | 2/2004 |
| WO | 04/012703 | 2/2004 |

(56) References Cited

FOREIGN PATENT DOCUMENTS

| | | |
|---|---|---|
| WO | 04/043432 | 5/2004 |
| WO | 04/060920 | 7/2004 |
| WO | 04/093823 | 11/2004 |
| WO | 05/048989 | 6/2005 |
| WO | 2005/087818 | 9/2005 |
| WO | 2006/044660 | 10/2005 |
| WO | 05/112977 | 12/2005 |
| WO | 2007/004067 | 4/2006 |
| WO | 06/072613 | 7/2006 |
| WO | 2007/035296 | 3/2007 |
| WO | 07/076131 | 7/2007 |
| WO | 07/076371 | 7/2007 |
| WO | 2007/131286 | 11/2007 |
| WO | 08/079963 | 7/2008 |
| WO | 08/124013 | 10/2008 |
| WO | 2008/130327 | 10/2008 |
| WO | 08/156503 | 12/2008 |
| WO | 09/065077 | 5/2009 |
| WO | 2009/074274 | 6/2009 |
| WO | 2010/068864 | 6/2010 |
| WO | 2011/060553 | 5/2011 |
| WO | 2011/079188 | 6/2011 |
| WO | 2011/136645 | 11/2011 |
| WO | 2012/017288 | 2/2012 |
| WO | 2012/109363 | 8/2012 |
| WO | 2012/116434 | 9/2012 |
| WO | 2012/126005 | 9/2012 |
| WO | 2013/036847 | 3/2013 |
| WO | 2013/076169 | 5/2013 |
| WO | 2013/078396 | 5/2013 |
| WO | 2013/084204 | 6/2013 |
| WO | 2013/092998 | 6/2013 |
| WO | 2013/113071 | 8/2013 |
| WO | 2013/181697 | 12/2013 |
| WO | 2014/014852 | 1/2014 |
| WO | 2014/022365 | 2/2014 |
| WO | 2014/022535 | 2/2014 |
| WO | 2014/022720 | 2/2014 |
| WO | 2014/044872 | 3/2014 |
| WO | 2014/059446 | 4/2014 |
| WO | 2014/065661 | 5/2014 |
| WO | 2014/096551 | 6/2014 |
| WO | 2014/161815 | 10/2014 |
| WO | 2014/165792 | 10/2014 |
| WO | 2014/168721 | 10/2014 |
| WO | 2014/168986 | 10/2014 |
| WO | 2014/169708 | 10/2014 |
| WO | 2014/172685 | 10/2014 |
| WO | 2014/172885 | 10/2014 |
| WO | 2014/175838 | 10/2014 |
| WO | 2014/176355 | 10/2014 |
| WO | 2014/177771 | 11/2014 |
| WO | 2014/185975 | 11/2014 |
| WO | 2014/186301 | 11/2014 |
| WO | 2014/186905 | 11/2014 |
| WO | 2014/187957 | 11/2014 |
| WO | 2014/189370 | 11/2014 |
| WO | 2014/190199 | 11/2014 |
| WO | 2014/197744 | 12/2014 |
| WO | 2014/198342 | 12/2014 |
| WO | 2014/202775 | 12/2014 |
| WO | 2014/203189 | 12/2014 |
| WO | 2014/204264 | 12/2014 |
| WO | 2014/205072 | 12/2014 |
| WO | 2014/205317 | 12/2014 |
| WO | 2014/207245 | 12/2014 |
| WO | 2014/210132 | 12/2014 |
| WO | 2015/001117 | 1/2015 |
| WO | 2015/006374 | 1/2015 |
| WO | 2015/006555 | 1/2015 |
| WO | 2015/006626 | 1/2015 |
| WO | 2015/007771 | 1/2015 |
| WO | 2015/010020 | 1/2015 |
| WO | 2015/011441 | 1/2015 |
| WO | 2015/015517 | 2/2015 |
| WO | 2015/020206 | 2/2015 |
| WO | 2015/021432 | 2/2015 |
| WO | 2015/023631 | 2/2015 |
| WO | 2015/023724 | 2/2015 |
| WO | 2015/023879 | 2/2015 |
| WO | 2015/026845 | 2/2015 |
| WO | 2015/027159 | 2/2015 |
| WO | 2015/033313 | 3/2015 |
| WO | 2015/034846 | 3/2015 |
| WO | 2015/035020 | 3/2015 |
| WO | 2015/035051 | 3/2015 |
| WO | 2015/035423 | 3/2015 |
| WO | 2015/038904 | 3/2015 |
| WO | 2015/038933 | 3/2015 |
| WO | 2015/041550 | 3/2015 |
| WO | 2015/048728 | 4/2015 |
| WO | 2015/050467 | 4/2015 |
| WO | 2015/051030 | 4/2015 |
| WO | 2015/057009 | 4/2015 |
| WO | 2015/057065 | 4/2015 |
| WO | 2015/057671 | 4/2015 |
| WO | 2015/057852 | 4/2015 |
| WO | 2015/061321 | 4/2015 |
| WO | 2015/062516 | 5/2015 |
| WO | 2015/065168 | 5/2015 |
| WO | 2015/065773 | 5/2015 |
| WO | 2015/068174 | 5/2015 |
| WO | 2015/068532 | 5/2015 |
| WO | 2015/069932 | 5/2015 |
| WO | 2015/077753 | 5/2015 |
| WO | 2015/077831 | 6/2015 |
| WO | 2015/081858 | 6/2015 |
| WO | 2015/084846 | 6/2015 |
| WO | 2015/084861 | 6/2015 |
| WO | 2015/085268 | 6/2015 |
| WO | 2015/087340 | 6/2015 |
| WO | 2015/088990 | 6/2015 |
| WO | 2015/089506 | 6/2015 |
| WO | 2015/104374 | 7/2015 |
| WO | 2015/105549 | 7/2015 |
| WO | 2015/107115 | 7/2015 |
| WO | 2015/112014 | 7/2015 |
| WO | 2015/112809 | 7/2015 |
| WO | 2015/114663 | 8/2015 |
| WO | 2015/116711 | 8/2015 |
| WO | 2015/116739 | 8/2015 |
| WO | 2015/121189 | 8/2015 |
| WO | 2015/121225 | 8/2015 |
| WO | 2015/121228 | 8/2015 |
| WO | 2015/130835 | 9/2015 |
| WO | 2015/130843 | 9/2015 |
| WO | 2015/130878 | 9/2015 |
| WO | 2015/134599 | 9/2015 |
| WO | 2015/136477 | 9/2015 |

OTHER PUBLICATIONS

Agalave et al. (Chem. Asian J., 6:2696-2718 (2011)) (Year: 2011).*
Wang, J., "The Modern Methods and Technology of Polymer Synthesis," Tongji Press, pp. 209-211, Jul. 2013.
Lee, J.S., et al., "The effect of gamma irradiation on PLGA and release behavior of BCNU from PLGA wafer," *Macromol. Res.*, vol. 11(5), pp. 352-356, 2003.
Ablinger, et al., Convergence abstract PDD04, presented at the 8th Central European Symposium on Pharmaceutical Technology, Sep. 16-18, 2010; abstract only.
Agard, N.; Prescher, J.; et al., "A strain-promoted [3+2] azide-alkyne cycloaddition for covalent modification of biomolecules in living systems," *J. Am. Chem. Soc.*, 2004, 126, 15046-15047.
Aragao-Leoneti, V., et al., "Application of copper(I)-catalysed azide/alkyne cycloaddition (CuAAC) 'click chemistry' in carbohydrate drug and neoglycopolymer synthesis," *Tetrahedron*' 66(49), pp. 9475-9492, 2010.
Arnold, FH et al., "Metal-Mediated Protein Stabilization", *Trends in Biotechnology*, May 1994, 12(5), 189-92.
Arnold, L.D.; Kalantar, T.H.; et al., *J. Amer. Chem. Soc.* (1985), 107, 7105-7109).

(56) References Cited

OTHER PUBLICATIONS

Azida (Hemp oil body care products, 2007 update), http://www.azida.com/ingredients.html, pp. 1-2.
Barton, et al., "Observations on the dynamics of nonsolvent-induced phase inversion", *J. Poly. Sci.* 35(4): 569-585, 1997.
Blanco, M.D., et al. Bupivacaine-loaded comatrix formed by albumin microspheres included in a poly (lactide-coglycolide) film: in vivo biocompatibility and drug release studies, *Biomaterials*, vol. 20, pp. 1919-1924, 1999.
Brodbeck, et al., "Phase inversion dynamics of PLGA solutions related to drug delivery, Part II. The role of solution thermodynamics and bath side mass transfer", *J. Control. Release*, 62(3):333-344, 1999.
Brodbeck, Kevin J., et al., "Sustained release of human growth hormone from PLGA solution depots", *Pharmaceutical Research*, vol. 16, No. 12, Dec. 1, 1999, pp. 1825-1829.
Carberry, T.P.; Tarallo, R.; et al., "Dendrimer funtionalization with a membrane-interacting domain of herpes simplex virus type 1: towards intracellular delivery.", *Chemistry*. Oct. 22, 2012;18(43):13678-85.
Castillo, G.; Reichstetter, S.; et al., "Extending residence time and stability of peptides by protected graft copolymer (PGC) excipient: GLP-I example," *Pharm Res.* DOI 10.1007/s11095-011-0542-2.
Chen, C.K.; Law, W.C.; et al., "Well-defined degradable cationic polylactide as nanocarrier for the delivery of siRNA to silence angiogenesis in prostate cancer." *Adv. Healthc. Mater.* Nov. 2012; 1(6):751-61.
Chen, et al., "Alzamer depotTM bioerodible polymer technology" *Mod. Rel. Drug Deliv. Tech.*, First Edition, Ed. Rathbon & Roberts, Chapter 18, pp. 215-225, 2002.
Chen, et al., "Controlled delivery of testosterone from smart polymer solution based systems: in vitro evaluation", *Int. J. Pharma.*, 295 pp. 183-190, 2005.
Chen, B., et al., "The influence of polymer topology on pharmacokinetics: Differences between cyclic and linear PEGylated poly(aciylic acid) comb polymers," *J. Control. Rel.*, 140:3, pp. 203-209, 2009.
Chen, Y., et al.; "pH-sensitive supmmolecular polypeptide-based micelles and reverse micelles mediated by hydrogen-bonding interactions or host-guest chemistry: characterization and in vitro controlled drug release," *J.Phys. Chem. B.*, 114(22) pp. 7461-7468, Jun. 10, 2010.
Cleland, J.L., "Injectable gels for local systemic delivery of proteins", Proceed. Int'l Symp. Control. Rel. Bioact. Mater., 28 (2001), Controlled Release Society, Inc. pp. 45-46.
Cooper, C.L.; Dubin, P.L.; Kayitmazer, A.B.; Turksen, S., "Polyelectrolyte-protein complexes". *Current Opinion in Colloid & Interface Science*, 10 (2005) pp. 52-78.
Crescenzi, v., et al.; "Novel hydrogels via click chemistry: synthesis and potential biomedical applications," *Biomacromolecules*, 8(6) pp. 1844-1850, 2007.
Crownover, E., et al., "RAFT-synthesized graft copolymers that enhance pH-dependent membrane destabilization and protein circulation times." *J. Control. Rel.*, 155(2), pp. 167-174, 2011.
Desoyner, et al., "Role of crystallization in the phase inversion dynamics and protein release kinetics of injectable drug delivery systems", *J. Control. Release*, 70(3):285-294, 2001.
Ding, J., et al., "Efficacious hepatoma-targeted nanomedicine self-assembled from galactopeptide and doxorubicin driven by two-stage physical interactions," *J. Control. Rel.*, 169:3, pp. 193-203, 2013.
Doane, T., et al., "Nanoparticle mediated non-covalent drug delivery," *Adv .Drug Del. Rev.*, 65:5, pp. 607-621, 2013.
Dohmen, C.; Fröhlich, T.; et al., "Devined folate-PEG-siRNA conjugates for receptor-specific gene silencing." *Mol. Ther. Nucleic Acids*. Jan. 31, 2012; 1:e7.
Dong, X., et al., "Synthesis of biodegradable dextmn-g-(PCL-b-PEG) by combination of ring-opening polymerization and click chemistry," *J. Control. Rel.*, 152:1, pp. e198-e199, 2011.

Duenas, E, et al. "Sustained Delivery of rhVEGF from a nobel injectable liquid, plad" *Proceed. Int'l. Symp. Control. Rel. Bioact. Mater.*, vol. 28, 2001.
English Translation Office Action dated Nov. 22, 2011, from Japanese Application No. 2008-518516.
Fietier, I.; Le Borgne, A.; Spassky, N., "Synthesis of functional polyesters derived from serine". *Polymer Bull*. 1990, 24, 349-353.
Freichels, H.; Alaimo, D.; et al., "α-Acetal, ω-alkyne poly(elthylene oxide) as a versatile building block for the synthesis of glycoconjugated graft-copolymers suited for targeted drug delivery.", *Bioconjug. Chem.* Sep. 19, 2012;23(9):1740-52.
Fujita, et al. (2002) Antifungal activity of octyl gallate, *International J. Food Microbiol.*, vol. 79, No. 3, pp. 193-201.
Garry, M.G. et al. "Evaluation of the efficiency of a bioerodible bupivacaine polymer system on antinociception and inflammatory mediator release," *Pain*, vol. 82, pp. 49-55, 1999.
Gelbin, M.E.; Kohn, J., Synthesis and polymerization of N-Z-L-serine β-lactone and serine hydroxybenzotriazole active esters. *J. Am. Chem. Soc.*, 1992, 114(10), pp. 3962-3965.
Graham, et al., "Phase inversion dynamics of PLGA solutions related to drug delivery", *J. Control Rel.*, 58(2):233-245, 1999.
Gregory, A., et al., "Complex polymer architectures via RAFT polymerization: From fundamental process to extending the scope using click chemistry and nature's building blocks," *Prog. In Polym. Sci.*, 37(1), pp. 38-105, 2012.
Guevello, P. Le et al. "High performance liquid chromatographic determination of bupivacaine in plasma samples for biopharmaceutical. studies and application to seven other local anesthetics." *Journal of Chromatography*, vol. 622, pp. 284-290, (1993).
Gupta, S.; Schade, B.; et al., "Non-ionic dendronized multiamphiphilic polymers as nanocarriers for biomedical applications." *Small*. Dec. 6, 2012.
He, X.; Wu, X.; et al., "Functionalization of magnetic nanoparticles with dendritic-linear-brush-like triblock copolymers and their drug release properties.", *Langmuir*. Aug. 14, 2012;28(32):11929-38.
Huang, C., et al., "Polymeric nanoparticles with encapsulated superparamagnetic iron oxide and conjugated cisplatin for potential bladder cancer therapy," *Biomacromolecules*, 13(8), pp. 2513-2520, Jul. 2012.
Isaacman, M.J.; Barron, K.A.; et al., "Clickable Amphiphilic Triblock Copolymers.", *J. Polym, Sci. A. Polym, Chem.* Jun. 15, 2012;50(12):2319-2329.
Ke, et al., "Enhanced oral bioavailability of doxombicin in a dendrimer drug delivery system.", *J. Pharmaceutical Sciences*. vol. 97, No. 6, Jun. 2008. pp. 2208-2216.
Kikwai, Loice, et al., "In vitro and in vivo evaluation of topical formulations of spantide II, AAPS" PharmSciTech; 2005; 6(4): E565-E572.
King, A., "Harvard develops new nanoparticle as drug delivery device," www.in-pharmatechnologist.com copyright 2014 William Reed Business Media SAS.
Kohn, J., Pseudopoly(amino acids). In: Biodegradable polymers as drug delivery systems, R. Langer, M. Chasin eds., NY: Marcel Dekker, pp. 195-229.
Kokufuta, E., Complexation of proteins with polyelectrolytes in a salt-free system and biochemical characteristics of the resulting complexes, in: P.L. Dubin, J. Bock, R.M. Davies, D.N. Schulz, C. Theis (Eds.), Macromolecular Complexes in Chemistry and Bioloby, Springer-Verlag, Berlin Heidelberg, 1994, pp. 301-325.
Kolb, H.; Finn, M.; et al., *Angew. Chem. Int. Ed.* (2001) 40, 2004-2021.6.
Kolb, H.; Sharpless, K., "The growing impact of click chemistry on drug discovery," *Drug Discovery Today*, 8(24) pp. 1128-1137, Dec. 15, 2003.
Krause, A., et al., "Bioorthogonal metal-free click-ligation of cRGD-pentapeptide to alginate," *Org. Biomol. Chem*. 10, pp. 5547-5553, 2012.
Kwon, et al., "Long acting porous microparticle for pulmonary protein delivery", *Int. J. Pharm.*, 333(1-2):5-9, 2007.
Lambert, W.J. et al. "Development of an in situ forming biodegradable poly-lactide-co-glycolide system for controlled release of proteins." *Journal of Controlled Release*, vol. 33, pp. 189-195 (1995).

(56) References Cited

OTHER PUBLICATIONS

Leung, M.K.; Hagemeyer, C.E.; et al., "Bio-click chemistry: enzymatic functionalization of PEGylated capsules for targeting applications." *Angew.Chem Int Ed Engl*. Jul. 16, 2012;51(29):7132-6.
Lee, R.S.; Huang, Y.T., *J. Polym. Sci.: Part A: Polym. Chem*. (2008), 46, 4320-4331.
Lenoir, S.; Riva, R.; et al., *Macromol*. (2004) 37, 4055-4061.
Liang, K.; Such, G.K.; et al., "Engineering cellular degradation of multilayered capsules through controlled cross-linking ", *ACS Nano*. Nov. 27, 2012;6(11):10186-94.
Liang, L., et al., "The copper(1)-catalyzed alkyne-azide cycloaddition (CuAAC) "click" reaction and its applications. An overview," *Coordination Chemistry Reviews*, 255(23-24, pp. 2933-2945, 2011.
Liu, Xin-Ming, et al., "Novel biomineral-binding cyclodextrins for controlled drug delivery in the oral cavity," *J. Control. Rel*., 122:11, pp. 54-2, 2007.
Lu, et al., "Rheological properties of sucrose acetate isobutyrate in situ gel", Yao Xue Xue Bao 42(4):445-449, 2007. Abstract only.
Lu, et al., "Sucrose acetate isobutyrate as in situ forming system for sustained risperidone release", *J. Pharm. Sci*., 96(12):3252-3262, 2007.
Lutz, J., et al., "Efficient construction of therapeutics, bioconjugates, biomaterials and bioactive surfaces using azide—alkyne "click" chemistry," *Adv. Drug Del. Rev.*, 60(9), pp. 958-970, 2008.
Lutz, J.-F. and Sumerlin, B. S., "The Role of Click Chemistry in Polymer Synthesis," *Click Chemistry for Biotechnology and Materials Science (ed J. Lahann)*, John Wiley & Sons, Ltd, Chichester, UK. doi: 10.1002/9780470748862.ch5.
Ma, et al., "The interplay of phase inversion and membrane formation in the drug release characteristics of a membrane based delivery system", *J. Membrane Sci*. 298(1-2):156-168, 2007.
Manocha, B.; Margaritis, A., "Controlled release of doxorubicin from doxorubicin/γ-polyglutamic acid ionic complex," *J. Nanomater*. vol. 2010, Article IS 780171, DOI:10.1155/2010/780171.
Masuyama, Y., et al., "Hydroxyapatite-supported copper(II)-catalyzed azide-alkyne [3+2] cycloaddition with neither reducing atgents nor bases in water," *Tetrahedron Letters*, 52:51, pp. 6916-6918, 2011.
Matsudo, T.; Ogawa, K.; Kokufuta, E., "Complex formulation of protein with different water-soluable synthetic polymers". *Biomacromol*. 2003, 4, 1794-1799.
McHugh, et al., "The role of polymer membrane formation in sustained release drug delivery systems", *J. Controlled Release*, 109 pp. 211-221, 2005.
McHugh, et al., "Injectable drug delivery based on polymer solutions: Experiment and Modeling" Polymeric Drug Delivery II: Polymeric Matrices and Drug Particle Engineering Ed. Svenson, Chapter 2, pp. 14-28. 2006.
McHugh, et al., "Dynamics of the phase inversion process" *J. Appl. Poly. Sci*. 46(11):2011-2021. 1992.
McKinnon, D., et al., "Design and Characterization of a Synthetically Accessible, Photodegradable Hydrogel for User-Directed Formation of Neural Networks," *Biomacromolecules*, 15(7), pp. 2808-2816, 2014.
Merck Index, monograph 01126, 2005.
Na, et al., Formulation of acylated growth hormone-releasing peptide-6 by poly(lactide-co-glycolide) and its biological activity AAPS PharmSciTech 8(2):Article 43. 2007.
Ng; Sheer; et al., "Controlled release of DNA from poly(vinylpyrrolidone) capsules using cleavable linkers," *Biomater*., 32(26) pp. 6277-6284.
Nottelet, B.; El Ghaoui, A.; et al., *Biomacromol*. (2007), 8, 2594-2601.
Okumu, F.W., et al. Sustained delivery of growth hormone from a novel injectable liquid plad,: *Proceed. Int'l Symp. Control. Rel. Bioact. Mater.*, vol. 28, 2001.
Okumu, F. W. et al., "Evaluation of the SaberTM Delivery System for sustained release growth hormone-formulation design and in vivo assessment," *Proced. Int'l, Symp. Control, Rel.Bioact. Mater.*, vol. 28, 2001.

Okumu, et al. "Sustained delivery of human growth hormone from a novel gel system: SaberTM", *Biomater.*, 23(22)4353-4358, 2002.
Opsteen, J.A., et al., "Modular synthesis of block copolymers via cycloaddition of terminal azide and alkyne functionalized polymers," *Chemical Communications*, 1, pp. 57-59, 2005.
Park, et al., "Sustained delivery of human growth hormone using a polyelectrolyte complex-loaded thermosensitive polyphosphazene hydrogel", *J. Control. Release*, 147(3):359-367, 2010.
Parrish, B.; et al., *J. Amer. Chem. Soc*. (2005), 127, 7404-7410.
Philip, B.K. et al. "the economic impact of opioids on postoperative pain management," *Journal of Clinical Anethesia*, vol. 14, pp. 354-364, 2002.
Ponsart, S.; Coudane, J.; et al., *Biomacromol*. (2000), 1, 275-281.
Portis, A.; Carballo, G; et al., *Microsc. Res. Tech*. (2010), 73, 878-885.
Priftis, D.; Laugel, N.; et al., "Thermodynamic Characterization of polypeptide complex coacervation," *Langmuir*, 2012, 28, 15947-15957.
Priftis, D; Tirrell, M., "Phase behavior and complex coacervation of aqueous polypeptide solutions," *Soft Matter*, 2012, 8, 9396.
Putnam, D.; Langer, R., "Poly(4-hydroxy-L-proline ester): Low-temperature polycondensation and plasmid DNA complexation". *Macromol*. 1999, 32, 3658-3662.
Qi, R., et al., "Biodegradable copolymers with identical cationic segments and their performance in siRNA delivery," *J. Control. Rel.*, 152:2, pp.. 251-260, 2012.
Rickerby, J.; Prabhakar, R.; et al., "A biomedical library of serinol-derived polyesters," *J. Control. Rel*. 101 (2005) 21-34.
Riva, R.; Schmeits, C.; et al., *Macromol*. (2007) 40, 796-803.
Sanchez-Sanchez, A., et al., "Advances in click chemistry for single-chain nanoparticle contruction," *Molecules*, 18(3), pp. 3339-3355, 2013.
Schlievert et al., "Effect of glycerol monolaurate on bacterial growth and toxin production," *Antimicrob. Agents and Chemother.*, vol. 36 (3), Mar. 1992, pp. 626-631.
Sekar, M.;Van Osdol, W.; et al., Organic solvent-free subcutaneous aqueous depot for GLP-1 peptide delivery, *Boulder Peptide Society Meeting*, Sep. 28, 2015, Boulder, Colorado.
Sekar, M.; Van Osdol, W.; et al., "Continuous delivery of interferon-α2a via subcutaneous depots," AAPS meeting, Washington, D.C., Oct. 23-27, 2011.
Sekar, M.; Van Osdol, W.; et al., "Controlled delivery depots of liraglutide, a GLP-1 analogue, via subcutaneous injection," TIDES meeting, San Diego, May 3-6, 2015.
Sekar, M.; Van Osdol, W.; et al., "Drug delivery of biologics: A contolled release strategy," May 3-6, 2015.
Shen, L.; Garland, A.; et al., "Two dimensional nanoarrays of individual protein molecules.", *Small*. Oct. 22, 2012;8(20):3169-74.
Shenoi, R.A.; Lai, B.F.; et al., Synthesis, characterization, and biocompatibility of biodegradable hyperbranched polyglycerols from acid-cleavable ketal group functionalized initiators. *Biomacromolecules*. Oct. 8, 2012;13(10):3018-30.
Sliedregt, K.; Schouten, A.; et al., "Reaction of N-Trityl amino acids with BOP: Efficient synthesis of t-Butyl esters as well as N-Trityl Serine- and Threonine-β-lactones". *Tetrahedron Letters*, 1996, vol. 37, No. 24, pp. 4237-4240.
Su, H.; Liu, Y.; et al., "Amphiphilic starlike dextran wrapped superparamagnetic iron oxide nanoparticle clusters as effective magnetic resonance imaging probes.", *Biomater*. Jan. 2013;34(4):1193-203.
Such, G., et al., "Synthesis and funtionalization of nanoengineered materials using click chemistry," *Prog. In Polym. Sci*., 37:7, pp. 985-1003, 2012.
Sun, L; Ma, X; et al., "NIR-responsive and lectin-binding doxorubicin-loaded nanomedicine from janus-type dendritic PAMAM amphiphiles.", *Biomacromolecules.*, Nov. 12, 2012;13(11):3581-91.
Supplies (2007, updated) "ethyl acetate" http://chenucalland21.com/industrialchem/solalc/ETHYL%20ACETATE.htm, pp. 1-4.
Svenson, S., et al.; "Dendrimers in biomedical applications—reflections on the field," 57(15) pp. 2106-2129, 2005.

(56) References Cited

OTHER PUBLICATIONS

Tae, G. et al., "Sustained release of human growth hormone from in situ forming hydrogels using self-assembly of fluoroalkyl-ended poly(ethylene glycol)," *Biolaterials*, Mar. 5, 2005, 26(25), 5259-5266.

Tainer, JA et al., "Protein Metal-Binding Sites", *Current Opinion in Biotechnology*, 1992, 3(4), 378-387.

Takahashi, A., et al., "In Situ Cross-Linkable Hydrogel of Hyaluronan Produced via Copper-Free Click Chemistry," *Biomacromolecules*, 14(10), pp. 3581-3588, 2013.

Tanaka et al., "Denaturation and aggregation of hen egg lysozym in aqueous solution studies by dynamic light scattering," May 8, 2001, Biopolymers, vol. 59, pp. 370-379.

Testa, G., et al., "Influence of dialkyne structure on the properties of new click-gels based on hyaluronic acid," *Int., J. Pharmaceutics*, 378(1-2), pp. 86-92, 2009.

Thomas, T.P.; Huang, B.; et al., "Polyvalent dendrimer-methotrexate as a folate receptor-targeted cancer therapeutic." *Mol. Pharm.*. Sep. 4, 2012;9(9):2669-76.

Ueda et al., (2003) Current and prospective applications of metal ion-protein binding, *J. Chromatogr. A.*, vol. 988, No. 1 pp. 1-23.

Van De Wetering, et al., "Poly(ethylene glycol) hydrogels formed by conjugate addition with controllable swelling, degradation, and release of pharmaceutically active proteins", *J. Control. Release* 102(3):619-627, 2005.

Wang, et al., "Structure Formation in injectable poly(lactide-co-glycolide) depots", *J. Control Release*, 90(3):345-354, 2003.

Wang, et al. "Drug Release from injectable depots: Two different in vitro mechanisms", *J. Control Release*, 99(2):207-216, 2004.

Wang, X.; Liu, L; et al., "Comb-shaped glycopolymer/peptide bioconjugates by combination of RAFT polymerization and thiol-ene "click" chemistry.", *Macromol. Biosci.*, Nov. 2012; 12(11): 1575-82.

Wikipedia (2007, update) Carnauba wax, http://enwikipedia.org/wiki/Carnauba_wax, pp. 1-2.

Wikipedia (2007, update) Fatty alcohol, http://en.wikipedia.org/wiki/Fatty_alcohol, pp. 1-2.

Won, C.Y.; Chu, C.; et al., Novel amine-containing biodegradable polyester via copolymerization of aspartic anhydride and 1,4-cyclohexanedimethanol. *Macromol. Rapid Commun.*, 1996, 17(9), 653-659.

Xia, J.L.; Dubin, P.L., Protein-polyelectrolyte complexes, in: P.L. Dubin, Bock, Davis, Schulz (Eds.), Macromolecular Complexes in Chemistry and Biology, Springer-Verlag, Berlin Heidelberg, 1994, pp. 247-271.

Yang, et al. "Effect of zinc binding and precipitation on structures of recombinant human growth hormone and nerve growth factor", *J. Pharm. Sci.*, 89(11):1480-1485, 2000.

Yilmaz, et al., "Analysis of nonsolvent—solvent-polymer phase diagrams and their relecance to membrane formation modeling", *J. Appl. Poly.Sci.*, vol. 31, 997-1018, 1986.

Yin, H.; et al., "Biocompatible, pH-sensitive AB(2) Miktoarm polymer based polymersomes: preparation, characterization, and acidic pH-activated nanostructural Transformation.", *J. Mater. Chem.*, Sep. 28, 2012;22(36):91968-19178.

Yuan, W., et al., "Amphiphilic chitosan graft copolymer via combination of ROP, ATRP and click chemistry: Synthesis, self-assembly, thermosensitivity, fluorescence, and controlled drug release," *Polymer*, 52(3), pp. 658-666, 2011.

Zhao, L.; Xiao, C.; et al., "Facile one-pot synthesis of glucose-sensitive nanogel via thiol-ene click chemistry for self-regulated drug delivery." *Acta Biomater.* Feb. 9, 2013.

Zhou, Q; Kohn, J., Preparation of Poly(L-serine ester): A structural analogue of conventional Poly(L-serine). *Macromolecules* 1990, 23, pp. 3399-3406.

\* cited by examiner

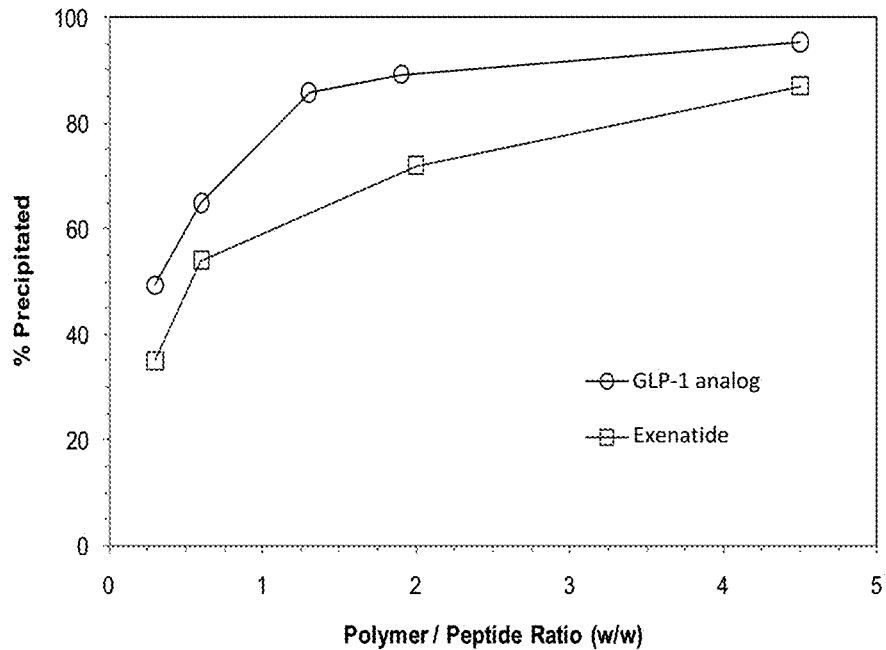
FIG. 1 Polymer (Example 2H): $M_w$ 16.0 kDa
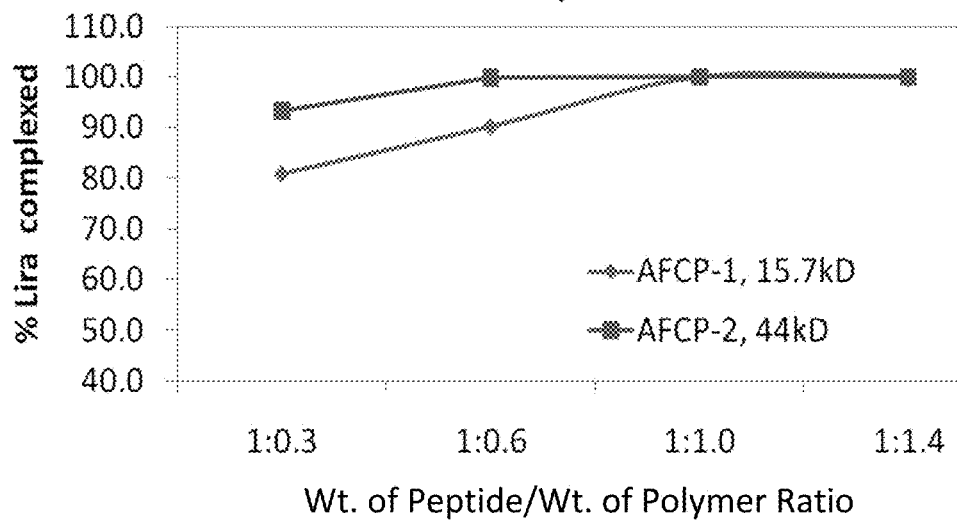
FIG. 2

EX = Exenatide

FIG. 5 2A-(Example 2E (5.6 kDa) and 2B-(Example 2E, (12 kDa) COOH-terminated polymer)

A21 = NH$_2$-NH-PLGA-NH-NH$_2$, 5kDa

Glatiramer
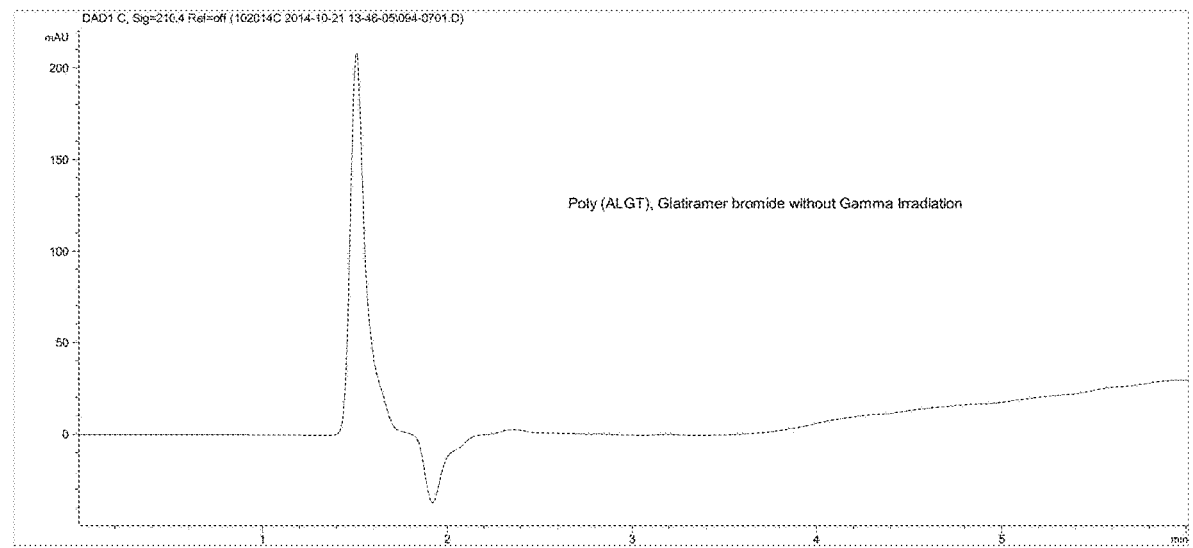
Insulin
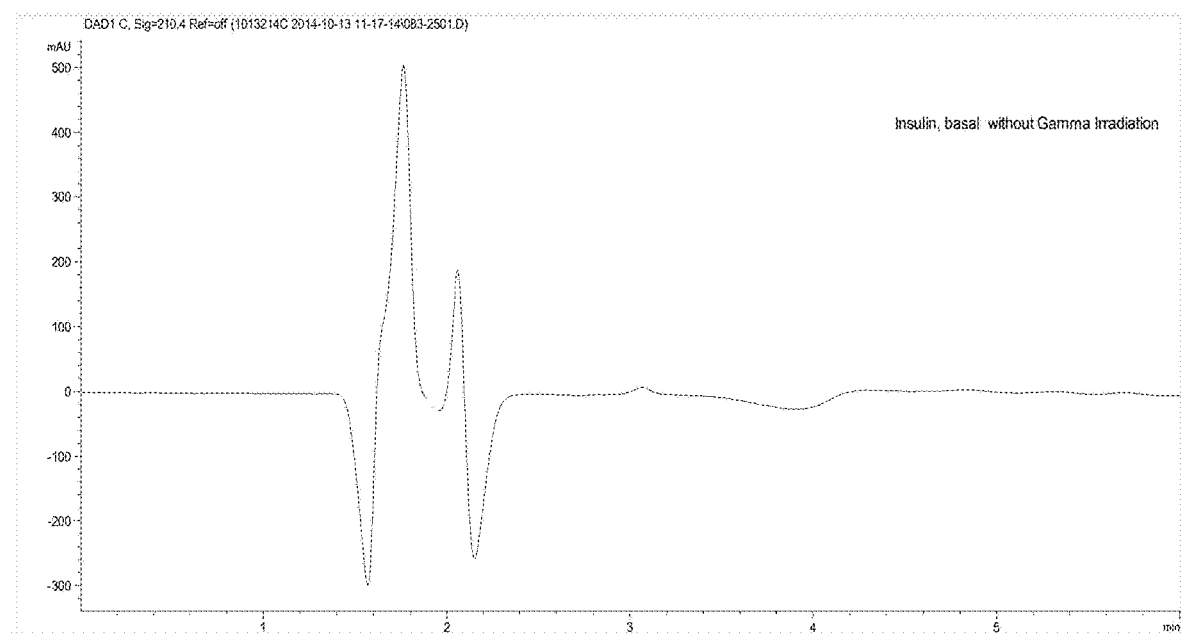
FIG. 28

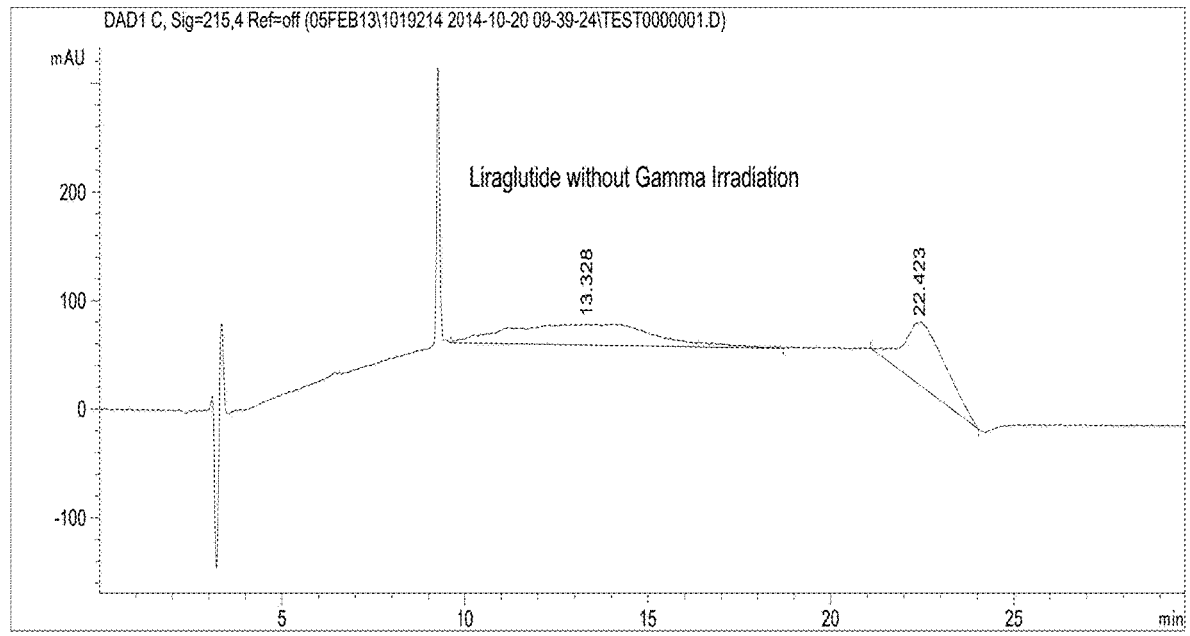
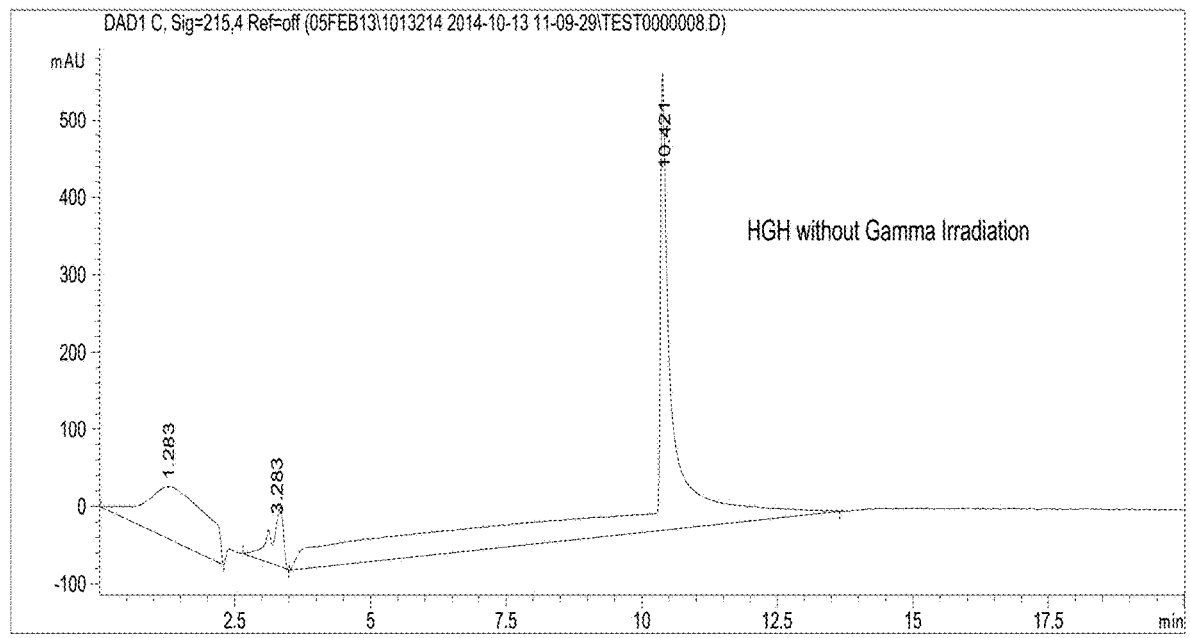
FIG. 29

PHARMACEUTICALLY ACTIVE AGENT COMPLEXES, POLYMER COMPLEXES, AND COMPOSITIONS AND METHODS INVOLVING THE SAME

CROSS-REFERENCE TO RELATED APPLICATIONS

This application claims the benefit of and expressly incorporates by reference herein the entire disclosure of U.S. Provisional Patent Application No. 61/913,827, filed Dec. 9, 2013.

BACKGROUND OF THE INVENTION

Field of the Invention

The present invention relates to complexes including a pharmaceutically active agent and a polymer, to compositions comprising such complexes, and to methods of making and using the same.

Background

The delivery of drugs, including injectable drug formulations, is often accomplished in the art via the use of drug delivery depots. Following injection, drug delivery depots generally release drug in a slow and controlled manner. Drug delivery depots can also reduce and/or eliminate the need for multiple injections. Such depots often include at least polymer, solvent, and drug. In some cases, the drug is highly soluble in the depot and may leave the depot too quickly. In other cases, the drug is unstable in the depot.

The present disclosure addresses these and related issues and provides improved compositions for the controlled release of pharmaceutically active agents along with methods of making and using the same.

SUMMARY OF THE INVENTION

The present disclosure generally provides complexes including a pharmaceutically active agent and a functionalized polymer, wherein the functionalized polymer includes repeat units, the repeat units including ionizable repeat units having at least one ionizable side group and/or ionizable end group, a plurality of the at least one ionizable groups forming non-covalent bonds with the pharmaceutically active agent. Polymers which may be used to form such complexes as well as methods of making and using the complexes and related compositions are also provided. Other features and advantages of the present disclosure will be set forth in the description of invention that follows, and in part will be apparent from the description or may be learned by practice of the invention. The invention will be realized and attained by the compositions and methods particularly pointed out in the written description and claims hereof.

Certain non-limiting aspects of the disclosure are provided below:

A first embodiment of the present disclosure is directed to a complex comprising:
a pharmaceutically active agent, and
a functionalized polymer, the functionalized polymer comprising repeat units, the repeat units comprising ionizable repeat units comprising at least one ionizable side group, a plurality of the at least one ionizable side groups forming a plurality of non-covalent bonds with the pharmaceutically active agent,
wherein at least 10% of the repeat units comprise at least one ionizable side group
wherein the functionalized polymer is optionally synthetic,
wherein the functionalized polymer is optionally a polyester,
wherein the functionalized polymer is optionally linear, and
wherein the functionalized polymer optionally has a weight average molecular weight greater than 15,000 Daltons, as measured by gel permeation chromatography.

A second embodiment of the present disclosure is directed to a complex comprising:
a pharmaceutically active agent; and
a functionalized polymer, the functionalized polymer comprising repeat units, the functionalized polymer comprising at least one of: (a) ionizable repeat units comprising at least one ionizable side group, wherein the at least one ionizable side group comprises at least one member selected from ammonium, carboxylate, hydrazinium, guanidinium, sulfate, sulfonate, and phosphate; and (b) at least one ionizable end group;
wherein a plurality of the at least one ionizable groups form a plurality of non-covalent bonds with the pharmaceutically active agent,
wherein the functionalized polymer is optionally synthetic,
wherein the functionalized polymer is optionally a polyester,
wherein the functionalized polymer is optionally linear, and
wherein the functionalized polymer optionally has a weight average molecular weight greater than 15,000 Daltons, as measured by gel permeation chromatography.

A third embodiment of the present disclosure is directed to a composition comprising:
a complex comprising:
a pharmaceutically active agent, and
a functionalized polymer complexed with the pharmaceutically active agent through non-covalent bonding; and
a vehicle,
wherein the functionalized polymer is optionally synthetic,
wherein the functionalized polymer is optionally a polyester,
wherein the functionalized polymer is optionally linear, and
wherein the functionalized polymer optionally has a weight average molecular weight greater than 15,000 Daltons, as measured by gel permeation chromatography.

A fourth embodiment of the present disclosure is directed to a method comprising:
providing a precursor polymer comprising repeat units, the repeat units comprising functionalizable repeat units comprising at least one functionalizable side group;
obtaining a functionalized polymer by transforming, using click chemistry, said functionalizable repeat units into ionizable repeat units comprising at least one ionizable side group; and
combining the functionalized polymer with a pharmaceutically active agent to form a complex in which a plurality of the at least one ionizable side groups form a plurality of non-covalent bonds with the pharmaceutically active agent.

A fifth embodiment of the present disclosure is directed to a method comprising:

combining a functionalized polymer with a pharmaceutically active agent, the functionalized polymer comprising ionizable repeat units comprising at least one ionizable side group, to form a complex in which a plurality of the at least one ionizable side groups form a plurality of non-covalent bonds with the pharmaceutically active agent.

BRIEF DESCRIPTION OF THE DRAWINGS

The present invention is further described in the description of invention that follows, in reference to the noted plurality of non-limiting drawings, wherein:

FIG. 1 is a graph showing the effect of polymer/peptide ratio on the complexation efficiency of exenatide and a GLP-1 analog.

FIG. 2 is a graph showing the effect of polymer/peptide ratio on the complexation efficiency of liraglutide with two different amine-functionalized 50:50 copolymers.

FIG. 28 provides RPLC spectra showing the stability of uncomplexed glatiramer bromide (top) and uncomplexed insulin (bottom) in the absence of gamma irradiation.

FIG. 29 provides RPLC spectra showing the stability of uncomplexed liraglutide (top) and uncomplexed human growth hormone (bottom) in the absence of gamma irradiation.

DESCRIPTION OF THE INVENTION

Figure 3:
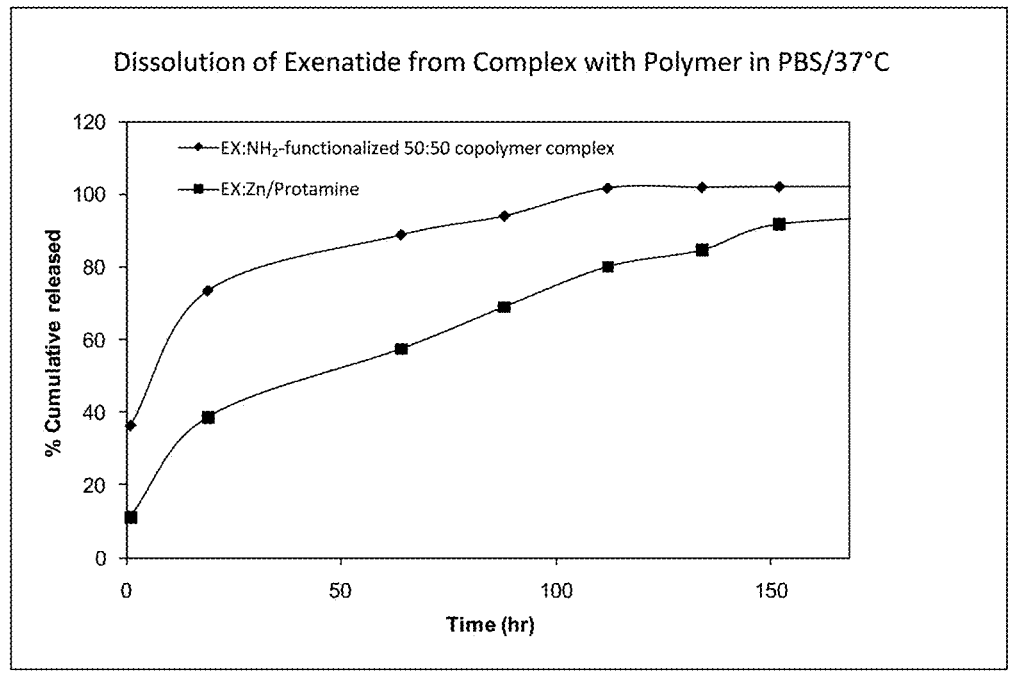
FIG. 3 is a graph showing the dissolution of exenatide from an exenatide:amine-functionalized 50:50 copolymer complex relative to an exenatide:Zn/Protamine complex.

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

Before further discussion, a definition of the following terms will aid in the understanding of the present invention.

As used herein, the term "functionalized polymer" means a polymer that comprises at least one of: (a) ionizable repeat units comprising at least one ionizable side group; and (b) at least one ionizable end group. Thus, a "functionalized polymer" comprises at least one ionizable group. In an embodiment, the "functionalized polymer" comprises at least one ionizable repeat unit comprising at least one ionizable side group.

By "ionizable" or "ionizable group" is meant a moiety that is either ionized or capable of ionization. For instance, an_ionizable group may be ionized in an aqueous solution at a given pH but not at others. Accordingly, the term "ionizable group" encompasses a moiety which is in an ionized form, i.e., a charged group. By "ionizable" or "ionizable group" in a polymer described herein is meant a moiety of the polymer that is either ionized or is capable of ionization to form an ionic bond with the pharmaceutically active agent when the polymer is combined with the pharmaceutically active agent to form a complex. As used herein, the term "ionizable group" with reference to an "ionizable group" on a polymer encompasses both an "ionizable side group" on an ionizable repeat unit comprised within the polymer and an "ionizable end group" on the polymer. Examples of typical ionizable groups include ammonium, carboxylate, hydrazinium, guanidinium, sulfate, sulfonate, phosphonate and phosphate. Consistent with the above definition of "ionizable group", each of the groups ammonium, carboxylate, hydrazinium, guanidinium, sulfate, sulfonate, phosphonate and phosphate includes its corresponding uncharged (but ionizable) moiety, e.g. ammonium includes amino, carboxylate includes carboxylic acid, and so on. Ammonium includes primary, secondary and tertiary ammonium groups (i.e., groups derived from primary, second and tertiary amines), as well as quaternary ammonium. Each such group may also be present one or more times in a given ionizable group, such as in a given ionizable side chain. For example, each such group may be present once, twice or three or even more times. Thus, for example, dicarboxylate, tricarboxylate, diammonium, triammonium, polyamine, and polyamonium groups are all included. Ionizable groups of interest also include, e.g., succinate and spermine.

As used herein, the term "repeat unit" means a unit or residue in a polymer that is derived from a particular monomer. Typically the or each repeat unit is repeated multiple times in the chain of a particular polymer molecule. A homopolymer comprises a plurality of identical repeat units. A copolymer comprises a plurality of different types of repeat unit, each of which is typically present multiple times in the chain of a particular polymer molecule.

As used herein, the term "precursor polymer" means a polymer that can be converted into a "functionalized polymer" as defined herein by transforming functionalizable repeat units in the precursor polymer into ionizable repeat units, for example using the methods described elsewhere herein.

As used herein, the term "functionalizable side group" means a side group that can be converted into an "ionizable side group" as defined herein, for example using the methods described elsewhere herein.

As used herein, the term "polymer intermediate" means a polymer that is an intermediate compound that is produced during the coversion of a "precursor polymer" as defined herein into a "functionalized polymer" as defined herein.

As used herein, the term "hydrophilicity modifier" refers to a pendant group which is capable of changing the water solubility and/or hydrophilicity of a polymer to which the hydrophilicity modifier is bonded. Examples of pendant hydrophilicity modifiers include polyethyleneglycols (PEG), hydroxyl groups and hydroxyalkyl groups. "Hydroxyalkyl" means an alkyl group, as defined herein, to which one or more (such as one, two, three or four) hydroxy groups are attached.

As used herein, the term "alkyl" includes both saturated straight chain and branched alkyl groups. Preferably, an alkyl group is a C1-20 alkyl group, more preferably a C1-15, more preferably still a C1-10 alkyl group, more preferably still, a C1-5 alkyl group, and most preferably a C1-3 alkyl group such methyl. Particularly preferred alkyl groups include, for example, methyl, ethyl, propyl, isopropyl, butyl, isobutyl, tert-butyl, pentyl and hexyl. The term "alkylene" should be construed accordingly.

As used herein, the term "alkenyl" refers to a group containing one or more carbon-carbon double bonds, which may be branched or unbranched. Preferably the alkenyl group is a C2-20 alkenyl group, more preferably a C2-15 alkenyl group, more preferably still a C2-10 alkenyl group, or preferably a C2-5 alkenyl group, and most preferably a C2-3 alkenyl group. The term "alkenylene" should be construed accordingly.

As used herein, the term "alkynyl" refers to a carbon chain containing one or more triple bonds, which may be branched or unbranched. Preferably the alkynyl group is a C2-20 alkynyl group, more preferably a C2-15 alkynyl group, more preferably still a C2-10 alkynyl group, or preferably a C2-5 alkynyl group and most preferably a C2-3 alkynyl group. The term "alkynylene" should be construed accordingly.

As used herein, the term alkoxy refers to an alkyl group as defined herein that is attached to an oxygen atom.

As used herein, the term carbocyclyl includes a C3-7 carbocyclyl group, which is a non-aromatic saturated or unsaturated hydrocarbon ring having from 3 to 7 carbon atoms. Preferably it is a saturated or mono-unsaturated hydrocarbon ring (i.e. a cycloalkyl moiety or a cycloalkenyl moiety) having from 3 to 7 carbon atoms, more preferably having from 5 to 6 carbon atoms. Examples include cyclopropyl, cyclobutyl, cyclopentyl and cyclohexyl and their mono-unsaturated variants. Particularly preferred carbocyclic groups are cyclopentyl and cyclohexyl. The term "carbocyclylene" should be construed accordingly.

As used herein, the term "aryl" includes a C6-10 aryl, which is a monocyclic or polycyclic 6- to 10-membered aromatic hydrocarbon ring system having from 6 to 10 carbon atoms. Phenyl is preferred. The term "arylene" should be construed accordingly.

As used herein, the term "heterocyclyl" includes a 5- to 10-membered heterocyclyl group, which is a non-aromatic, saturated or unsaturated, monocyclic or polycyclic C5-10 carbocyclic ring system in which one or more, for example 1, 2, 3 or 4, of the carbon atoms are replaced with a moiety selected from N, O, S, S(O) and S(O)$_2$. Preferably, the 5- to 10-membered heterocyclyl group is a 5- to 6-membered ring. The term "heterocyclyene" should be construed accordingly.

Examples of heterocyclyl groups include azetidinyl, oxetanyl, thietanyl, pyrrolidinyl, imidazolidinyl, oxazolidinyl, isoxazolidinyl, thiazolidinyl, isothiazolidinyl, tetrahydrofuranyl, tetrahydrothienyl, tetrahydropyranyl, tetrahydrothiopyranyl, dithiolanyl, dioxolanyl, pyrazolidinyl, piperidinyl, piperazinyl, hexahydropyrimidinyl, methylenedioxyphenyl, ethylenedioxyphenyl, thiomorpholinyl, S-oxothiomorpholinyl, S,S-dioxo-thiomorpholinyl, morpholinyl, 1,3-dioxolanyl, 1,4-dioxolanyl, trioxolanyl, trithianyl, imidazolinyl, pyranyl, pyrazolinyl, thioxolanyl, thioxothiazolidinyl, 1H-pyrazol-5-(4H)-onyl, 1,3,4-thiadiazol-2(3H)-thionyl, oxopyrrolidinyl, oxothiazolidinyl, oxopyrazolidinyl, succinimido and maleimido groups and moieties. Preferred heterocyclyl groups are pyrrolidinyl, imidazolidinyl, oxazolidinyl, isoxazolidinyl, thiazolidinyl, isothiazolidinyl, tetrahydrofuranyl, tetrahydrothienyl, tetrahydropyranyl, tetrahydrothiopyranyl, dithiolanyl, dioxolanyl, pyrazolidinyl, piperidinyl, piperazinyl, hexahydropyrimidinyl, thiomorpholinyl and morpholinyl groups and moieties. More preferred heterocyclyl groups are tetrahydropyranyl, tetrahydrothiopyranyl, thiomorpholinyl, tetrahydrofuranyl, tetrahydrothienyl, piperidinyl, morpholinyl and pyrrolidinyl groups.

As used herein, the term "heteroaryl" includes a 5- to 10-membered heteroaryl group, which is a monocyclic or polycyclic 5- to 10-membered aromatic ring system, such as a 5- or 6-membered ring, containing at least one heteroatom, for example 1, 2, 3 or 4 heteroatoms, selected from 0, S and N. When the ring contains 4 heteroatoms these are preferably all nitrogen atoms. The term "heteroarylene" should be construed accordingly.

Examples of monocyclic heteroaryl groups include thienyl, furyl, pyrrolyl, imidazolyl, thiazolyl, isothiazolyl, pyrazolyl, oxazolyl, isoxazolyl, triazolyl, thiadiazolyl, oxadiazolyl, pyridinyl, pyridazinyl, pyrimidinyl, pyrazinyl, triazinyl and tetrazolyl groups.

Examples of polycyclic heteroaryl groups include benzothienyl, benzofuryl, benzimidazolyl, benzothiazolyl, benzisothiazolyl, benzoxazolyl, benzisoxazolyl, benztriazolyl, indolyl, isoindolyl and indazolyl groups. Preferred polycyclic groups include indolyl, isoindolyl, benzimidazolyl, indazolyl, benzofuryl, benzothienyl, benzoxazolyl, benzisoxazolyl, benzothiazolyl and benzisothiazolyl groups, more preferably benzimidazolyl, benzoxazolyl and benzothiazolyl, most preferably benzothiazolyl. However, monocyclic heteroaryl groups are preferred.

Preferably the heteroaryl group is a 5- to 6-membered heteroaryl group. Particularly preferred heteroaryl groups are thienyl, pyrrolyl, imidazolyl, thiazolyl, isothiazolyl, pyrazolyl, oxazolyl, isoxazolyl, triazolyl, pyridinyl, pyridazinyl, pyrimidinyl and pyrazinyl groups. More preferred groups are thienyl, pyridinyl, pyridazinyl, pyrimidinyl, pyrazinyl, pyrrolyl and triazinyl, triazolyl, most preferably triazolyl. The term "triazolyl" is herein used interchangeably with "triazole" and, unless explicitly indicated to the contrary, refers to a 1,2,3-triazole.

As used herein, the term "optionally substituted" in the context of optionally substituted alkyl, optionally substituted alkenyl, optionally substituted alkynyl, optionally substituted alkoxy, optionally substituted carbocyclyl, optionally substituted aryl, optionally substituted heterocyclyl, and optionally substituted heteroaryl means "unsubstituted or substituted". "Substituted" means that one or more hydrogen atoms are replaced by substituents selected from halogen atoms and hydroxyl, —NH$_2$ and sulfonic acid groups. Typically from 1 to 10 hydrogen atoms are replaced, more preferably 1 to 5, more preferably still 1, 2 or 3 and most preferably 1 or 2, for example 1. Preferably any given "substituted" group carries not more than 2 sulfonic acid substituents. Halogen atoms are preferred substituents. Preferably, though, the optionally substituted alkyl, optionally substituted alkenyl, optionally substituted alkynyl, optionally substituted alkoxy, optionally substituted carbocyclyl, optionally substituted aryl, optionally substituted heterocyclyl, and optionally substituted heteroaryl are unsubstituted.

As used herein, the term "pharmaceutically active agent" means an agent, e.g., a protein, peptide, nucleic acid (including nucleotides, nucleosides and analogues thereof) or small molecule drug, that provides a desired pharmacological effect upon administration to a subject, e.g., a human or a non-human animal, either alone or in combination with other active or inert components. Included in the above definition are precursors, derivatives, analogues and prodrugs of pharmaceutically active agents.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid," "nucleic acid molecule", "oligonucleotide" and "polynucleotide" are used interchangeably and refer to a polymeric form of nucleotides of any length, either deoxyribonucleotides or ribonucleotides, or compounds produced synthetically which can hybridize with naturally occurring nucleic acids in a sequence specific manner similar to that of two naturally occurring nucleic acids, e.g., can participate in Watson-Crick base pairing interactions. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, cDNA, recombinant polynucleotides, plasm ids, vectors, isolated DNA of any sequence, control regions, isolated RNA of any sequence, nucleic acid probes, and primers.

As used herein "bioavailability" refers to the fraction of the pharmaceutically active agent dose that enters the systemic circulation following administration.

As used herein, the terms "Glucagon-like-peptide-1" and "GLP-1" refer to a molecule having GLP-1 activity. One of ordinary skill in the art can determine whether any given moiety has GLP-1 activity, as disclosed in U.S. Published Application No. 2010/0210505, which is incorporated herein by reference. The term "GLP-1" includes native GLP-1 (GLP-1 (7-37)OH or GLP-1 (7-36)NH2), GLP-1 analogs, GLP-1 derivatives, GLP-1 biologically active fragments, extended GLP-1 (see, for example, International Patent Publication No. WO 03/058203, which is incorporated herein by reference, in particular with respect to the extended glucagon-like peptide-1 analogs described therein), exendin-4, exendin-4 analogs, and exendin-4 derivatives comprising one or two cysteine residues at particular positions as described in WO 2004/093823, which is incorporated herein by reference.

When used to characterize a vehicle component or components as described herein, the term "% w/w" refers to % by weight.

The term "click chemistry" comprises and identifies various groups of chemical reactions characterized by particular properties such as rapidity, regioselectivity and high yield and having a high thermodynamic driving force. Among "click" reactions, cycloaddition reactions such as Diels-Alder reactions, and above all Huisgen 1,3-dipolar cycloadditions, are particularly significant in the present invention. An example of a cycloaddition consists of a reaction in which two unsaturated molecules react to form a cyclic compound with the formation of two new a bonds using π electrons.

As used herein, "cycloaddition" refers to a chemical reaction in which two or more π (pi)-electron systems (e.g., unsaturated molecules or unsaturated parts of the same molecule) combine to form a cyclic product in which there is a net reduction of the bond multiplicity. In a cycloaddition, the π (pi) electrons are used to form new sigma (σ) bonds. The product of a cycloaddition is called an "adduct" or "cycloadduct". Different types of cycloadditions are known in the art including, but not limited to, [3+2] cycloadditions and Diels-Alder reactions. [3+2] cycloadditions, which are also called 1,3-dipolar cycloadditions, occur between a 1,3-dipole and a dipolarophile and are typically used for the construction of five-membered heterocyclic rings. The term "[3+2] cycloaddition" also encompasses "copperless" [3+2] cycloadditions between azides and cyclooctynes and difluorocyclooctynes described by Bertozzi et al. *J. Am. Chem. Soc.*, 2004, 126: 15046-15047.

A variety of methods are known in the art for determining the molecular weight of a polymer. Gel permeation chromatography may be utilized to determine molecular weight as weight average molecular weight (Mw). In addition, number average molecular weight (Mn) may be calculated from $^1$H NMR spectra. A suitable method may be selected at least in part based on the approximate molecular weight of the polymer. For example, determination of molecular weight from NMR spectra may be suitable where the molecular weight of the polymer is less than about 45 kDa, while gel permeation chromatography may be suitable for polymers having a molecular weight of greater than about 45 kDa.

An exemplary "gel permeation chromatography" (GPC) method utilizing an Agilent 1100 series liquid chromatography system is described below. The system includes a pump, a solvent degasser, an automated injector, a column oven, and a differential refractive index detector. Agilent Mixed D columns are used with polystyrene calibration standards. Tetrahydrofuran is used as the eluent. Both the columns and the detector are maintained at 30° C. Calibration and calculation of polymer molecular weights are accomplished using the Chemstation® software.

The GPC method parameters are generally as follows:

Instrumentation: Agilent 1100 Series LC, equipped with a refractive index (RI) detector and solvent degasser.

Column Set: Agilent Mixed D® columns, 300×7.5 mm, Part No. PL1110-6504, two columns in series.

Eluent: 100% THF, stabilized, B&J Honeywell Cat. No. 341-4.

Calibrants: Agilent polystyrene EasiCal PS 2 standards, Part No. PL12010-0601, concentration 0.10% w/v Sample Preparation: Weigh 0.045 to 0.055 grams of sample into a 20 mL vial and add 10 mL of THF (0.45-0.55% (w/v))

Instrument Conditions:
System Temperature: 30° C.
RI Detector: Polarity=positive
Flow rate: 1.0 mL/min
Injection Volume: 50 μL
Run Time: 25 min.

As discussed above, molecular weights (Mn) may be calculated using "NMR." As an example, the spectra are obtained on a Bruker NMR spectrometer operating at 300 MHz. Mn is calculated from the integrations of resonances assigned to polymer repeat units and polymer end groups. A sample calculation for a simple poly(DL-lactide-co-glycolide) is shown below. Values of Mn for polymer and copolymers of α-chloro-ε-caprolactone can be calculated in a similar fashion.

The number of repeat units of DL-lactide (x), the number of repeat units of glycolide (y) and the value of the degree of polymerization (DP), and the value of Mn from x and y are calculated from resonances assigned to polymer repeat units and polymer end groups. The structure below shows, the NMR assignments for the copolymer.

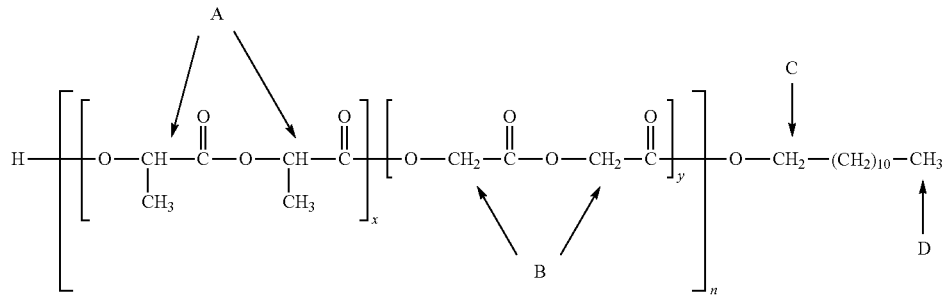

A=Intensity of 2 protons for Lactide Polymer (PLA) at 5.2 ppm
B=Intensity of 4 protons for Glycolide Polymer (PGY) at 4.95 ppm
C=Intensity of 2 (OCH2) protons for the 1-dodecanol end group between 4.0 and 4.2 ppm
D=Intensity of 3 (CH3) protons for the 1-dodecanol end group between 0.80 and 0.95 ppm The values of x, y, DP, and Mn are calculated using the values of the integrals from the NMR spectrum, A, B, and C:

$$x=(A/2)/(C/2)=A/C$$

$$y=(B/4)/(C/2)=B/2C$$

$$DP=x+y$$

$$Mn(Da)=144.13*x+116.07*y+186.34$$

where 144.13 is the formula weight of DL-lactide in grams per mole, 116.07 is the formula weight of glycolide in grams per mole, and 186.34 is the formula weight of the 1-dodecanol residue in grams per mole.

Calculation of x, y, DP, and Mn using A, B, and D:

$$x=(A/2)/(D/3)$$

$$y=(B/4)/(D/3)$$

$$DP=x+y$$

$$Mn(Da)=144.13*x+116.07*y+186.34$$

where 144.13 is the formula weight of DL-lactide in grams per mole, 116.07 is the formula weight of glycolide in grams per mole, and 186.34 is the formula weight of the 1-dodecanol residue in grams per mole.

As used herein, the term "zero shear viscosity" means viscosity at zero shear rate. A skilled artisan would be able to determine zero shear viscosity by measuring viscosity at low shear rate (e.g., around 1 $sec^{-1}$ to 7 $sec^{-1}$) using a plate and cone viscometer (e.g., Brookfield Model DV-III+(LV)) and then extrapolating a plot of viscosity versus shear rate to a shear rate of zero at a temperature of interest.

Before the present invention is further described, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

To the extent the disclosure or the definition or usage of any term herein conflicts with the disclosure or the definition or usage of any term in an application or publication incorporated by reference herein, the instant application shall control.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As an overview, the present disclosure relates to complexes including a pharmaceutically active agent and a functionalized polymer, wherein the functionalized polymer includes repeat units, the repeat units including ionizable repeat units including at least one ionizable side group, a plurality of the at least one ionizable side groups forming a plurality of non-covalent bonds with the pharmaceutically active agent. Among the preferred embodiments of the present disclosure are embodiments in which at least 10% of the repeat units include at least one ionizable side group.

The present disclosure also provides complexes including a pharmaceutically active agent and a functionalized polymer, the functionalized polymer including repeat units, the functionalized polymer including at least one of: (a) ionizable repeat units including at least one ionizable side group, wherein the at least one ionizable side group includes at least one member selected from ammonium, carboxylate, hydrazinium, guanidinium, sulfate, sulfonate, and phosphate; and (b) at least one ionizable end group.

The present disclosure also provides compositions including a vehicle and complexes including a pharmaceutically active agent and a functionalized polymer complexed with the pharmaceutically active agent through non-covalent bonding.

The present disclosure also provides methods including the steps of: providing a precursor polymer comprising repeat units, the repeat units comprising functionalizable repeat units comprising at least one functionalizable side group; obtaining a functionalized polymer by transforming, using click chemistry, said functionalizable repeat units into ionizable repeat units comprising at least one ionizable side group; and combining the functionalized polymer with a pharmaceutically active agent to form a complex in which a plurality of the at least one ionizable side groups form a plurality of non-covalent bonds with the pharmaceutically active agent.

The present disclosure also provides methods including the steps of: combining a functionalized polymer with a pharmaceutically active agent, the functionalized polymer comprising ionizable repeat units comprising at least one ionizable side group, to form a complex in which a plurality of the at least one ionizable side groups form a plurality of non-covalent bonds with the pharmaceutically active agent.

Additional information related to the disclosure outlined above is now provided.

Complexes

The complexes of the present disclosure may be formed based on non-covalent interaction (e.g., electrostatic, steric, hydrogen bonding, and van der Waals interactions) between a functionalized polymer including ionizable repeat units and/or ionizable end groups as described herein and a pharmaceutically active agent. The complex may be a salt. Ideally, the complex reduces the solubility of the pharmaceutically active agent in the depot and/or in the body to prolong drug release. The complex may also increase the stability of the pharmaceutically active agent, e.g., the radiation stability of the pharmaceutically active agent, either alone or when present in a depot. In addition to reducing the solubility, the complex achieves a vastly increased molecular weight such that its diffusion coefficient is reduced to slow movement of the pharmaceutically active agent. The solubility of the complex and its mobility in the environment can be further modulated by the molecular weight of the complexing polymer and the hydrophilic/hydrophobic nature of the polymer.

In some embodiments, the complex has a solubility of less than 0.01 mg/mL in water at 25° C. at pH 7.4.

Functionalized Polymers for Complexes

To form the complexes of the present disclosure, functionalized polymers having positively or negatively charged groups (or ionizable groups which may be ionized to positively or negatively charged groups) are provided. Functionalized polymers having positively charged groups (or ionizable groups which may be ionized to positively charged groups) are generally used to form complexes with negatively charged pharmaceutically active agents and functionalized polymers having negatively charged groups (or ionizable groups which may be ionized to negatively charged groups) are generally used to form complexes with positively charged pharmaceutically active agents. Thus, in some embodiments the functionalized polymer has a net positive charge (or is ionizable to provide a net positive charge). In other embodiments, the functionalized polymer has a net negative charge (or is ionizable to provide a net negative charge). In some embodiments, the at least one ionizable side group is covalently bound to a precursor or intermediate polymer through click chemistry to provide the functionalized polymer, for example the at least one ionizable side group is covalently bound to the precursor or intermediate polymer through click chemistry catalyzed with copper to provide the functionalized polymer.

In some embodiments, the ionizable repeat units of the functionalized polymer comprise one or more ionizable side groups that comprise an optionally substituted heteroarylene ring, for example a 1,2,3-triazole ring.

In some embodiments, the functionalized polymer functionalized with ionizable groups is hydrophilic or water soluble. For instance, the functionalized polymer may have a water solubility ranging from 0.001 mg/mL to 1000 mg/mL at 25° C. and pH 7.4, such as 0.01 mg/mL to 100 mg/mL, 0.1 mg/mL to 10 mg/mL, or 1 mg/mL to 5 mg/m L. In some embodiments the functionalized polymer is biodegradable.

In some embodiments, the functionalized polymer is a polyester. Methods for producing polyesters are well known in the art. The functionalized polymers may include at least one repeat unit derived from a monomer selected from caprolactone, lactic acid, glycolic acid, lactide, glycolide, vinyl pyrrolidone, butyrolactone, and valerolactone, as well as derivatives of these monomers that: (a) comprise ionizable side groups; and/or (b) comprise functionalizable side groups that can be transformed into ionizable side groups after polymerization has been effected (e.g. alpha-chlorocaprolactone). In some embodiments, the functionalized polymer is not derived from amino acid monomers. Thus, in some embodiments, the functionalized polymer is not a polyamino acid.

Examples of ionizable side groups include, but are not limited to, ammonium, carboxylate, hydrazinium, guanidinium, sulfate, sulfonate, phosphonate and phosphate.

The percentage of repeat units making up a functionalized polymer which include at least one ionizable side group may vary. For example, the percentage of repeat units making up a functionalized polymer and which include at least one ionizable side group may be 100%, 50%, 25%, or 12.5%. The percentage of repeat units making up a functionalized polymer and which include at least one ionizable side group may range from 10% to 90%, such as 20% to 80%, 30% to 70%, or 40% to 60%.

Accordingly, in some embodiments a complex according to the present disclosure, prepared using functionalized polymers such as those described herein, includes a functionalized polymer, the functionalized polymer including repeat units, the repeat units including ionizable repeat units including at least one ionizable side group, a plurality of the at least one ionizable side groups forming a plurality of non-covalent bonds with the pharmaceutically active agent, wherein at least 10% of the repeat units comprise at least one ionizable side group, e.g., at least 20%, at least 30%, at least 40%, at least 50%, at least 60%, at least 70%, at least 80% or at least 90%.

In some embodiments, less than 100% of the repeat units comprise at least one ionizable side group. In some embodiments, the % of the repeat units comprising at least one ionizable side group ranges from 10% to 90%, e.g., 20% to 80%, 30% to 70%, or 40% to 60%. In some embodiments, the % of the repeat units comprising at least one ionizable side group ranges from 10% to 20%, 20% to 30%, 30% to 40%, 40% to 50%, 50% to 60%, 60% to 70%, 70% to 80%, 80% to 90%, or 90% to 100%.

The weight average molecular weight of the functionalized polymers is not particularly limited and may range for example from 1000 Daltons to 200,000 Daltons, as measured by gel permeation chromatography, e.g., from 2000 Daltons to 50,000 Daltons, from 1000 Daltons to 100,000 Daltons, from 1000 Daltons to 50,000 Daltons, from 1000 Daltons to 40,000 Daltons, from 1000 Daltons to 30,000 Daltons, from 1000 Daltons to 25,000 Daltons, from 1000 Daltons to 20,000 Daltons, from 1000 Daltons to 10,000 Daltons, or from 1000 Daltons to 5000 Daltons.

In some embodiments, the functionalized polymer has a weight average molecular weight ranging from 100,000 Daltons to 200,000 Daltons, from 50,000 Daltons to 200,000 Daltons, from 10,000 Daltons to 200,000 Daltons, or from 5,000 Daltons to 200,000 Daltons, as measured by gel permeation chromatography.

In some embodiments, the functionalized polymer has a number average molecular weight ranging from 5000 Daltons to 45,000 Daltons, as measured by NMR spectroscopy, e.g., from 10,000 Daltons to 45,000 Daltons, from 20,000 Daltons to 45,000 Daltons, or from 30,000 Daltons to 45,000 Daltons. In some embodiments, the functionalized polymer has a number average molecular weight ranging from 10,000 Daltons to 20,000 Daltons, or from 20,000 Daltons to 30,000 Daltons, as measured by NMR spectroscopy.

In some embodiments, the repeat units making up the functionalized polymer comprise repeat units comprising at least one pendant hydrophilicity modifier. Examples of these pendant hydrophilicity modifiers include, but are not limited to, polyethyleneglycols (PEG), hydroxyl groups, and hydroxyalkyl groups.

In some embodiments, the functionalized polymer comprises at least one ionizable end group, for example the functionalized polymer may comprise ionizable end groups at each of its ends. Examples of suitable ionizable end groups include ammonium, carboxylate, hydrazinium, guanidinium, sulfate, sulfonate, phosphonate and phosphate.

In some embodiments, the repeat units comprise repeat units of the formula (I):

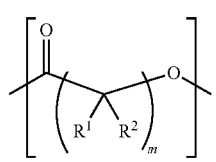

(I)

wherein
    m is an integer from 1 to 10, and
    each $R^1$ and $R^2$ is independently selected from hydrogen, hydroxyl, optionally substituted alkyl, optionally substituted alkenyl, optionally substituted alkynyl, optionally substituted alkoxy, optionally substituted carbocyclyl, optionally substituted aryl, optionally substituted heterocyclyl, optionally substituted heteroaryl, and a ionizable side group.

The repeat units may, for example, comprise repeat units of the formula (I) wherein each $R^1$ and $R^2$ is independently selected from hydrogen, $C_{1-5}$ alkyl and a ionizable side group. The repeat units may comprise repeat units of the formula (I) wherein m is an integer from 1 to 5. The repeat units may comprise repeat units of the formula (I) wherein one of the $R^1$ and $R^2$s is a ionizable side group and all of the remaining $R^1$ and $R^2$s are not ionizable side groups. The repeat units may comprise repeat units of the formula (I) wherein m is 5, one $R^1$ is a ionizable side group and all of the remaining $R^1$ and $R^2$s are hydrogen. Such repeat units can readily be provided using the methods described herein by using a caprolactone derivative as a monomer when preparing the functionalized polymer.

The ionizable side group in the formula (I) may comprise a positively charged side group or a negatively charged side group (or a side group which ionizes to a positively charged or negatively charged side group). For example, the charged side group may comprise ammonium, carboxylate, hydrazinium, guanidinium, sulfate, sulfonate, phosphonate and phosphate.

The ionizable side group in the formula (I) may comprise an optionally substituted heteroarylene ring. For example, the ionizable side group may have the formula (II):

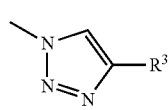

(II)

wherein $R^3$ comprises a ionizable functional group. $R^3$ may comprise at least one selected from ammonium, carboxylate, guanidinium, sulfate, phosphonate and phosphate, either attached directly to the ring or via a linker group.

Further examples of repeat units of the formula (I), one or more of which may be present in the functionalized polymer, include: repeat units wherein m is 5 and all of the $R^1$ and $R^2$s are hydrogen; repeat units wherein m is 1, $R^1$ is hydrogen and $R^2$ is hydrogen; repeat units wherein m is 1, $R^1$ is methyl and $R^2$ is hydrogen; repeat units wherein m is 2, the $R^1$ and $R^2$ alpha to the carbonyl group are each hydrogen, the $R^1$ beta to the carbonyl group is methyl and the $R^2$ beta to the carbonyl group is hydrogen; repeat units wherein m is 3 and all of the $R^1$ and $R^2$s are hydrogen; repeat units wherein m is 4, and all of the $R^1$ and $R^2$s are hydrogen; and repeat units wherein m is 3, the $R^1$ and $R^2$ alpha to the carbonyl group are each hydrogen, the $R^1$ and $R^2$ beta to the carbonyl group are each hydrogen, and the $R^1$ gamma to the carbonyl group is methyl and the $R^2$ gamma to the carbonyl group is hydrogen. Such repeat units can readily be provided using the methods described herein by using caprolactone, glycolic acid or glycolide, lactic acid or lactide, butyrolactone (e.g., beta-butyrolactone, gamma-butyrolactone, etc.) and valerolactone (e.g., delta-valerolactone, gamma-valerolactone, etc.), or derivatives therefore, respectively as monomers when preparing the functionalized polymer. By "alpha" is meant the first position from a designated carbon in an organic chemical structure at which an atom or a radical may be substituted. By "beta" is meant the second position from a designated carbon in an organic chemical structure at which an atom or a radical may be substituted. By "gamma" is meant the third position from a designated carbon in an organic chemical structure at which an atom or a radical may be substituted. By "delta" is meant the fourth position from a designated carbon in an organic chemical structure at which an atom or a radical may be substituted.

In some embodiments, the functionalized polymer is a homopolymer of repeat units of formula (I). Alternatively, the functionalized polymer is a copolymer comprising at least two different repeat units. For example, each of the at least two different repeat units in copolymer may be of formula (I) (but with different m, $R^1$ and/or $R^2$s).

In some embodiments, the functionalized polymer includes one or more repeat units. For example, the functionalized polymer may include 1 to 10 repeat units, such as 1 to 7 repeat units, including 1 to 5 repeat units, or 1 to 3 repeat units. In some instances, the functionalized polymer includes 1 to 3 repeat units, such as 1 repeat unit, 2 repeat units or 3 repeat units. The repeat units may be any of the repeat units as described herein. Embodiments that include 1 repeat unit may also be referred to as monomers rather than a polymer. In some instances, the functionalized polymer may include repeat units where each repeat unit is of the same formula, e.g., a homopolymer of the same repeat unit. For example, the functionalized polymer may include 2 repeat units where each repeat unit is of the same formula. In some instances, the functionalized polymer includes 3 repeat units where each repeat unit is of the same formula. In other embodiments, the functionalized polymer is a copolymer that includes at least two different repeat units. For instance, the functionalized polymer may include 2 repeat units, where the repeat units are different repeat units. In some cases, the functionalized polymer incldues 3 repeat units, where two repeat units are of the same formula and the third repeat unit is of a different formula. In some instances, the functionalized polymer includes 3 repeat units where each repeat unit is of a different formula. In embodiments that includes repeat units with different formulae, different arrangements (i.e., permutations) of the repeat units are possible. For example, in embodiments that include 2 repeat units with different formula (e.g., repeat unit 1 and repeat unit 2), the 2 repeat units may be arranged in the polymer as: (repeat unit 1)-(repeat unit 2); or (repeat unit 2)-(repeat unit 1). Similarly, in embodiments that include 3 repeat units where two repeat units are of the same formula and the third repeat unit is of a different formula (e.g., repeat unit 1, repeat unit 1 and repeat unit 2; or repeat unit 1, repeat unit 2 and repeat unit 2), the 3 repeat units may be arranged in the polymer in one of 6 different permutations:

(repeat unit 1)-(repeat unit 1)-(repeat unit 2);
(repeat unit 1)-(repeat unit 2)-(repeat unit 1);
(repeat unit 2)-(repeat unit 1)-(repeat unit 1);
(repeat unit 1)-(repeat unit 2)-(repeat unit 2);
(repeat unit 2)-(repeat unit 1)-(repeat unit 2); or
(repeat unit 2)-(repeat unit 2)-(repeat unit 1).

Similarly, in embodiments that include 3 repeat units where each repeat unit is of a different formula (e.g., repeat unit 1, repeat unit 2 and repeat unit 3, the 3 repeat units may be arranged in the polymer in one of 6 different permutations:

(repeat unit 1)-(repeat unit 2)-(repeat unit 3);
(repeat unit 1)-(repeat unit 3)-(repeat unit 2);
(repeat unit 2)-(repeat unit 1)-(repeat unit 3);
(repeat unit 2)-(repeat unit 3)-(repeat unit 1);
(repeat unit 3)-(repeat unit 1)-(repeat unit 2); or
(repeat unit 3)-(repeat unit 2)-(repeat unit 1).

The repeat units in the examples above (e.g., repeat unit 1, repeat unit 2 and repeat unit 3) may be any of the repeat units as described herein. In certain embodiments, the functionalized polymer includes an optional ionizable group between the repeat units, such that a repeat unit is linked to an adjacent repeat unit through a linking ionizable unit. In these instances, the optional linking ionizable unit may be selected from ammonium, carboxylate, hydrazinium, guanidinium, sulfate, sulfonate, phosphonate and phosphate.

An example of a functionalized polymer is poly(ε-caprolactone) (PCL) with amine pendant groups capable of complexing with a pharmaceutically active agent (shown below in salt form):

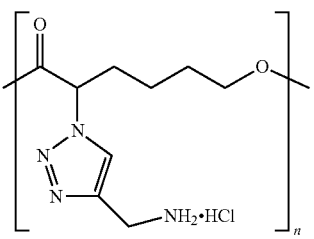

Another example of a functionalized polymer is PCL copolymer with amine pendant groups on a certain fraction of the repeat units capable of complexing with a pharmaceutically active agent (shown below in salt form):

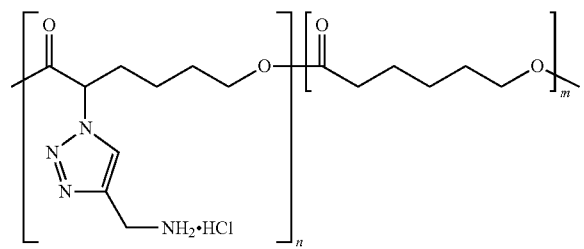

While the immediately preceding structure depicts a block copolymer structure, it should be understood that, as with other block copolymer structures described herein, the repeat units may alternatively be randomly distributed in the polymer.

Yet another example of a functionalized polymer is poly(ε-caprolactone) (PCL) with carboxylate pendant groups capable of complexing with a pharmaceutically active agent (shown below in salt form):

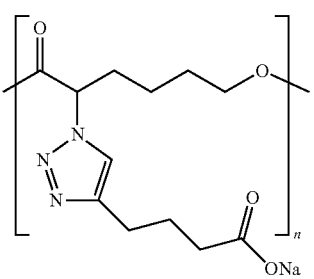

A further example of a functionalized polymer is poly(ε-caprolactone) (PCL) with guanidinium pendant groups capable of complexing with a pharmaceutically active agent (shown below in salt form):

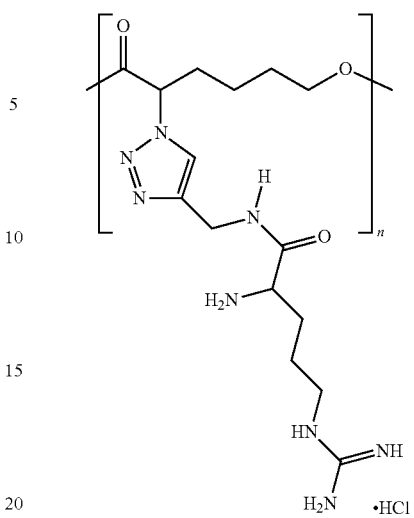

Pharmaceutically Active Agents for Complexes

A wide variety of pharmaceutically active agents may be utilized in the complexes and compositions described herein, including, but not limited to, peptides, proteins, and small molecules, e.g., small molecules having a molecular weight less than 500 Daltons.

General classes of pharmaceutically active agents which may be utilized include, for example, proteins, peptides, nucleic acids, nucleotides, nucleosides and analogues thereof, antigens, antibodies, and vaccines; as well as low molecular weight compounds.

Pharmaceutically active agents which may be utilized in the complexes and compositions disclosed herein include, but are not limited to, agents which act on the peripheral nerves, adrenergic receptors, cholinergic receptors, the skeletal muscles, the cardiovascular system, smooth muscles, the blood circulatory system, synaptic sites, neuroeffector junction sites, endocrine and hormone systems, the immunological system, the reproductive system, the skeletal system, autacoid systems, the alimentary and excretory systems, the histamine system and the central nervous system.

Suitable pharmaceutically active agents may be selected, for example, from chemotherapeutic agents, epigenetic agents, proteasome inhibitors, adjuvant drugs, anti-emetics, appetite stimulants, anti-wasting agents and high potency opioids.

Suitable pharmaceutically active agents may also be selected, for example, from anti-neoplastic agents, cardiovascular agents, renal agents, gastrointestinal agents, rheumatologic agents and neurological agents among others.

Protein, Polypeptides and Peptides as Pharmaceutically Active Agents:

Proteins useful in the disclosed complexes and compositions may include, for example, molecules such as cytokines and their receptors, as well as chimeric proteins comprising cytokines or their receptors, including, for example tumor necrosis factor alpha and beta, their receptors and their derivatives; renin; growth hormones, including human growth hormone (e.g., rhGH), bovine growth hormone, methione-human growth hormone, des-phenylalanine human growth hormone, and porcine growth hormone; growth hormone releasing factor (GRF); octreotide, parathyroid and pituitary hormones; thyroid stimulating hormone; human pancreas hormone releasing factor; lipoproteins; colchicine; prolactin; corticotrophin; thyrotropic hormone; oxytocin; vasopressin; somatostatin; lypressin; pancreozym in; leuprolide; alpha-1-antitrypsin; insulin; insulin analogs; insulin derivatives; insulin prodrugs; glargine; insulin A-chain; insulin B-chain; proinsulin; follicle stimulating hormone; calcitonin; luteinizing hormone; luteinizing hormone releasing hormone (LHRH); LHRH agonists and antagonists; glucagon; clotting factors such as factor VIIIC, factor IX, tissue factor, and von Willebrands factor; anti-clotting factors such as Protein C; atrial natriuretic factor; lung surfactant; a plasminogen activator other than a tissue-type plasminogen activator (t-PA), for example a urokinase; bombesin; thrombin; hemopoietic growth factor; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; chorionic gonadotropin; gonadotropin releasing hormone; bovine somatotropin; porcine somatotropin; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as acidic FGF and basic FGF; epidermal growth factor (EGF); transforming growth factor (TGF) such as TGF-alpha and TGF-beta, including TGF-β-1, TGF-β-2, TGF-β-3, TGF-β-4, or TGF-β-5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha (e.g., interferonα2A or interferonα2B), -beta, -gamma, -lambda and consensus interferon; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV-1 envelope glycoprotein, gp120, gp160 or fragments thereof; transport proteins; homing receptors; addressins; fertility inhibitors such as the prostaglandins; fertility promoters; regulatory proteins; antibodies and chimeric proteins, such as immunoadhesins; precursors, derivatives, prodrugs and analogues of these compounds, and pharmaceutically acceptable salts of these compounds, or their precursors, derivatives, prodrugs and analogues.

Suitable proteins or peptides may be native or recombinant and include, e.g., fusion proteins.

In some embodiments, the protein is a growth hormone, such as human growth hormone (hGH), recombinant human growth hormone (rhGH), bovine growth hormone, methione-human growth hormone, des-phenylalanine human growth hormone, and porcine growth hormone; insulin, insulin A-chain, insulin B-chain, and proinsulin; or a growth factor, such as vascular endothelial growth factor (VEGF), nerve growth factor (NGF), platelet-derived growth factor (PDGF), fibroblast growth factor (FGF), epidermal growth factor (EGF), transforming growth factor (TGF), and insulin-like growth factor-I and -II (IGF-I and IGF-II).

Suitable peptides for use as the complexes and compositions disclosed herein include, but are not limited to, exenatide and Glucagon-like peptide-1 (GLP-1) and precursors, derivatives, prodrugs and analogues thereof. For instance, the peptide may be one or more of liraglutide, lixisenatide, albiglutide, dulaglutide, CJC-1134-PC, ACP-03, and semaglutide.

Nucleic Acids as Pharmaceutically Active Agents: Nucleic acid pharmaceutically active agents include nucleic acids as well as precursors, derivatives, prodrugs and analogues thereof, e.g., therapeutic nucleotides, nucleosides and analogues thereof; therapeutic oligonucleotides; and therapeutic polynucleotides. Pharmaceutically active agents selected from this group may find particular use as anticancer agents and antivirals. Suitable nucleic acid pharmaceutically active agents may include for example ribozymes, antisense oligodeoxynucleotides, aptamers and siRNA. Examples of suitable nucleoside analogues include, but are not limited to, cytarabine (araCTP), gemcitabine (dFdCTP), and floxuridine (FdUTP).

Other Pharmaceutically Active Agents: A variety of other pharmaceutically active agents may be used in the compositions disclosed herein. Suitable compounds may include, but are not limited to, compounds directed to one or more of the following drug targets: Kringle domain, Carboxypeptidase, Carboxylic ester hydrolases, Glycosylases, Rhodopsin-like dopamine receptors, Rhodopsin-like adrenoceptors, Rhodopsin-like histamine receptors, Rhodopsin-like serotonin receptors, Rhodopsin-like short peptide receptors, Rhodopsin-like acetylcholine receptors, Rhodopsin-like nucleotide-like receptors, Rhodopsin-like lipid-like ligand receptors, Rhodopsin-like melatonin receptors, Metalloprotease, Transporter ATPase, Carboxylic ester hydrolases, Peroxidase, Lipoxygenase, DOPA decarboxylase, A/G cyclase, Methyltransferases, Sulphonylurea receptors, other transporters (e.g., Dopamine transporter, GABA transporter 1, Norepinephrine transporter, Potassium-transporting ATPase α-chain 1, Sodium-(potassium)-chloride cotransporter 2, Serotonin transporter, Synaptic vesicular amine transporter, and Thiazide-sensitive sodium-chloride cotransporter), Electrochemical nucleoside transporter, Voltage-gated ion channels, GABA receptors (Cys-Loop), Acetylcholine receptors (Cys-Loop), NMDA receptors, 5-HT3 receptors (Cys-Loop), Ligand-gated ion channels Glu: kainite, AMPA Glu receptors, Acid-sensing ion channels aldosterone, Ryanodine receptors, Vitamin K epoxide reductase, Met-GluR-like GABA$_B$ receptors, Inwardly rectifying K$^+$ channel, NPC1L1, MetGluR-like calcium-sensing receptors, Aldehyde dehydrogenases, Tyrosine 3-hydroxylase, Aldose reductase, Xanthine dehydrogenase, Ribonucleoside reductase, Dihydrofolate reductase, IMP dehydrogenase, Thioredoxin reductase, Dioxygenase, Inositol monophosphatase, Phosphodiesterases, Adenosine deaminase, Peptidylprolyl isomerases, Thymidylate synthase, Aminotransferases, Farnesyl diphosphate synthase, Protein kinases, Carbonic anhydrase, Tubulins, Troponin, Inhibitor of IκB kinase-β, Amine oxidases, Cyclooxygenases, Cytochrome P450s, Thyroxine 5-deiodinase, Steroid dehydrogenase, HMG-CoA reductase, Steroid reductases, Dihydroorotate oxidase, Epoxide hydrolase, Transporter ATPase, Translocator, Glycosyltransferases, Nuclear receptors NR3 receptors, Nuclear receptors: NR1 receptors, and Topoisomerase.

In some embodiments, pharmaceutically active agent is a compound targeting one of rhodopsin-like GPCRs, nuclear receptors, ligand-gated ion channels, voltage-gated ion channels, penicillin-binding protein, myeloperoxidase-like, sodium: neurotransmitter symporter family, type II DNA topoisomerase, fibronectin type III, and cytochrome P450.

In some embodiments, the pharmaceutically active agent is an anticancer agent. Suitable anticancer agents include, but are not limited to, Actinomycin D, Alemtuzumab, Allopurinol sodium, Amifostine, Amsacrine, Anastrozole, Ara-CMP, Asparaginase, Azacytadine, Bendamustine, Bevacizumab, Bicalutimide, Bleomycin (e.g., Bleomycin $A_2$ and $B_2$), Bortezomib, Busulfan, Camptothecin sodium salt, Capecitabine, Carboplatin, Carmustine, Cetuximab, Chlorambucil, Cisplatin, Cladribine, Clofarabine, Cyclophosphamide, Cytarabine, Dacarbazine, Dactinomycin, Daunorubicin, Daunorubicin liposomal, Dacarbazine, Decitabine, Docetaxel, Doxorubicin, Doxorubicin liposomal, Epirubicin, Estramustine, Etoposide, Etoposide phosphate, Exemestane, Floxuridine, Fludarabine, Fluadarabine phosphate, 5-Fluorouracil, Fotemustine, Fulvestrant, Gemcitabine, Goserelin, Hexamethylmelamine, Hydroxyurea, Idarubicin, Ifosfamide, Imatinib, Irinotecan, Ixabepilone, Lapatinib, Letrozole, Leuprolide acetate, Lomustine, Mechlorethamine, Melphalan, 6-Mercaptopurine, Methotrexate, Mithramycin, Mitomycin C, Mitotane, Mitoxantrone, Nimustine, Ofatumumab, Oxaliplatin, Paclitaxel, Panitumumab, Pegaspargase, Pemetrexed, Pentostatin, Pertuzumab, Picoplatin, Pipobroman, Plerixafor, Procarbazine, Raltitrexed, Rituximab, Streptozocin, Temozolomide, Teniposide, 6-Thioguanine, Thiotepa, Topotecan, Trastuzumab, Treosulfan, Triethylenemelamine, Trimetrexate, Uracil Nitrogen Mustard, Valrubicin, Vinblastine, Vincristine, Vindesine, Vinorelbine, and analogues, precursors, derivatives and prodrugs thereof. It should be noted that two or more of the above compounds may be used in combination in the compositions of the present disclosure.

Pharmaceutically active agents of interest for use in the disclosed compositions may also include opioids and derivatives thereof as well as opioid receptor agonists and antagonists, e.g., methadone, naltrexone, naloxone, nalbuphine, fentanyl, sufentanil, oxycodone, oxymorphone, hydrocodone, hydromorphone, and pharmaceutically acceptable salts and derivatives thereof.

In some embodiments the pharmaceutically active agent is a low molecular weight compound, e.g., a compound having a molecular weight of less than or equal to about 800 Daltons, e.g., less than or equal to about 500 Daltons. In some embodiments, the pharmaceutically active agent is a compound having a molecular weight ranging from 800 Daltons to 100 Daltons, e.g., 700 Daltons to 200 Daltons, 600 Daltons to 300 Daltons, or 500 Daltons to 400 Daltons.

In some embodiments, the pharmaceutically active agent comprises at least one member selected from a peptide, protein, and small molecule, the small molecule having a molecular weight less than 500 Daltons.

The pharmaceutically active agent may contain one functional group that is capable of forming a non-covalent bond with the functionalized polymer. The pharmaceutically active agent may contain more than one functional group that is capable of forming non-covalent bonds with the functionalized polymer.

In some embodiments, the pharmaceutically active agent is stable in water. For instance, when the pharmaceutically active agent is placed in water at 25° C. for 1 hour, 12 hours, or 24 hours, the purity of the pharmaceutically active agent is degraded less than 5%, such as less than 3% or less than 2%.

The pharmaceutically active agent or pharmaceutically active agent complex may be present in any suitable concentration in the compositions disclosed herein. Suitable concentrations may vary depending on the potency of the pharmaceutically active agent, pharmacokinetic half-life, etc. For example, the pharmaceutically active agent may be present in a range of from about 1% to about 50% by weight of the composition, e.g., from about 5% to about 45%, from about 10% to about 40%, from about 15% to about 35%, or from about 20% to about 30% by weight of the composition. The complex including the pharmaceutically active agent may be present at a concentration ranging from about 10 mg/mL to about 500 mg/mL, such as from about 50 mg/mL to about 450 mg/mL, about 100 mg/mL to about 400 mg/mL, about 150 mg/mL to about 350 mg/mL, or about 200 mg/mL to about 300 mg/m L.

In some embodiments, the complex comprising the functionalized polymer and pharmaceutically active agent has a solubility of less than 0.01 mg/mL in water at 25° C. at pH 7.4.

In some embodiments, in the complex comprising the functionalized polymer and pharmaceutically active agent, the ratio of the amount of the pharmaceutically active agent to the amount of the functionalized polymer in the complex is from 1:1 to 1:10 by weight, e.g., from 1:1 to 1:9 by weight, from 1:1 to 1:8 by weight, from 1:1 to 1:7 by weight, from 1:1 to 1:6 by weight, from 1:1 to 1:5 by weight, from 1:1 to 1:4 by weight, from 1:1 to 1:3 by weight, or from 1:1 to 1:2 by weight. In some embodiments, in the complex comprising the functionalized polymer and pharmaceutically active agent, the ratio of the amount of the pharmaceutically active agent to the amount of the functionalized polymer in the complex is from 1:1 to 1:2 by weight, from 1:2 to 1:3 by weight, from 1:3 to 1:4 by weight, from 1:4 to 1:5 by weight, from 1:5 to 1:6 by weight, from 1:6 to 1:7 by weight, from 1:7 to 1:8 by weight, from 1:8 to 1:9 by weight, or from 1:9 to 1:10 by weight.

In one aspect, the complex may have a median particle size, as measured by laser diffraction, of less than 10 micrometers, such as less than 5 micrometers, less than 3 micrometers, less than 2 micrometers, or less than 1 micrometer. In some aspects, a process comprises milling the complex to achieve the desired particle size.

Pharmaceutical Compositions

The present disclosure provides pharmaceutical compositions including a vehicle and a complex, the complex including a pharmaceutically active agent and a functionalized polymer complexed with the pharmaceutically active agent through non-covalent bonding.

Polymers

In some embodiments, the amount of the functionalized polymer present in the composition is less than 50% by weight based on the total weight of the composition, e.g., less than 40%, less than 30%, less than 20%, less than 10%, or less than 5%.

In some embodiments, the amount of the functionalized polymer present in the composition ranges from 5% by weight to 50% by weight based on the total weight of the composition, e.g., 10% by weight to 40% by weight, or 20% by weight to 30% by weight.

In some embodiments, the amount of the functionalized polymer present in the composition ranges from 5% to 10% by weight based on the total weight of the composition, e.g., 10% by weight to 20% by weight, 20% by weight to 30% by weight, 30% by weight to 40% by weight, or 40% by weight to 50% by weight.

Vehicle Polymers: In some embodiments, the vehicle includes a "vehicle" polymer, e.g., a biocompatible and/or biodegradable polymer. As described herein, the term "vehicle" polymer is used to distinguish this component from the functionalized polymer comprised in the complex. The vehicle polymer is a polymer other than the functionalized polymer comprised in the complex. Suitable vehicle polymers may include, but are not limited to, homopolymers, block-copolymers and random copolymers. Suitable polymers include those polymers or combinations of polymers which have solubility of at least about 20 weight %, 30 weight %, or 40 weight % in a selected solvent or solvent combination. In some embodiments, suitable polymers include polymers having both hydrophilic and hydrophobic regions, e.g., an AB-type block copolymer composed of hydrophobic and hydrophilic components. Such polymers may have a tendency to form micelles when exposed to an aqueous environment as a result of the amphiphilic character of the polymer. Suitable polymers may include, but are not limited to, polylactides, polyglycolides, polycaprolactones, copolymers including any combination of two or more monomers involved in the above, e.g., terpolymers of lactide, glycolide and ε-caprolactone, and mixtures including any combination of two or more of the above. In other words, suitable polymers may also include, for example, polylactic acids, polyglycolic acids, polycaprolactones, copolymers including any combination of two or more monomers involved in the above, e.g., terpolymers of lactic acid, glycolic acid and ε-caprolactone, and mixtures including any combination of two or more of the above.

In some embodiments, a suitable vehicle polymer is polylactic acid (PLA), e.g., a PLA including an ionizable end-group (e.g., an acid end-group, e.g., in an acid-terminated PLA). Acid end-group PLAs include, e.g., lactate initiated PLAs described herein. In some embodiments, the PLA includes an unionizable end-group (e.g., an ester end-group, e.g., in an ester terminated PLA). Ester end-group PLAs include, but are not limited to, dodecanol-initiated (dd) PLAs described herein. In some embodiments, the PLA is DL-PLA. In other embodiments, the biodegradable polymer is poly(lactic-co-glycolic acid) (PLGA), e.g., dl-PLGA. In some embodiments, the PLGA includes an ionizable end-group, e.g., an acid end-group. Acid end-group PLGAs include, but are not limited to, the glycolate initiated (ga) PLGAs described herein. In some embodiments, the PLGA includes an unionizable end-group, e.g., an ester end group. Ester end-group PLGAs include, but are not limited to, dodecanol initiated PLGAs described herein. In one embodiment, where the polymer is a polycaprolactone, the polycaprolactone is poly(c)caprolactone.

The vehicle polymer may be present in the vehicle in an amount ranging from about 5% to about 40% by weight of the vehicle, for example, from about 6% to about 35%, from about 7% to about 30%, from about 8% to about 27%, from about 9% to about 26%, from about 10% to about 25%, from about 11% to about 24%, from about 12% to about 23%, from about 13% to about 22%, from about 14% to about 21%, from about 15% to about 20%, from about 16% to about 19%, or at about 17% by weight of the vehicle. In some embodiments, the polymer is present in an amount of about 20% by weight of the vehicle.

In some embodiments, the vehicle polymer has a weight average molecular weight of from about 2 kDa to about 20 kDa, e.g., from about 2 kDa to about 5 kDa, from about 2 kDa to about 10 kDa, or from about 2 kDa to about 15 kDa. Additional embodiments include a biocompatible, biodegradable polymer having a weight average molecular weight of from about 5 kDa to about 15 kDa, e.g., about 10 kDa, e.g., as determined by gel permeation chromatography or NMR spectroscopy.

In some embodiments, the pharmaceutical composition, which includes vehicle polymer, has a low amount of functionalized polymer. For instance, the amount of functionalized polymer in the pharmaceutical composition may be less than 50 wt %, such as less than 40 wt %, less than 30 wt %, less than 20 wt %, less than 10 wt % or less than 5 wt %, and may range from 5 wt % to 50 wt %, based on total weight of the pharmaceutical composition.

Also, the pharmaceutical composition may be free of polymer other than the functionalized polymer, e.g., free of vehicle polymer.

Solvents

Vehicle Solvents: In some embodiments the vehicle includes one or more solvents in addition to, or to the exclusion of, one or more vehicle polymers as discussed herein. In some embodiments, the solvent is present in the vehicle in an amount ranging from 60% to 100% by weight of the vehicle, e.g., from 70% to 100%, from 80% to 100% or from 90% to 100%.

In some embodiments, the solvent includes at least one hydrophilic/polar solvent. In addition to, or as an alternative to the at least one hydrophilic/polar solvent, the solvent may include at least one hydrophobic solvent.

In some embodiments, the solvent includes at least one member selected from water, a buffered aqueous system, dimethylsulfoxide (DMSO), benzyl alcohol (BA), benzyl benzoate (BB), hydrogenated castor oil, polyethoxylated castor oil, dimethylacetamide, ethanol, ethyl acetate, glycofurol, isopropyl myristate, ethyl benzoate, caprylic/capric triglyceride, n-methyl-pyrrolidone (NMP), propylene glycol monocaprylate, propylene carbonate, 2-pyrrolidone, triacetin, and triethyl citrate.

In some embodiments, the solvent is a benign vehicle solvent, such as an aqueous medium, BA, BB, DMSO, ethanol, ethyl acetate, glycofurol, propylene carbonate or NMP. The complexes may therefore improve injection site compatibility, which is sometimes an issue with drug depots.

A wide variety of vehicle solvents may be used. Water or buffered aqueous systems may suffice. Thus, the vehicle solvent may involve aqueous or non-aqueous systems comprising at least one of the following: dimethylsulfoxide (DMSO), benzyl alcohol (BA), benzyl benzoate (BB), Cremophor EL (polyethoxylated castor oil), dimethylacetamide, ethanol, ethyl acetate, glycofurol, isopropyl myristate, ethyl benzoate, Miglyol 810 (caprylic/capric triglyceride), n-methyl-pyrrolidone, Capryol 90 (propylene glycol monocaprylate), propylene carbonate, 2-pyrrolidone, triacetin, and triethyl citrate.

In some embodiments, the pharmaceutical composition is free of organic solvent. In other embodiments the pharmaceutical composition has a relatively low amount of organic solvent. For instance, the amount of organic solvent in the pharmaceutical composition may be less than 10 wt %, such as less than 5 wt % or less than 1 wt %, based on total weight of the pharmaceutical composition. The amount of organic solvent may range from 60 wt % to 95 wt %, based on total weight of the pharmaceutical composition, e.g., 65 wt % to 90 wt %, 70 wt % to 85 wt %, or 75 wt % to 80 wt %.

In some embodiments, the vehicle includes a hydrophobic solvent. Hydrophobic solvents suitable for use in the vehicles of the present disclosure may be selected based on their ability to solubilize a polymer component of the vehicles described herein. Hydrophobic solvents can be characterized as being insoluble or substantially insoluble in water. For example, suitable hydrophobic solvents have solubility in water of less than 5% by weight, less than 4% by weight, less than 3% by weight, less than 2% by weight or less than 1% by weight, e.g. as measured at 25° C. A suitable hydrophobic solvent may also be characterized as one which has a solubility in water of about 5% or less, about 4% or less, about 3% or less, about 2% or less, or about 1% or less, at 25° C. For example, in some embodiments, a suitable hydrophobic solvent has a solubility in water of from about 1% to about 7%, from about 1% to about 6%, from about 1% to about 5%, from about 1% to about 4%, from about 1% to about 3%, and from about 1% to about 2%, at 25° C. A suitable hydrophobic solvent may also be characterized as a solvent in which water has limited solubility, e.g., a solvent in which water has solubility of less than 10% by weight, less than 5% by weight, or less than 1% by weight, at 25° C.

In some embodiments, suitable hydrophobic solvents include derivatives of benzoic acid including, but not limited to, benzyl alcohol, methyl benzoate, ethyl benzoate, n-propyl benzoate, isopropyl benzoate, butyl benzoate, isobutyl benzoate, sec-butyl benzoate, tert-butyl benzoate, isoamyl benzoate and benzyl benzoate.

In some embodiments, benzyl benzoate is selected as the hydrophobic solvent for use in the vehicles of the present disclosure.

A suitable solvent may be a single solvent selected from among the following or a combination of two or more of the following: benzyl alcohol, benzyl benzoate, ethyl benzoate, and ethanol.

Where the solvent is a hydrophobic solvent, it may be used in combination with one or more additional solvents, e.g., one or more hydrophobic solvents and/or one or more polar/hydrophilic solvents.

In some embodiments, the compositions include a single hydrophobic solvent as described herein without including any additional solvents.

Where the solvent is a polar/hydrophilic solvent, it may be used alone in the vehicle or in combination with one or more hydrophobic solvents as described herein. In some embodiments, where the polar/hydrophilic solvent is used in combination with one or more hydrophobic solvents as described herein, the polar/hydrophilic solvent is present in a relatively small amount relative to the hydrophobic solvent, e.g., less than 5% (e.g., less than 4%, less than 3%, less than 2%, or less than 1%) by weight of the vehicle. For example, a polar/hydrophilic solvent may be present in the vehicle in an amount of from about 5% to about 1% (e.g., from about 4% to about 1%, from about 3% to about 1%, or from about 2% to about 1%) by weight of the vehicle.

In some embodiments, the total amount of solvent in the composition is at least 70% by weight based on the total weight of the composition, e.g., at least 80% by weight, at least 90% by weight, at least 95% by weight, or at least 99% by weight. In some embodiments, the total amount of solvent in the composition ranges from 70% to 99% by weight based on the total weight of the composition, e.g., 75% to 99%, 80% to 99%, 90% to 99%, or 95% to 99%. The amount of solvent typically ranges from 60 wt % to 95 wt %, based on total weight of the pharmaceutical composition.

In some embodiments, the polymer-pharmaceutically active agent complex may allow for the use of reduced amounts of solvent in the pharmaceutical composition. For instance, the amount of solvent in the pharmaceutical composition may be less than 10 wt %, such as less than 5 wt % or less than 1 wt %, based on total weight of the pharmaceutical composition.

Since the functionalized polymer of the disclosed compositions is directly complexed with the pharmaceutically active agent, the compositions may be free of other complexing agents, such as protamine, $Zn^{2+}$, carboxymethylcellulose (CMC), or other stabilizers. In other cases, the composition comprises less than 5 wt %, less than 4 wt %, less than 3 wt %, less than 2 wt %, less than 1 wt %, less than 0.5 wt %, less than 0.2 wt %, or less than 0.1 wt % of other complexing agents, such as protamine, $Zn^{2+}$, carboxymethylcellulose (CMC), or other stabilizers.

Excipients

In some embodiments, the pharmaceutical compositions according to the present disclosure include one or more excipients, e.g., stabilizers, dyes, fillers, preservatives, buffering agents, antioxidants, wetting agents, anti-foaming agents, surfactants, and the like. Excipients may include, e.g., sucrose, polysorbate, methionine, mannitol, trehalose, etc. An example of a preferred excipient is sucrose acetate isobutyrate (SAIB).

Methionine may be included in a composition of the present disclosure as an antioxidant, and in some embodiments sucrose is included as a stabilizer. Methionine may be combined with a pharmaceutically active agent complex as described herein to form a radiation stable powder or a radiation stable composition.

In some embodiments, the pharmaceutical composition has a low excipient to pharmaceutically active agent ratio. For instance, the weight ratio of excipient to pharmaceutically active agent may range from 1:10 to 1:1000, e.g., 1:50 to 1:1000, 1:100 to 1:1000, or 1:500 to 1:1000.

Additional description of vehicles and vehicle components which may be used in connection with the disclosed compositions is provided in U.S. Patent Application Publication No. 2012/0225033, filed Nov. 23, 2011, which application is incorporated by reference herein in its entirety and for all purposes.

Radiation-Sterilized Compositions

As discussed briefly above, methionine may be combined with a pharmaceutically active agent complex as described herein to form a radiation stable powder or a radiation stable composition. Additional description of radiation-stable compositions into which the complexes of the present disclosure may be incorporated is provided in International PCT Application No. WO2013/078396, filed Nov. 21, 2012, the disclosure of which is incorporated by reference herein in its entirety and for all purposes.

For example, a radiation stable composition may be prepared by 1) combining a biodegradable polymer and a hydrophobic solvent to form a single-phase vehicle of the composition, wherein the biodegradable polymer is included in an amount of from about 5% to about 40% by weight of the vehicle, and the hydrophobic solvent is included in an amount of from about 95% to about 60% by weight of the vehicle; 2) dispersing a complex according to the present disclosure in the vehicle to form the composition; and irradiating the composition with ionizing radiation, wherein the pharmaceutically active agent maintains a purity of about 90% or greater when stored at 25° C. for a period of 24 hours after irradiation. In some embodiments antioxidant is added to the composition prior to irradiating the composition with ionizing radiation, e.g., at a dose of 10 kGy to 25 kGy. In some embodiments, the antioxidant is added in an amount ranging from about 1 wt % to about 45 wt %, relative to the amount of pharmaceutically active agent. In some embodiments, methionine is added to the composition prior to irradiating the composition, e.g., in an amount of from 0.1 wt % to about 45 wt %, relative to the amount of pharmaceutically active agent.

Pharmaceutical Composition Properties

In one aspect, the complex is present in the pharmaceutical composition in the form of particles. The particles optionally include at least one excipient in addition to the complex. The particles may have a median particle size, as measured by laser diffraction, of less than 10 micrometers, such as less than 5 micrometers, less than 3 micrometers, less than 2 micrometers, or less than 1 micrometer. In some aspects, a process comprises milling the complex to achieve the desired particle size.

The pharmaceutical compositions of the present invention typically have relatively low viscosity. For instance, the pharmaceutical compositions may have a zero shear viscosity less than 1,200 centipoise (cP), e.g., less than 1000 cP, less than 500 cP, less than 100 cP, less than 50 cP, or less than 10 cP, at 25° C. The zero shear viscosity of the pharmaceutical compositions typically range from about 10 cP to about 1200 cP, e.g., about 50 cP to about 1000 cP, or about 100 cP to about 500 cP, at 25° C.

Surprisingly, the disclosed pharmaceutical compositions typically demonstrate good syringeability and injectability while providing for sustained release of the pharmaceutically active agent in-vivo with minimal burst. Syringeability and injectability may be characterized by the time it takes to inject a known volume of the pharmaceutical composition through a syringe of known size fitted with a relatively small gauge needle, e.g., a 1-5 mL syringe fitted with a needle having a gauge of about 21 to about 27. In some embodiments, the pharmaceutical compositions of the present disclosure may be characterized as having good syringeability and injectability based on their ability to be injected through a 1 ml syringe fitted with an approximately 0.5 in needle having a gauge of about 21 to about 27, wherein a 0.5 ml volume of the pharmaceutical composition can be injected in less than 25 sec (e.g., less than 20 sec., less than 15 sec, less than 10 sec, or less than 5 sec) at 25° C. with the application of a 5 to 10 lb-force. In some embodiments, under the above conditions, the pharmaceutical composition can be injected in a range of from about 1.5 sec to about 25 sec, e.g., from about 1.5 sec to about 20 sec, from about 1.5 sec to about 15 sec, from about 1.5 sec to about 10 sec, or from about 1.5 sec to about 5 sec.

In addition to good injectability and syringeability as described herein, in some embodiments, the pharmaceutical compositions of the present disclosure demonstrate minimal burst and sustained delivery of pharmaceutically active agent over time. "Minimal burst" may be characterized in terms of Cmax/Cmin, wherein the acceptable Cmax/Cmin upper limit may vary depending on the pharmaceutically active agent to be delivered. In some embodiments, the weight % of pharmaceutically active agent released as burst over the first 24 hours is less than 30% of the total amount released over one week, e.g., less than 20% or less than 10%, of the total amount released over one week. For example, the weight % of pharmaceutically active agent released as burst over the first 24 hours may be less than about 30%, less than about 20%, less than about 20%, or less than about 10%, of the total amount released over one week. In some embodiments, the weight % of pharmaceutically active agent released as burst over the first 24 hours is less than 10% of the total amount released over one month, e.g., less than 8% or less than 5%, of the total amount released over one month. For example, the weight % of pharmaceutically active agent released as burst over the first 24 hours may be less than 10% to about 8% or from about 8% to about 5%, of the total amount released over one month. In some embodiments, the Cmax to Cmin ratio of the pharmaceutically active agent, as measured over 28 days, 21 days, 14 days, or 7 days after administration, may range from 2 to 40, such as from 5 to 30, or 10 to 20. In some embodiments, the Cmax to Cmin ratio of the pharmaceutically active agent, as measured over 7 days after administration, may be less than 10, less than 5, less than 4, or less than 2. As used herein, "sustained delivery" refers to durations which are at least several fold, e.g., at least 5 fold to at least 10 fold, longer than the duration obtained from a single dose of an immediate-release (IR) formulation of the same pharmaceutically active agent (determined by Adsorption, Distribution, Metabolism, and Excretion (ADME) characteristics of the pharmaceutically active agent itself).

As mentioned above, the disclosed biodegradable compositions provide for sustained release of the pharmaceutically active agent in-vivo with minimal burst effect in addition to possessing good injectability, syringeability and chemical stability as discussed above. This is an unexpected and surprising result as currently available formulations generally provide either controlled release or injectability/syringeability but not both. For example, commercially available depot formulations may rely on the formation of an extremely viscous polymer matrix to provide controlled release of a pharmaceutically active agent. However, such formulations have poor injectability/syringeability due to the viscous nature of the depot. Alternatively, other commercially available formulations utilize vehicles which may have good injectability/syringeability due to a high-solvent content but poor control over release of the pharmaceutically active agent. Moreover, one would expect a low viscosity liquid composition such as those disclosed herein to have poor release kinetics in the form of a substantial burst effect and an exponentially declining delivery profile. Contrary to this expectation, the present compositions demonstrate low burst effect and good control over release of the pharmaceutically active agent over a period of one day to one month or longer.

Administration of Pharmaceutical Compositions

As discussed previously herein, the disclosed compositions typically possess low viscosity along with good injectability and syringeability making them well suited for delivery via a syringe (e.g., a 1-5 mL syringe) with a needle, e.g., 18 gauge to 27 gauge, such as a narrow gauge needle, e.g., 21 to 27 gauge. In addition, the pharmaceutical compositions may also be delivered via one or more pen injectors or needleless injectors known in the art.

The pharmaceutical formulations of the present invention allow for low injection volume. For instance, the injection volume may be less than 1 mL, such as less than 750 µL, less than 500 µL, or less than 250 µL.

Suitable routes of administration include, but are not limited to, subcutaneous injection and intramuscular injection. Suitable routes of administration also include, for example, intra-articular and intra-ocular, e.g., intra-vitreal, administration for local delivery.

The pharmaceutical compositions disclosed herein may also find use in oral compositions, e.g., compositions delivered in a gel-cap (soft or hard) or as a mouthwash.

The compositions of the present disclosure may be formulated such that a desired pharmacological effect is achieved via administration on a periodic basis. For example, the compositions may be formulated for administration on a daily, weekly or monthly basis.

The actual dose of the pharmaceutically active agent to be administered will vary depending on the pharmaceutically active agent, the condition being treated, as well as the age, weight, and general condition of the subject as well as the severity of the condition being treated, and the judgment of the health care professional. Therapeutically effective amounts are known to those skilled in the art and/or are described in the pertinent reference texts and literature.

For example, in the case of proteins and peptides pharmaceutically active agents, the pharmaceutically active agent will typically be delivered such that plasma levels of the pharmaceutically active agent are within a range of about 1 picomole/liter to about 1 micromole/liter, such as about 5 picomoles/liter to about 1 nanomole/liter or about 50 picomoles/liter to about 200 picomoles/liter. On a weight basis, a therapeutically effective dosage amount of protein or peptide will typically range from about 0.01 mg per day to about 1000 mg per day for an adult. For example, peptide or protein dosages may range from about 0.1 mg per day to about 100 mg per day, or from about 1.0 mg per day to about 10 mg/day.

In some embodiments, a suitable low molecular weight compound may be characterized as one which can provide the desired therapeutic effect with a dose of less than or equal to about 30 mg/day as delivered from a depot administered once a week, or a dose of less than or equal to about 10 mg/day as delivered from a depot administered once a month. For example, a suitable low molecular weight compound may be one which can provide the desired therapeutic effect with a dose of less than about 30 mg/day, e.g., less than about 25 mg/day, less than about 20 mg/day, less than about 15 mg/day, less than about 10 mg/day, less than about 5 mg/day or less than about 1 mg/day as delivered from a depot administered once a week. In some embodiments, a suitable low molecular weight compound is one which can provide the desired therapeutic effect with a dose of from about 1 mg/day to about 30 mg/day, e.g., from about 5 mg/day to about 25 mg/day, or from about 10 mg/day to about 20 mg/day as delivered from a depot administered once a week. In some embodiments, the dose may range from 0.1 mg/kg to 10 mg/kg, such as 0.5 mg/kg to 5 mg/kg or 1 mg/kg to 3 mg/kg.

Similarly, a suitable low molecular weight compound may be one which can provide the desired therapeutic effect with a dose of less than about 10 mg/day, less than about 9 mg/day, less than about 8 mg/day, less than about 7 mg/day, less than about 6 mg/day, less than about 5 mg/day, less than about 4 mg/day, less than about 3 mg/day, less than about 2 mg/day or less than about 1 mg/day as delivered from a depot administered once a month. In some embodiments, a suitable low molecular weight compound may be one which can provide the desired therapeutic effect with a dose of from about 1 mg/day to about 10 mg/day, e.g., from about 2 mg/day to about 9 mg/day, from about 3 mg/day to about 8 mg/day, from about 4 mg/day to about 7 mg/day, or from about 5 mg/day to about 6 mg/day as delivered from a depot administered once a month.

In some embodiments, the Cmax to Cmin ratio of the pharmaceutical active agent, as measured over 28 days, 21 days, 14 days, or 7 days after administration, typically ranges from 2 to 40, such as from 5 to 30 or 10 to 20, and may be less than 10, less than 5, less than 4, or less than 2.

In some embodiments, e.g., where the composition may have been in storage for a period of time prior to injection, the composition may be mixed, e.g., via shaking, prior to administration to ensure that the complex comprising pharmaceutically active agent is sufficiently dispersed in the vehicle carrier.

In some embodiments the pharmaceutical compositions disclosed herein (or components thereof) are sterilized prior to use, e.g., via the application of a sterilizing dose of ionizing radiation. For example, in one embodiment one or both of the complex and pharmaceutical composition as disclosed herein are sterilized with ionizing radiation, e.g., gamma radiation, e-beam radiation, or x-ray radiation.

One of ordinary skill in the art will be able to determine an appropriate sterilizing dose of radiation based on a variety of factors including, e.g., the type of radiation, the shape, size, and/or composition of the material to be sterilized, the desired level of sterility and the amount of contamination present prior to sterilization. The irradiation may be conducted with the complex or the pharmaceutical composition maintained at from about 0° C. to about 30° C., e.g., from about 5° C. to about 20° C. or about about 10° C. to about 15° C.

In some embodiments, a suitable dose of sterilizing radiation is a dose of about 10 kGy to about 25 kGy, e.g., about 15 kGy to about 20 kGy.

In some embodiments, when stored at 2° C., 8° C., or 25° C., the composition maintains a purity of at least 90% or greater (e.g., at least 95% or greater) for a period of at least 24 hours following exposure to gamma irradiation at a dose of about 10 kGy to about 25 kGy, e.g., about 15 kGy to about 20 kGy. For example, the period may be 3 months, 6 months, 1 year, or 2 years. In some embodiments, a purity of at least 90% or greater (e.g., 95% or greater) is maintained for a period of at least one month, e.g., following exposure to gamma irradiation at a dose of about 10 kGy to about 25 kGy, e.g., about 15 kGy to about 20 kGy. For example, the period may be from about one month to about two months, from about two months to about three months, from about three months to about four months, from about four months to about five months, from about five months to about six months, from about six months to about one year, or from about one year to about two years.

Purity may be determined, for example, based on Reverse Phase High Pressure Liquid Chromatographic (RPLC) analysis of the composition. For example, RPLC spectra for the active agent in the irradiated composition can be compared with RPLC spectra for a USP standard of the active agent. Peak retention times for the active agent in the irradiated composition can be matched to the USP standard for the active agent, and impurity peaks can be subtracted to obtain % purity levels.

Kits

A variety of kits may be provided which include one or more components of the pharmaceutical compositions disclosed herein along with instructions for preparing and/or using the same. For example, in one embodiment, a suitable kit may include a vehicle as described herein in a first container and a complex comprising pharmaceutically active agent as described herein in a second container, e.g., in powder form. These components may then be mixed together prior to injection to form a pharmaceutical composition according to the present disclosure. In some embodiments, the first container is a syringe which may be coupled to the second container, e.g., a vial with a luer lock, to provide a mechanism for mixing the vehicle and the complex comprising pharmaceutically active agent. In other embodiments, both the first and second containers are syringes which may be coupled, e.g., via a luer lock, to provide a mechanism for mixing the vehicle and the complex comprising pharmaceutically active agent.

In another embodiment, the pharmaceutical composition may be provided pre-mixed in a single container, e.g., a single syringe.

In another embodiment, the pharmaceutical composition may be provided un-mixed in a pre-filled, dual-chamber syringe including a first chamber containing the vehicle and a second chamber containing the complex comprising pharmaceutically active agent. The syringe may be provided such that a user can initiate contact and subsequent mixing of the vehicle and the complex comprising pharmaceutically active agent.

The instructions for use of the kit and/or kit components may be provided as complete written instructions along with the kit, e.g., as an insert card or printed on the kit packaging; or stored on a computer readable memory device provided with the kit. Alternatively, the kit may include instructions which provide a brief instruction to the user and direct the user to an alternate source for more complete use instructions. For example, the kit may include a reference to an internet site where the complete instructions for use may be accessed and/or downloaded.

Tissue Engineering and Medical Devices

In addition to pharmaceutical compositions, the complexes of the present invention may be used for tissue engineering and medical devices. Possible functional groups used for this application include PEGs, peptides, amino acids, amines, guanidiniums, PEGs, etc. For instance, scaffolds made from PCLs modified with the functional groups described above could be of great benefit by imparting greater hydrophilicity and biocompatibility. Active pharmaceutical substances attached as prodrugs to the polymer chains could provide enhanced performance.

By functionalizing the polymers along the length of the chain, multiple potential interaction sites are created, as opposed to only a few with traditional polymers. For instance, precursor polymers (homopolymers or copolymers) may be synthesized with pendant azide or alkyne groups, and then these precursor polymers may be functionalized with alkyne-containing or azide-containing substrates using "click" chemistry.

The compositions disclosed herein may find use as coatings for medical devices, e.g., implantable medical devices. Such coatings may be applied, e.g., by dip-coating the medical device prior to implantation.

As noted above, the compositions disclosed herein may find use as biomaterials in tissue engineering. Tissue scaffolds and other useful structures may be fabricated by various methods including melt spinning, solvent spinning, electrospinning, and 3-D printing. Incorporation of various functional groups could render scaffolds and other structures more hydrophilic, adhesive, and more biocompatible than materials that are currently available.

Precursor Polymer Synthesis

In certain embodiments, precursor polymers according to the present disclosure are synthesized by an alcohol-initiated polymerization reaction. For example, monomer starting material (e.g., α-chloro-ε-caprolactone, ε-caprolactone, and the like) may be mixed with an alcohol, e.g., a mono or a poly-functional alcohol, such as but not limited to, 1-dodecanol, 1,6-hexanediol, and the like. In some instances, a catalyst is included in the polymerization reaction. Catalysts suitable for precursor polymer synthesis according to embodiments of the present disclosure include, but are not limited to, stannous 2-ethylhexanoate, stannic chloride dihydrate, and the like. Other catalysts may also be used, such as Lewis acids, alkyl metals, and organic acids. In certain cases, the catalyst is included in the reaction in an amount ranging from 0.01 wt % to 5 wt %, such as 0.05 wt % to 3 wt %, including 0.1 wt % to 1 wt %. In some instances, the catalyst is included in the reaction in an amount of 0.1 wt %. In certain embodiments, the polymerization reaction is heated to a temperature of 100° C. or more, such as a temperature ranging from 100° C. to 200° C., or from 110° C. to 175° C., or from 120° C. to 150° C. In some instances, the polymerization reaction is heated to a temperature of 130° C. In certain embodiments, the polymerization reaction is allowed to proceed for a time period of overnight or longer. For example, the polymerization reaction may be allowed to proceed for 12 hours or more, such as 18 hours or more, or 24 hours or more, or 30 hours or more, or 36 hours or more, or 42 hours or more, or 48 hours or more.

Examples of precursor polymer synthesis according to the present disclosure are described below in, e.g., Example 1.

Functionalizing Polymers

In certain embodiments, precursor polymers as described above may be functionalized, i.e. their functionalizable side groups may be transformed into ionizable side groups to thereby provide the functionalized polymers described herein. Functionalization of the precursor polymers may be performed using any of the various methods and techniques known and available to those skilled in the art. For example, click chemistry reactions may be used to functionalize the precursor polymers. In certain instances, a Huisgen 1,3-dipolar cycloaddition reaction (e.g., an azide-alkyne Huisgen cycloaddition reaction) may be used to functionalize the precursor polymers. In some instances, the precursor polymers as described above may include a leaving group, such as a halogen (e.g., chloro, bromo, iodo), a tosyl leaving group, and the like. In some instances, the leaving group may be displaced by an azide moiety (e.g., sodium azide) to form an azido substituted precursor polymer, which may then undergo a click chemistry reaction with an alkyne, such as in a Huisgen 1,3-dipolar cycloaddition reaction as described above. In certain embodiments, a catalyst may be included in the cycloaddition reaction. Catalysts suitable for cycloaddition reactions according to embodiments of the present disclosure include, but are not limited to, copper catalysts, such as copper iodide, and the like. In certain cases, the catalyst is included in the reaction in an amount ranging from 0.01 equiv. to 1 equiv., such as 0.05 equiv. to 0.5 equiv., including 0.1 equiv. to 0.3 equiv. In some instances, the catalyst is included in the reaction in an amount of 0.1 equiv.

The functionalizing typically involves a solvent in which the precursor polymer is soluble. In some embodiments, the solvent used during the functionalizing may comprise at least one member selected from an amide, cyclic amide, chlorinated hydrocarbon, ketone, ether, cyclic ether, polar aprotic, or protic solvent. Such solvents could include, but are not limited to, DMF, NMP, chloroform, dichloromethane (DCM), acetone, tetrahydrofuran (THF), acetonitrile, dimethylsulfoxide (DMSO), water, and combinations thereof.

In many embodiments, the functionalizing comprises an exothermic reaction. In many embodiments, the functionalizing involves cooling and mixing. In some embodiments, the temperature of the functionalizing ranges from 10° C. to 40° C., such as 20° C. to 30° C.

The purification may comprise dialysis, stirred cell purification, and/or tangential flow filtration. The pH of the purification typically falls within the range of 3 to 10. For instance, purification of amine-containing functionalized polymers often ranges from 4 to 5. The purification of acid-containing functionalized polymers often ranges from 8 to 9.

Examples of reactions for functionalizing polymers according to the present disclosure are described below in, e.g., Example 2.

In one specific aspect, there is provided a method comprising: providing a precursor polymer comprising repeat units, the repeat units comprising functionalizable repeat units comprising at least one functionalizable side group; obtaining a functionalized polymer by transforming, using click chemistry, said functionalizable repeat units into ionizable repeat units comprising at least one ionizable side group; and combining the functionalized polymer with a pharmaceutically active agent to form a complex in which a plurality of the at least one ionizable side groups form a plurality of non-covalent bonds with the pharmaceutically active agent. The complex may be a complex as defined elsewhere herein.

In this aspect, the transforming, using click chemistry, may comprise effecting a cycloaddition reaction. The cycloaddition reaction may be a Diels-Alder cycloaddition reaction. The cycloaddition reaction may be a Huisgen 1,3-dipolar cycloaddition reaction. The cycloaddition reaction may be a cycloaddition reaction between an azide and an alkyne to form a linkage comprising a 1,2,3-triazole.

The functionalizable side group may be an azido group and the transforming, using click chemistry, may comprise reacting the precursor polymer with an alkyne to form the functionalized polymer, the functionalized polymer comprising at least one 1,2,3-triazole ring. Alternatively, the functionalizable side group may be a leaving group and the transforming, using click chemistry, may comprise: (a) transforming the leaving group into an azido group and thereby providing a polymer intermediate; and (b) reacting the polymer intermediate with an alkyne to form the functionalized polymer, the functionalized polymer comprising at least one 1,2,3-triazole ring. Examples of leaving group include a halogen (e.g., chloro, bromo, iodo), a tosyl leaving group, and the like. In some embodiments the leaving group is a halogen, for example chloro. The leaving group may be transformed into an azido group by reacting the precursor polymer with sodium azide. The alkyne may be a terminal alkyne.

In some embodiments, the functionalizable side group may be an alkynyl group and the transforming, using click chemistry, may comprise reacting the precursor polymer with an azide to form the functionalized polymer, the functionalized polymer comprising at least one 1,2,3-triazole ring. The alkynyl group may, for example, be a terminal alkynyl group.

In some embodiments, the transforming, using click chemistry, comprises a monovalent copper catalyzed reaction or a ruthenium catalyzed reaction. For example, the transforming, using click chemistry, may comprise a monovalent copper catalyzed reaction, wherein a monovalent copper catalyst is provided in the reaction through the ionization of copper iodide or copper bromide.

In some embodiments, the transforming, using click chemistry, comprises a copper catalyzed azide-alkyne cycloaddition reaction. In some embodiments, the transforming, using click chemistry, occurs at least partially under degassing conditions.

In some embodiments, the precursor polymer comprises repeat units of the formula (I'):

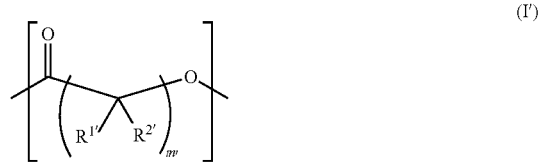

(I')

wherein m' is an integer from 1 to 10, and each $R^{1'}$ and $R^{2'}$ is independently selected from hydrogen, hydroxyl, optionally substituted alkyl, optionally substituted alkenyl, optionally substituted alkynyl, optionally substituted alkoxy, optionally substituted carbocyclyl, optionally substituted aryl, optionally substituted heterocyclyl, optionally substituted heteroaryl, a ionizable side group, and a functionalizable side group. Such precursor polymers can readily be obtained by polymerization of monomers, such as monomers that are or are derivatives of caprolactone, lactic acid, glycolic acid, lactide, glycolide, butyrolactone, and valerolactone.

In some embodiments, the precursor polymer comprises functionalizable repeat units of the formula (I') wherein at least one of the $R^{1'}$s and $R^{2'}$s is a functionalizable side group. In some embodiments, the precursor polymer comprises repeat units of the formula (I') wherein each $R^{1'}$ and $R^{2'}$ is independently selected from hydrogen, $C_{1-5}$ alkyl and a functionalizable side group. In some embodiments, the precursor polymer comprises repeat units of the formula (I') wherein m' is an integer from 1 to 5. In some embodiments, the precursor polymer comprises repeat units of the formula (I') wherein one of the $R^{1'}$s and $R^{2'}$s is a functionalizable side group and all of the remaining $R^{1'}$s and $R^{2'}$s are not functionalizable side groups.

In some embodiments, the precursor polymer comprises repeat units of the formula (I') wherein m' is 5, one $R^{1'}$ is a functionalizable side group and all of the remaining $R^{1'}$s and $R^{2'}$s are hydrogen. Alternatively or additionally, the precursor polymer may comprise repeat units of the formula (I') wherein m' is 5 and all of the $R^{1'}$s and $R^{2'}$s are hydrogen.

In some embodiments, the precursor polymer comprises repeat units of the formula (I') wherein m' is 1, $R^{1'}$ is hydrogen and $R^{2'}$ is hydrogen. In some embodiments, the precursor polymer comprises repeat units of the formula (I') wherein m' is 1, $R^{1'}$ is methyl and $R^{2'}$ is hydrogen. In some embodiments, the precursor polymer comprises repeat units of the formula (I') wherein m' is 2, the $R^{1'}$ and $R^{2'}$ alpha to the carbonyl group in formula (I') are each hydrogen, the $R^{1'}$ beta to the carbonyl group is methyl and the $R^{2'}$ beta to the carbonyl group is hydrogen. In some embodiments, the precursor polymer comprises repeat units of the formula (I') wherein m is 3 and all of the $R^{1'}$s and $R^{2'}$s are hydrogen. In some embodiments, the precursor polymer comprises repeat units of the formula (I') wherein m' is 4, and all of the $R^{1'}$s and $R^{2'}$s are hydrogen. In some embodiments, the precursor polymer comprises repeat units of the formula (I') wherein m is 3, the $R^{1'}$ and $R^{2'}$ alpha to the carbonyl group in formula (I') are each hydrogen, the $R^{1'}$ and $R^{2'}$ beta to the carbonyl group are each hydrogen, and the $R^{1'}$ gamma to the carbonyl group is methyl and the $R^{2'}$ gamma to the carbonyl group is hydrogen.

In some embodiments, the functionalizable group is selected from a leaving group, an azido group or an alkynyl group.

In some embodiments, the precursor polymer is a homopolymer of repeat units of formula (I') wherein at least one of the $R^{1'}$s and $R^{2'}$s is a functionalizable side group. In other embodiments, the precursor polymer is a copolymer comprising at least two different repeat units. For example the precursor polymer may be a copolymer wherein each of said at least two different repeat units is of formula (I') and wherein at least one of said at least two different repeat units has a formula (I') in which at least one of the $R^1$s and $R^{2'}$s is a functionalizable side group.

In some embodiments, synthesis of the functionalized polymers involves click chemistry. In other embodiments, the synthesis of functionalized polymers does not involve click chemistry. Thus, in some embodiments, the ionizable groups may be included in the functionalized polymer using click chemistry. Alternatively, the ionizable groups may be added via non-click chemistry routes.

Copper Catalyzed Click Chemistry

Monovalent copper catalyzed "click chemistry" cycloaddition reactions may be used to functionalize polymers with ionizable side groups to provide functionalized polymers capable of forming complexes with pharmaceutically active agents as described herein. In some embodiments, ionizable side groups are bonded to precursor polymers via a monovalent copper catalyzed azide-alkyne cycloaddition reaction. The monovalent copper catalyst may be provided in the reaction through the ionization of copper iodide or copper bromide.

Other Metal Catalysts

Cu is not the only metal capable of catalyzing this type of cycloaddition. As long as the metal is or can become coordinatively unsaturated, other metals known to form stable acetylides may also be employed. Exemplary metals that can form stable acetylides include Cu, Au, Ag, Hg, Cd, Zr, Ru, Fe, Co, Pt, Pd, Ni, Rh, and W. It is a matter of finding the right metal/ligand combination.

Catalysis of Ligation Reaction by Metallic Container: Metallic containers can also be used as a source of the catalytic species to catalyze the ligation reaction. For example, a copper container ($Cu^0$) may be employed to catalyze the reaction. In order to supply the necessary ions, the reaction solution must make physical contact with the copper surface of the container. Alternatively, the reaction may be run in a non-metallic container, and the catalytic metal ions supplied by contacting the reaction solution with a copper wire, copper shavings, or other structures. Although these reactions may take longer to proceed to completion, the experimental procedure is relatively simple.

Alternative Reducing Agents: Metals may be employed as reducing agents to maintain the oxidation state of the Cu (I) catalyst or of other metal catalysts. Preferred metallic reducing agents include Cu, Al, Be, Co, Cr, Fe, Mg, Mn, Ni, and Zn. Alternatively, an applied electric potential may be employed to maintain the oxidation state of the catalyst.

Cu(I) Salt Used Directly: If Cu(I) salt is used directly, no reducing agent is necessary, but acetonitrile or one of the other ligands indicated above should be used as a solvent (to prevent rapid oxidation of Cu(I) to Cu(II) and one equivalent of an amine should be added (to accelerate the otherwise extremely slow reaction-vide supra). In this case, for better yields and product purity, oxygen should be excluded. Therefore, the ascorbate (or any other reducing) procedure is often preferred over the unreduced procedure. The use of a reducing agent is procedurally simple, and furnishes triazole products in excellent yields and of high purity. For instance, in some cases, the yield of the functionalizing step may range from 40% to 90%, such as 45% to 80% or 50% to 75%. In the exemplary click chemistry synthesis route shown below, an azide (—$N_3$) is placed on the polymer chain and functionalized via click reaction. It may be accomplished in an advantageous "one pot" approach. It is also advantageous in that it negates the need for synthesizing small molecule azides that are potentially explosive.

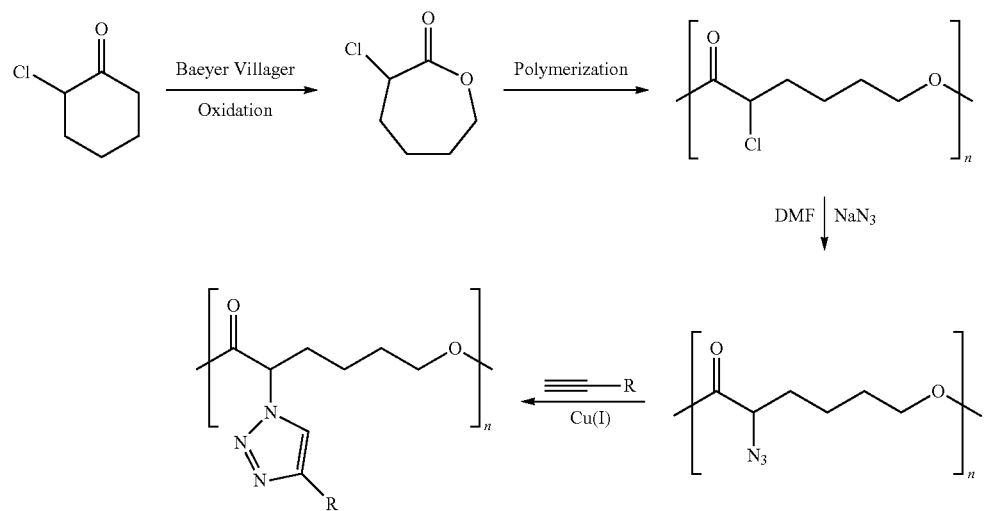

Another exemplary click chemistry reaction scheme is shown below:

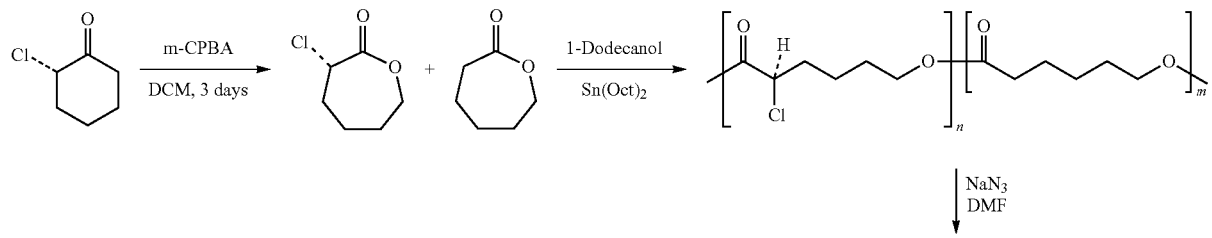

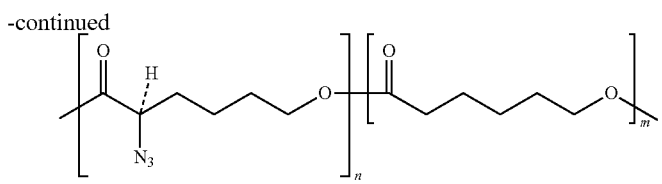

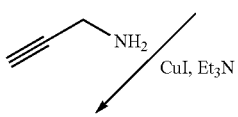

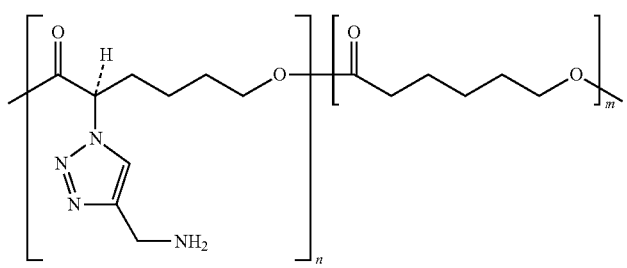

In the above reaction scheme, Baeyer-Villiger oxidation was performed on α-chlorocyclohexanone. The crude reaction product may be purified to give desired monomer.

Also in the above reaction scheme, copolymer was reacted with the "click" reagents to form the desired amine-functionalized complexation polymer.

The click reaction is typically followed by purification. Purification may involve dialysis, stirred cell, ultrafiltration, and/or tangential flow filtration. The purification may be conducted at various pH, such as from 4 to 9, such as 4 to 5 for amine functionalized polymers, and such as 8 to 9 for acid functionalized polymers.

Polymer Synthesis via Non-Click Chemistry

The below exemplary reaction scheme, which does not involve click chemistry, has been used to form a functionalized polymer, i.e., an amine-terminated polymer.

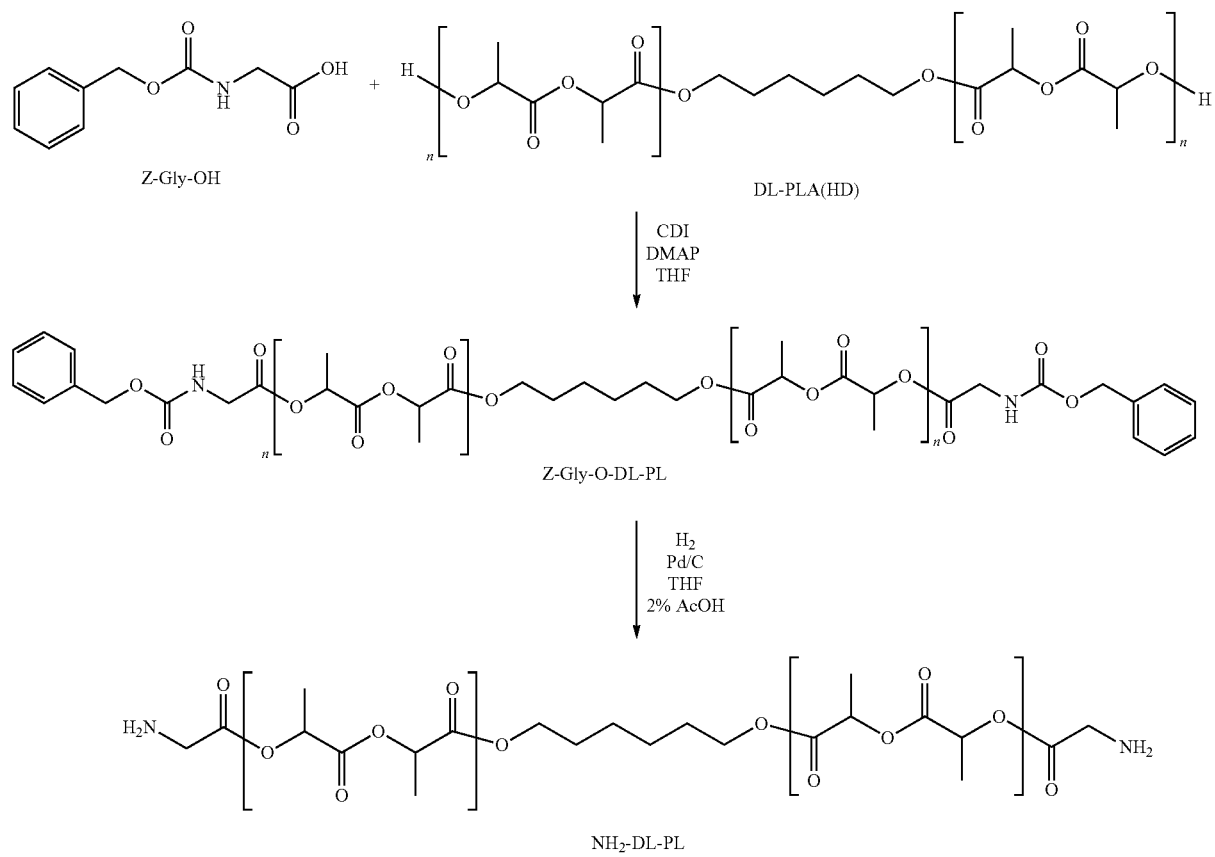

In some embodiments, a functionalized polymer according to the present disclosure, which is not produced via click chemistry, comprises at least one terminal repeat unit that has the formula (I″).

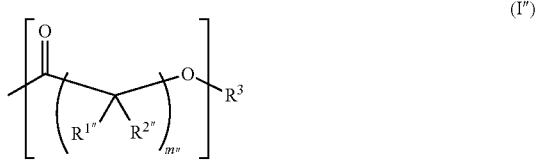

wherein m″ is an integer from 1 to 10, each $R^{1″}$ and $R^{2″}$ is independently selected from hydrogen, hydroxyl, optionally substituted alkyl, optionally substituted alkenyl, optionally substituted alkynyl, optionally substituted alkoxy, optionally substituted carbocyclyl, optionally substituted aryl, optionally substituted heterocyclyl, optionally substituted heteroaryl, and a ionizable side group; and $R^3$ is an ionizable end group.

By "terminal repeat unit" is meant a repeat unit that is at the end of the polymer chain. In some embodiments a repeat unit of the formula (I″) is present at both ends of the polymer chain. In some embodiments a repeat unit of the formula (I″) is present at one end of the polymer chain.

In some embodiments, the chemical identities and combinations of the groups m″ and $R^{1″}$ and $R^{2″}$ are as described herein with reference to the formula (I) (i.e., with reference to the groups m and $R^1$ and $R^2$). In some embodiments, the ionizable end group $R^3$ comprises at least one member selected from ammonium, carboxylate, hydrazinium, guanidinium, sulfate, sulfonate, phosphonate and phosphate. Methods for attaching chemical end groups, including ionizable end groups, to polymers are well known in the art and can be adopted in order to prepare the above-described polymers.

In some embodiments, these functionalized, ionizable end group comprising polymers find use in the formation of complexes with relatively low molecular weight pharmaceutically active agents, e.g., pharmaceutical active agents having a weight average molecular weight or number average molecular weight ranging from 300 Daltons to 2,500 Daltons, e.g., from 500 Daltons to 2,000 Daltons, or from 1,000 Daltons to 1,500 Daltons, as determined using gel permeation chromatography or NMR spectra respectively.

Further examples of functionalized polymers made through non-click chemistry techniques include, but are not limited to, poly(L-serine) or poly (L-serine ester) (JACS 1992, 114, 3962-3965; Macromolecules 1990, 23, 3399-3406; Polymer Bulletin 1990, 24, 349-353); synthetic poly (amino acids) (Kohn, Biodegradable Polymers as Drug Delivery Systems, 1990, 195-229); polycondensation of serinol (J Control Release 2005, 101, 21-34); poly(vinylpyridine) (Sigma Aldrich Part #472352); and poly (vinylamine) analogs (PCT Publication No. WO 1998/018833).

Preparation of Complexes

In certain embodiments, functionalized polymers as described above may form a complex with a pharmaceutically active agent. In some instances, the pharmaceutically active agent may be dissolved in a solution. Suitable solvents for dissolving the pharmaceutically active agent include solvents in which the pharmaceutically active agent is soluble. In some cases, the solvent is compatible with the pharmaceutically active agent, such that the solvent is non-reactive with the pharmaceutically active agent and does not cause significant degradation of the pharmaceutically active agent or the product complex. Examples of suitable solvents include water, which may also include a buffer (e.g., $NaHCO_3$). In some instances, the functionalized polymer may be dissolved in a solution. Suitable solvents for dissolving the functionalized polymer include solvents in which the functionalized polymer is soluble. In some cases, the solvent is compatible with the functionalized polymer, such that the solvent is non-reactive with the functionalized polymer and does not cause significant degradation of the functionalized polymer or the product complex. Examples of suitable solvents include water, which may also include a buffer (e.g., $NaHCO_3$), DMSO, NMP, ethyl acetate, and benzyl alcohol.

In certain embodiments, a solution of the functionalized polymer and the pharmaceutically active agent may be combined to form a complex between the functionalized polymer and the pharmaceutically active agent. In some instances, the complex between the functionalized polymer and the pharmaceutically active agent is less soluble in the complexation solvent than the functionalized polymer and/or the pharmaceutically active agent themselves. The term "complexation solvent" is used herein to differentiate between the solvent or solvents used in the complexation of the functionalized polymer with the pharmaceutically active agent and other solvents described herein, e.g., solvents utilized in a vehicle component of a composition. For instance, the complex between the functionalized polymer and the pharmaceutically active agent may be substantially insoluble in the complexation solvent and form an isolatable precipitate. Isolation of the complex (e.g., separation of the precipitate from the supernatant) may be performed by any convenient isolation method, such as centrifugation, filtration, etc. In certain instances, the isolated complex is dried to form a dried composition of the complexed pharmaceutically active agent. For example, the isolated complex may be dried by any convenient drying method, such as, but not limited to, spray drying, freeze drying (i.e., lyophilization), drying under reduced atmospheric pressure (e.g., drying under vacuum), thin film evaporation, combinations thereof, and the like. In certain instances, the complex is a spray-dried complex. In certain instances, the complex is a lyophilized complex.

In some embodiments, the formation of the complex occurs at a temperature ranging from 10° C. to 40° C., such as 20° C. to 30° C.

Examples of the preparation of complexes according to the present disclosure are described below in, e.g., Example 3.

The present invention will be further illustrated by way of the following Examples. These examples are non-limiting and do not restrict the scope of the invention. Unless stated otherwise, all percentages, parts, etc. presented in the examples are by weight.

EXAMPLES

Example 1: Examples of Precursor Polymer Synthesis

The following are examples of precursor polymer synthesis. The resulting precursor polymers are then used to form complexing polymers, e.g., as described in Example 2.

Example 1A

In a 40 mL-screw top vial, 29.73 g of α-chloro-ε-caprolactone (made according to R. Jerome, Macromolecules, vol.

37, 2004, p. 4055), and 0.28 grams 1-dodecanol were mixed at ambient temperature. Stannous 2-ethylhexanoate was added as a solution in dry toluene. The amount of catalyst added was approximately 0.1 wt %. The vial was then placed in a block heater at 130° C. and agitated by hand periodically. The polymerization was allowed to proceed for 19.5 hours, and the vial was removed from the heating block. The resulting polymer had a number average molecular weight (Mn) of 20.8 kDa as measured by $^1$H NMR and a weight average molecular weight (Mw) of 30.5 kDa as measured by GPC in THF. Similar lots were prepared with varying amounts of 1-dodecanol to provide polymers having an Mn by NMR of 25.2 kDa and a Mw by GPC of 29.2 kDa, an Mn by NMR of 22.0 kDa and a Mw by GPC of 41.9 kDa, an Mn by NMR of 14.0 kDa and a Mw by GPC of 20.6 kDa, and an Mn by NMR of 24.0 kDa and a Mw by GPC of 27.8 kDa.

Example 1B

In a 20 mL-screw top vial, 4.95 g of α-chloro-ε-caprolactone, 4.95 g of DL-lactide, and 0.09 grams 1-dodecanol were mixed at ambient temperature. Stannous 2-ethylhexanoate was added as a solution in dry toluene. The amount of catalyst added was approximately 0.1 wt %. The vial was then placed in a block heater at 130° C. and agitated by hand periodically. The polymerization was allowed to proceed for 19.5 hours, and the vial was removed from the heating block. The resulting polymer had a number average molecular weight (Mn) of 18.0 kDa as measured by $^1$H NMR and a weight average molecular weight (Mw) of 32.9 kDa as measured by GPC in THF. The molar ratio of α-chloro-ε-caprolactone to DL-lactide was 50:50. Similar lots were prepared with varying ratios of monomers and amounts of 1-dodecanol to provide polymers having weight average molecular weight (Mw) of 5.6 and 31.8 kDa.

Example 1C

The procedure in Example 1B was repeated except that the components of the synthesis were: ε-caprolactone (4.95 grams), α-chloro-ε-caprolactone (4.96 grams), and 1-dodecanol (0.09 grams). The resulting polymer had a number average molecular weight (Mn) of 17.2 kDa as measured by $^1$H NMR and a Mw by GPC of 42.7 kDa. The molar ratio of α-chloro-ε-caprolactone to ε-caprolactone was 44:56. Similar lots were prepared with varying amounts of 1-dodecanol to provide polymers having weight average molecular weight (Mw) of 5.4 kDa, 5.6 kDa, 11.4 kDa, 12 kDa, 15.9 kDa, 16.0 kDa, and 16.8 kDa.

Example 1D

The procedure in Example 1B was repeated except that the components of the synthesis were: glycolide (3.40 grams), α-chloro-ε-caprolactone (6.52 grams), and 1-dodecanol (0.09 grams). The resulting polymer had a number average molecular weight (Mn) of 20.0 kDa as measured by $^1$H NMR. The molar ratio of a-chloro-ε-caprolactone to glycolide was 60:40.

Example 1E

ε-Caprolactone (62.97 grams), α-chloro-ε-caprolactone (62.98 grams), and 1-dodecanol (4.02 grams) were added to a 250-m L, 3-neck round bottom flask. The flask was sealed with a glass stopper, a gas joint with a stopcock, and a stirrer bearing with a glass shaft and Teflon® paddle. The ambient atmosphere was removed from the flask under vacuum, and the flask was back-filled with nitrogen gas. The flask was placed in an oil batch at 130° C. and stirred under a positive pressure of nitrogen gas. After 30 minutes, stannous 2-ethylhexanoate was added as a solution in dry toluene. The amount of catalyst added was approximately 0.05 wt %. The polymerization was allowed to proceed for 29 hours. Next, the solid polymer was subjected to vacuum to remove residual monomer for 30 minutes. Then the contents of the flask were discharged from the flask into glass containers and allowed to cool. The total yield of polymer was 116.9 g, 90%. The resulting polymer had a number average (Mn) molecular weight of 5.3 kDa as measured by $^1$H NMR and a weight average molecular weight (Mw) of 15.7 kDa by GPC in THF. The molar ratio of α-chloro-ε-caprolactone to ε-caprolactone was 43:57.

Example 1F

The procedure in Example 1E was repeated except that the components of the synthesis were: ε-Caprolactone (64.40 grams), α-chloro-ε-caprolactone (64.41 grams), and 1-dodecanol (1.21 grams). The polymerization was allowed to proceed for 40 hours. Next, the solid polymer was subjected to vacuum to remove residual monomer for 30 minutes. Then the contents of the flask were discharged from the flask into glass containers and allowed to cool. The total yield of polymer was 107.88 g, 83%. The resulting polymer had a number average molecular weight (Mn) of 17.0 kDa as measured by $^1$H NMR and a weight average molecular weight (Mw) of 44.0 kDa by GPC in THF. The molar ratio of α-chloro-ε-caprolactone to ε-caprolactone was 44:56.

Example 1G

In a 40 mL-screw top vial, 7.31 g of α-chloro-ε-caprolactone, 17.5 g of DL-lactide, 4.38 g of glycolide, and 0.08 g of 1-dodecanol were mixed at ambient temperature. The catalyst stannous 2-ethylhexanoate was added as a solution in dry toluene. The amount of catalyst added was approximately 0.1 wt %. The vial was then placed in a block heater at 130° C. and agitated by hand periodically. The polymerization was allowed to proceed for 42 hours, and the vial was removed from the heating block. The resulting polymer had a number average molecular weight (Mn) of 5.1 kDa as measured by $^1$H NMR and a weight average molecular weight (Mw) of 17.5 kDa as measured by GPC in THF. The molar ratio of α-chloro-ε-caprolactone to DL-lactide to glycolide was 26:56:18.

Example 2: Synthesis of Complexation Polymers

The following examples involve converting precursor polymers, such as those formed in above Example 1, to form functionalized complexation polymers.

Example 2A

Amine Functionalized Copolymer

The precursor polymers utilized in this Example were prepared as described above in Examples 1E and 1F.

To a solution of the precursor α-chloro-ε-caprolactone-co-ε-caprolactone copolymer in N,N-dimethylformamide (DMF; 4 mL solvent/g polymer) was added sodium azide (NaN$_3$, 1.2 equiv.) with vigorous stirring via a magnetic stir bar. The flask was evacuated and back-filled with nitrogen five times and was stirred overnight at room temperature. The presence of a new organic azide moiety was confirmed by FT-IR (at ~2100 cm$^{-1}$). The flask was cooled to 0° C. in an ice bath and was evacuated and back-filled with nitrogen five times. Under a stream of nitrogen, propargyl amine (1.0 equiv.), triethylamine (0.1 equiv.), and copper iodide (0.1 equiv.) were added sequentially. The flask was again evacuated and back-filled with nitrogen. The exothermic reaction was stirred at 0° C. for an hour; the ice bath was then removed, and the reaction was stirred vigorously overnight under nitrogen. FT-IR confirmed the disappearance of the organic azide at ~2100 cm$^{-1}$, indicating the reaction was complete. The solids were filtered out of the reaction mixture and were washed with ample DMF. The filtrate was diluted with 0.01N hydrochloric acid until the solution was homogeneous and the pH was 4-5. A metal scavenger (SiliaMetS® Thiol, 8 equiv.) was added to the polymer solution, and the mixture was stirred overnight. The scavenger was filtered out, and the resulting filtrate was purified via ultrafiltration in a stirred cell using 1.5 diavolumes of purified water as the dialysate. The purified polymer solution was then transferred to VirTis® jars, shell-frozen, and lyophilized until dry. The resulting functionalized complexation polymers were called AFCP-1 (prepared using 15.7 kDa precursor polymer described in Example 1E) and AFCP-2 (prepared using 44.0 kDa precursor polymer described in Example 1F). A chemical formula for the amine functionalized complexation polymers produced in this example is provided below.

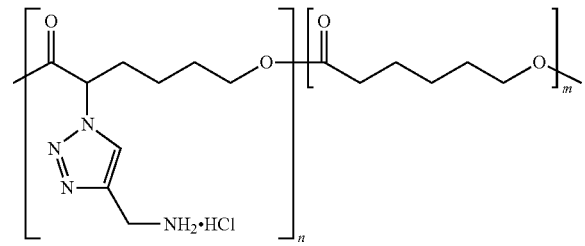

Example 2B: Amine Functionalized Homopolymer

The precursor polymer utilized in this Example was the 29.2 kDa polymer prepared as described above in Example1A.

To a solution of the precursor poly(α-chloro-ε-caprolactone) in N-methylpyrrolidone (NMP; 5 mL solvent/g polymer) was added sodium azide (NaN$_3$, 1.2 equiv.) with vigorous stirring via a magnetic stir bar. The flask was evacuated and back-filled with nitrogen five times and was stirred overnight at room temperature. The presence of a new organic azide moiety was confirmed by FT-IR (at ~2100 cm$^{-1}$). The flask was cooled to 0° C. in an ice bath and was evacuated and back-filled with nitrogen five times. Under a stream of nitrogen, propargyl amine (1.0 equiv.), triethylamine (0.1 equiv.), and copper iodide (0.1 equiv.) were added sequentially. The flask was again evacuated and back-filled with nitrogen. The exothermic reaction stirred at 0° C. for an hour; the ice bath was then removed, and the reaction continued to stir vigorously overnight under nitrogen. FT-IR confirmed the disappearance of the organic azide at ~2100 cm$^{-1}$, indicating the reaction was complete. The solids were filtered out of the reaction mixture and were washed with ample NMP. The filtrate was diluted with 0.01N hydrochloric acid until the solution was homogeneous and the pH was 4-5. A metal scavenger (SiliaMetS® Thiol, 8 equiv.) was added to the polymer solution, and the mixture was stirred overnight. The scavenger was filtered out, and the resulting filtrate was purified via ultrafiltration in a stirred cell using 1.5 diavolumes of purified water as the dialysate. The purified polymer solution was then transferred to VirTis® jars, shell-frozen, and lyophilized until dry.

Example 2C: Amine Functionalized Copolymer

The precursor polymers utilized in this Example were the 5.4 kDa, 11.4 kDa, and 16.8 kDa polymers prepared as described above in Example 1C. The procedure from Example 2A was followed, but the polymer solution was purified with conventional dialysis membrane tubing (Spectra/Por® MWCO=1 kDa or 3.5 kDa).

Example 2D: Amine Functionalized Copolymer

The precursor polymer utilized in this Example was the 15.7 kDa polymer prepared as described above in Example 1E. The procedure from Example 2B was followed, but the polymer solution was purified with a tangential flow filtration (TFF) system using deionized water as the dialysate.

Example 2E: Carboxylate Functionalized Copolymer

The precursor polymers utilized in this Example were the 5.6 kDa, 12 kDa and the 15.9 kDa polymers prepared as described above in Example 1C.

To a solution of the precursor α-chloro-ε-caprolactone-co-ε-caprolactone copolymer in N,N-dimethylformamide (DMF; 4 mL solvent/g polymer) was added sodium azide (NaN$_3$, 1.2 equiv.) with vigorous stirring via a magnetic stir bar. The flask was evacuated and back-filled with nitrogen five times and was stirred overnight at room temperature. The presence of a new organic azide moiety was confirmed by FT-IR (at ~2100 cm$^{-1}$). The flask was cooled to 0° C. in an ice bath and was evacuated and back-filled with nitrogen five times. Under a stream of nitrogen, 5-hexynoic acid (1.0 equiv.), triethylamine (0.1 equiv.), and copper iodide (0.1 equiv.) were added sequentially. The flask was again evacuated and back-filled with nitrogen. The exothermic reaction was stirred at 0° C. for an hour; the ice bath was then removed, and the reaction was stirred vigorously overnight under nitrogen. FT-IR confirmed the disappearance of the organic azide moiety, indicating the reaction was complete. The solids were filtered out of the reaction mixture and were washed with ample DMF. The filtrate was diluted with saturated aqueous sodium bicarbonate solution until the solution was homogeneous and the pH was 8-9. DOWEX™ Marathon™ C sulfonic acid ion exchange resin was washed with ample methanol to remove all color, then added to the polymer solution, and the mixture was stirred overnight. The resin was filtered out, and the resulting filtrate was purified via dialysis against deionized water using Spectra/Por® dialysis tubing overnight. The purified polymer solution was then transferred to VirTis® jars, shell-frozen, and lyophilized until dry. The carboxylate functionalized copolymers prepared with the 5.6 kDa, 12 kDa and 15.9 kDa precursor polymers correspond to the CFCP-3, CFCP-2, and CFCP-1 copolymers, respectively.

Example 2F: Guanidinium Functionalized Copolymer

The precursor polymers utilized in this Example were the 5.4 kDa, 11.4 kDa, and 16.8 kDa polymers prepared as described above in Example 1C.

To a solution of the precursor α-chloro-ε-caprolactone-co-ε-caprolactone copolymer in N,N-dimethylformamide (DMF; 4 mL solvent/g polymer) was added sodium azide (NaN$_3$, 1.2 equiv.) with vigorous stirring via a magnetic stir bar. The flask was evacuated and back-filled with nitrogen five times and was stirred overnight at room temperature. The presence of a new organic azide moiety was confirmed by FT-IR (at ~2100 cm$^{-1}$). The flask was cooled to 0° C. in an ice bath and was evacuated and back-filled with nitrogen five times. Under a stream of nitrogen, the propargyl amide of arginine dihydrochloride (structure shown below; 1.0 equiv.), triethylamine (10 equiv.), and copper iodide (0.1 equiv.) were added sequentially.

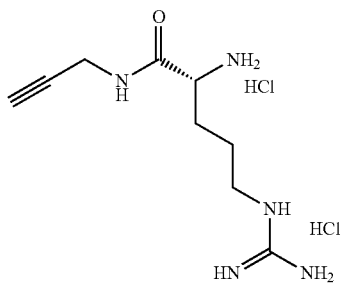

The flask was again evacuated and back-filled with nitrogen. The exothermic reaction was stirred at 0° C. for an hour; the ice bath was then removed, and the reaction was stirred vigorously overnight under nitrogen. FT-IR confirmed the disappearance of the organic azide moiety, indicating the reaction was complete. The solids were filtered out of the reaction mixture and were washed with ample DMF. The filtrate was diluted with 0.01N HCl until the solution was homogeneous and the pH was 3-4. The resulting solution was purified via dialysis using Spectra/Por® dialysis membrane tubing with MWCO=100-500 Da against 0.01N HCl overnight, then with MWCO=1000 Da tubing for one hour. The purified polymer solution was then transferred to VirTis® jars, shell-frozen, and lyophilized until dry.

Example 2G: Amine Functionalized Homopolymer

The precursor polymer utilized in this Example was the 41.9 kDa polymer prepared according to the method described in Example 1A above.

A solution of the precursor poly(α-chloro-ε-caprolactone) in DMF (4 mL solvent/g polymer) was evacuated and back-filled with nitrogen five times. Sodium azide (NaN$_3$, 1.2 equiv.) was added and stirred overnight at room temperature via a magnetic stir bar. The presence of a new organic azide moiety was confirmed by FT-IR (at 2106 cm$^{-1}$). Under a stream of nitrogen, propargyl amine (1.0 equiv.) and triethylamine (0.1 equiv.) were added sequentially. The flask was again evacuated and back-filled with nitrogen 5 times then copper iodide (0.1 equiv.) was added, followed by one additional evacuate/back-fill cycle. The reaction immediately became hot and was placed in an ice bath to control the exotherm. After 2 hours, the ice bath was removed, and the reaction was stirred overnight at room temperature under nitrogen. FT-IR confirmed the disappearance of the organic azide peak at ~2106 cm$^{-1}$, indicating the reaction was complete. The contents of the flask were centrifuged, and the green supernatant was decanted off; the solid bed was washed with ample DMF, centrifuged again, and the supernatants combined. The DMF was largely removed via rotary evaporation, and the thick green oil was dissolved in 0.01 N HCl over many hours. This solution was dialyzed in MWCO=3500 Spectra/Por® dialysis tubing against 0.01 N HCl for two days, changing the dialysate 4 times. The polymer solution was then freeze-dried for three days until dry.

Example 2H: Amine Functionalized Copolymer

The precursor polymer utilized in this Example was the 16.0 kDa polymer prepared according to the method described in Example 1C above.

A solution of the precursor poly(α-chloro-ε-caprolactone-co-ε-caprolactone) in DMF (4 mL solvent/g polymer) was evacuated and back-filled with nitrogen five times. Sodium azide (NaN$_3$, 1.2 equiv.) was added and stirred overnight at room temperature via a magnetic stir bar. The presence of a new organic azide moiety was confirmed by FT-IR (at 2105 cm$^{-1}$). The flask was cooled to 0° C. in an ice bath and was evacuated and back-filled with nitrogen five times. Under a stream of nitrogen, propargyl amine (1.0 equiv.) and sodium ascorbate (0.12 equiv.) were added sequentially. The flask was again evacuated and back-filled with nitrogen 5 times, then copper sulfate (0.05 equiv.) was added, followed by one additional evacuate/back-fill cycle. The reaction was stirred at 0° C. for 1 hour, then overnight at room temperature under nitrogen. FT-IR confirmed the disappearance of the organic azide peak at ~2106 cm$^{-1}$, indicating the reaction was complete. The thick green polymer ball was then directly dissolved in 0.01 N HCl and dialyzed using Spectra/Por® regenerated cellulose tubing with MWCO=3500 against 0.01 N HCl for two days, changing the dialysate 2 times. The polymer solution was then lyophilized until dry.

Example 2I: Carboxylate Functionalized Homopolymer

The precursor polymer utilized in this example was the 30.5 kDa polymer prepared according to the method described in Example 1A above.

A solution of the precursor poly(α-chloro-ε-caprolactone) in DMF (4 mL solvent/g polymer) was evacuated and back-filled with nitrogen five times. Sodium azide (NaN$_3$, 1.2 equiv.) was added and stirred overnight at room temperature via a magnetic stir bar. The presence of a new organic azide moiety was confirmed by FT-IR (at 2107 cm$^{-1}$). The flask was cooled to 0° C. in an ice bath and was evacuated and back-filled with nitrogen five times. Under a stream of nitrogen, 5-hexynoic acid (1.2 equiv.) and triethylamine (0.1 equiv.) were added sequentially. The flask was again evacuated and back-filled with nitrogen 5 times then copper iodide (0.1 equiv.) was added, followed by one additional evacuate/back-fill cycle. The reaction was stirred at 0° C. for 1 hour, then overnight at room temperature under nitrogen. FT-IR confirmed the disappearance of the organic azide peak at ~2106 cm$^{-1}$, indicating the reaction was complete. The contents of the flask were centrifuged, and the green supernatant was decanted off; the solid bed was washed with ample DMF, centrifuged again, and the supernatants combined. The DMF was largely removed via rotary evaporation, and the thick green oil was dissolved in a 12:1 mixture of water:triethylamine over many hours. The brownish green polymer solution was dialyzed using Spectra/Por® regenerated cellulose tubing with MWCO=3500 against deionized water for two days, changing the dialysate 3 times. The polymer solution was then lyophilized until dry. The green polymer was then dissolved in methanol and stirred with Marathon™ C cation exchange resin for 3 hours. The resin was filtered out, and the methanol was removed via rotary evaporation. To the polymer residue was added purified water, causing the polymer to precipitate. Ammonium hydroxide was added dropwise until the polymer went into solution; the final pH was 8. This solution was dialyzed for two days using MWCO=1000 Spectra/Por® dialysis tubing with water as the dialysate, replacing the dialysate 2 times. The polymer solution was then transferred to VirTis® jars, shell-frozen, and lyophilized until dry.

Example 2J: Guanidinium Functionalized Homopolymer

The precursor polymer utilized in this example was the 29.2 kDa polymer prepared according to the method described in Example 1A above.

To a solution of the precursor poly(α-chloro-ε-caprolactone) in N,N-dimethylformamide (DMF; 4 mL solvent/g polymer) was added sodium azide (NaN$_3$, 1.2 equiv.) with vigorous shaking on an orbital shaker. The vial was evacuated and back-filled with nitrogen five times and was shaken overnight at room temperature. The presence of a new organic azide moiety was confirmed by FT-IR (at 2106 cm$^{-1}$). Under a stream of nitrogen, the propargyl amide of arginine dihydrochloride and triethylamine (3 equiv.) were added sequentially. The flask was again evacuated and back-filled with nitrogen five times, and copper iodide (0.1 equiv.) was added. The reaction shook overnight under nitrogen, with close temperature monitoring over the first hour. FT-IR confirmed the disappearance of the organic azide moiety, indicating the reaction was complete. The contents of the vial were directly dissolved in 0.01N HCl until the solution was homogeneous and the pH was 3-4. The resulting solution was purified via dialysis using Spectra/Por® dialysis membrane tubing with MWCO=1000 Da against 0.01N HCl over 2 nights, changing the dialysate twice. The purified polymer solution was then transferred to a VirTis® jar, shell-frozen, and lyophilized until dry.

Example 2K

The precursor polymer utilized in this example was a 27.8 kDa Mw polymer prepared according to the method described in Example 1A above.

A solution of intermediate poly(α-chloro-ε-caprolactone) in DMF (4 mL solvent/g polymer) was evacuated and back-filled with nitrogen five times. Sodium azide (NaN$_3$, 1.2 equiv.) was added and stirred overnight at room temperature via a magnetic stir bar. The presence of a new organic azide moiety was confirmed by FT-IR (at 2106 cm$^{-1}$). Under a stream of nitrogen, propargyl amine (1.0 equiv.) and sodium ascorbate (0.12 equiv.) were added sequentially. The vial was again evacuated and back-filled with nitrogen 5 times, then copper sulfate (0.05 equiv.) was added, followed by one additional evacuate/back-fill cycle. The reaction stirred overnight under nitrogen. FT-IR confirmed the disappearance of the organic azide peak at ~2106 cm$^{-1}$, indicating the reaction was complete. The contents of the vial were centrifuged and the green supernatant decanted off; the solid bed was washed with ample DMF, centrifuged again, and the two supernatants combined. The DMF was largely removed via rotary evaporation, and the polymer was precipitated into water as a dark green semi-solid. The polymer was washed several times with fresh water and dried under vacuum overnight. The polymer was then dissolved in a 1:1 mixture of acetone/water and dialyzed using Spectra/Por® regenerated cellulose tubing with MWCO=1000 against 1:1 acetone/water. The dialysate was replaced after 5 hours, and dialysis continued overnight. The dialysate was then replaced with fresh water, and within minutes, polymer began to precipitate within the membrane. The solution was drained from the dialysis tube, shell-frozen at −6° C., and placed under vacuum. After 7 days, the polymer appeared to be dry, but was still dark green and insoluble in most common organic solvents. Assuming it was still impure, the polymer was dissolved in 0.01 N HCl, and the solution color began to change from dark green to amber almost immediately. This solution was dialyzed in MWCO=3500 dialysis tubing against 0.01 N HCl for two days, changing the dialysate 4 times. The polymer solution was then freeze-dried for two days until dry.

Example 2L

The precursor polymer utilized in this example was the 44.0 kDa Mw polymer prepared according to the method described in Example 1F above.

A solution of intermediate poly(α-chloro-ε-caprolactone-co-ε-caprolactone) in DMF (4 mL solvent/g polymer) was evacuated and back-filled with nitrogen five times. Sodium azide (NaN$_3$, 1.2 equiv.) was added and stirred overnight at room temperature via a magnetic stir bar. The presence of a new organic azide moiety was confirmed by FT-IR (at 2104 cm$^{-1}$). The flask was cooled to 0° C. in an ice bath and was evacuated and back-filled with nitrogen five times. Under a stream of nitrogen, propargyl alcohol (1.0 equiv.) and triethylamine (0.1 equiv.) were added sequentially. The flask was again evacuated and back-filled with nitrogen 5 times then copper iodide (0.1 equiv.) was added, followed by one additional evacuate/back-fill cycle. The reaction stirred at 0° C. for 1 hour, then overnight at room temperature under nitrogen. FT-IR confirmed the disappearance of the organic azide peak at ~2104 cm$^{-1}$, indicating the reaction was complete. The contents of the flask were centrifuged and the green supernatant decanted off; the solid bed was washed with ample DMF, centrifuged again, and the supernatants were combined. The DMF was largely removed via rotary evaporation, and the thick green oil was suspended in water. The flask was rotated in a warm water bath overnight, but the polymer did not dissolve. The water was poured off, and dissolution was attempted in chloroform, acetonitrile, tetrahydrofuran, and acetone. Each time, the polymer did not dissolve. The polymer eventually dissolved in NMP, and the solution was transferred to a beaker and treated with SiliaMetS® Thiol resin overnight. The resin was filtered out, and the polymer solution was transferred to Spectra/Por® dialysis tubing with MWCO=3500. The material dialyzed against NMP for 5 hours. The dialysate was discarded and replaced with purified water and dialyzed for 2 days. At this point, much of the polymer had begun to precipitate as a sticky substance and was leaking out of the dialysis membranes. What remained in the dialysis tubes was poured into a Virtis jar and lyophilized for 1 week until dry.

Example 2M

A solution of intermediate poly(α-chloro-ε-caprolactone) in THF (4 mL solvent/g polymer) was evacuated and backfilled with nitrogen five times. Sodium azide (NaN$_3$, 1.2 equiv.) was added and stirred overnight at room temperature via a magnetic stir bar, but no organic azide peak (2100 cm$^{-1}$) appeared. The reaction vial was transferred to a tumbler and tumbled to effect more efficient mixing, but still no azide peak appeared. The reaction was heated to 40° C. and shaken every hour by hand, but after 6 hours, no azide peak could be observed in the FT-IR. The reaction was discarded. While not intending to be bound by any particular theory, it was proposed that NaN$_3$ is not sufficiently soluble in THF to react with the chlorinated polymer.

Example 2N

To a solution of intermediate poly(α-chloro-ε-caprolactone) in THF (4 mL solvent/g polymer) was added purified water (10:1 THF:water). The vial was evacuated and backfilled with nitrogen five times. Sodium azide (NaN$_3$, 1.2 equiv.) was added and stirred overnight at room temperature via a magnetic stir bar, but no organic azide peak (~2100 cm$^{-1}$) appeared. The reaction vial was transferred to a tumbler and tumbled to effect more efficient mixing, but still no azide peak appeared; the sodium azide clumped together with the water and was not free-flowing in the reaction vial. The reaction was heated to 40° C. and shaken every hour by hand, but after 6 hours, no azide peak could be observed in the FT-IR. While not intending to be bound by any particular theory, it was proposed that the addition of more water to the reaction could have increased the solubility of sodium azide, however the polymer would likely have precipitated under those conditions. Therefore, the reaction was discarded.

Yields for Examples 2A to 2F ranged from 43% to 70%, depending on the nature of the "clicked" group and the method of purification.

Example 3: Complexation of Exenatide or GLP-1 Analog with Functionalized Complexation Polymers Complexation between exenatide or GLP-1 analog and functionalized complexation polymers was determined as set forth below.

Materials and Methods

Pharmaceutically active agents (exenatide and a GLP-1 analog) were combined as set forth below with an amine-functionalized homopolymer, an amine-functionalized copolymer, a carboxylate-functionalized homopolymer, and a guanidinium-functionalized homopolymer.

Preparation of either lyophilized (exenatide) or spray dried (GLP-1 analog) powder of complexed pharmaceutically active agents: 1.00 g of biologically active powder was placed in a 150 mL wide-mouth glass jar. 100 mL of 50 mM NH$_4$HCO$_3$ solution were added, and the mixture was stirred at 400 rpm for 30 min at room temperature (until it became a visibly clear solution).

100 mL of a 10 mg/mL solution of functionalized complexation polymer were then prepared by stirring 1.00 g of polymer in 100 mL of MilliQ water at 400 rpm (until it became a visibly clear solution).

The pharmaceutically active agent solution was combined with the functionalized complexation polymer solution at specific ratios as set forth below and monitored for precipitation. The combined materials were stirred for 30 min and then centrifuged in 50 mL Falcon™ tubes. The supernatant solution was removed for HPLC analysis to determine the quantity of free pharmaceutically active agent (not complexed). Where obtained, the resultant precipitate was resuspended in 50-100 mL of 50 mM NH$_4$HCO$_3$ solution and either lyophilized or spray dried as set forth below.

Lyophilization: Aliquots of 3 mL each of the bulk suspension obtained from the above step were transferred into 5 mL, type-BD Hypak™ glass syringes and lyophilized using the lyophilization cycle of a program P90 (optimized for each pharmaceutically active agent) to fit the steps provided with FTS lyophilizer (Dura Stop model), MP Stoppering Tray Dryer, Stone Ridge, N.Y. The lyophilization cycle is provided in Table 1 below. The final amount of complexed pharmaceutically active agent in each syringe is based on the appropriate dose of the pharmaceutically active agent. The syringes were seal pouched and stored in a −20° C. freezer until further study.

TABLE 1

Lyophilization Cycle

| STEP | SHELF TEMP (° C.) | TIME (HOUR) | Chamber pressure (mT) | Modified lyophilization protocol |
|---|---|---|---|---|
| FREEZING | PRECOOL @ −40 | | Not controlled | 1 hr prior to loading instrument was pre-cooled |
| | −40 | 2.0 | 3000 | Modified to fit the freezing steps available for FTS Lyophilizer |
| PRIMARY DRYING | −25 | 2.0 | 100 | |
| | −30 | 35.0 | | |
| SECONDARY DRYING | 25 | 2.0 | | Actual time was about 25 hours |
| | 25 | 10.0 | | |
| | 5 | 10.0 | 200 | Actual hold time was 8 hours |

Spray dry conditions:
Inlet temperature set up: 140° C.
Actual outlet temperature: 50-80° C.
Aspirator 100%
Pump: 13%
Nozzle Cleaner: 3-5 pulses The active content in the complexed powder was determined by running it on HPLC. The powder was dissolved in 2% phosphoric acid, and the clear solution was run on HPLC system.

Results

The results of the above complexation experiments are provided in part in Table 2 below. The complexation efficiency for exenatide and GLP-1 analog with an amine functionalized 50:50 copolymer (Example 2H) as a function of polymer to peptide ratio is provided in FIG. 1.

TABLE 2

| Pharmaceutically active agent | Complex | Ratio | Outcome |
|---|---|---|---|
| Exenatide | Amine functionalized homopolymer (Example 2G) | 47 mg of Peptide, 30 mg of PCL-NH$_2$ | No Precipitation |
| GLP-1 analog | Amine functionalized homopolymer (Example 2G) | 11.4 mg of Peptide, 2.7 mg of PCL-NH$_2$ | Instantaneous Precipitation (>99%) |
| Exenatide | Amine functionalized copolymer, 50:50 (Example 2H) | 47 mg of Peptide, 30 mg of PCL-NH$_2$ | Instantaneous Precipitation (~76%) |

TABLE 2-continued

| Pharmaceutically active agent | Complex | Ratio | Outcome |
|---|---|---|---|
| GLP-1 analog | Amine functionalized copolymer, 50:50 (Example 2H) | 11.4 mg of Peptide, 2.7 mg of PCL-NH$_2$ | Instantaneous Precipitation (>99%) |
| Exenatide | Carboxylate functionalized homopolymer (Example 2I) | 10 mg of Peptide, 20 mg of PCL-COOH | No Precipitation |
| GLP-1 analog | Carboxylate functionalized homopolymer (Example 2I) | 10 mg of Peptide, 20 mg of PCL-COOH | No Precipitation |
| Exenatide | Guanidinium functionalized homopolymer (Example 2J) | 10 mg of Peptide 20 mg of PCL-GuHCl | No Precipitation |
| GLP-1 analog | Guanidinium functionalized homopolymer (Example 2J) | 10 mg of Peptide 20 mg of PCL-GuHCl | No Precipitation |

Example 4: Complexation of Liraglutide with Functionalized Complexation Polymers Complexes between liraglutide and functionalized complexation polymers were prepared as set forth below.

Preparation of Lyophilized Powder of Complexed Liraglutide: 10 mg of Liraglutide was placed in a 20 mL wide-mouth glass jar. 1 mL of 50 mM NaHCO$_3$ (pH 9.5) solution was added, and the mixture was stirred at 400 rpm for 5 min at room temperature (until it became a visibly clear solution).

10 mg of Amine-functionalized complexation polymer ((Example 2C, prepared using 5.4 kDa precursor polymer) or (Example 2C, prepared using 11.4 kDa precursor polymer) or (Example 2C, prepared using 16.8 kDa precursor polymer) or (Example 2H, prepared using 17.2 kDa precursor polymer)) was then added to 1 mL of deionized water, and the mixture was stirred at 400 rpm (until it became a visibly clear solution). The weight ratio of peptide to polymer was 1:1.0. 1 mL of 10 mg/mL of amine functionalized polymer solution was added to liraglutide solution (ratio of 1:1), and the mixture was stirred at 400 rpm (until it formed a white precipitate). The suspension was stirred for 30 min before centrifuging the whole suspension in a 50 mL Falcon™ tube and removing the supernatant solution for HPLC analysis to determine the amount of free (not complexed) active. The resultant precipitate was resuspended in 50-100 mL of 50 mM NH$_4$HCO$_3$ solution and was lyophilized using the procedure in Example 3 above.

Example 5: Complexation of Liraglutide with Functionalized Complexation Polymer (AFCP-1)

Complexes between liraglutide and functionalized complexation polymers were prepared as set forth below.

Preparation of Lyophilized powder of Complexed Liraglutide: 92.3 mg of liraglutide were placed in a 20 mL wide-mouth glass jar. 6.5 mL of 50 mM NaHCO$_3$ (pH 9.5) solution were added, and the mixture was stirred at 400 rpm for 5 min at room temperature (until it became a visibly clear solution).

203.7 mg of Amine-functionalized complexation polymer, AFCP-1 (Example 2A, prepared using 15 kDa precursor polymer) were then added to 20 mL of deionized water, and the mixture was stirred at 400 rpm (until it became a visibly clear solution). The weight ratios of peptide to polymer were 1:0.3, 1:0.6, 1:0.8, 1:1.0, and 1:1.4, respectively. By way of example, 9.2 mL of 10 mg/mL AFCP-1 solution were added to liraglutide solution (ratio of 1:0.8), and the mixture was stirred at 400 rpm (until it formed a white precipitate). The suspension was stirred for 30 min before centrifuging the whole suspension in a 50 mL Falcon™ tube and removing the supernatant solution for HPLC analysis to determine how much of active was free (not complexed). The resultant precipitate was resuspended in 50-100 mL of 50 mM NH$_4$HCO$_3$ solution, and the mixture was lyophilized using the procedure in Example 3 above.

The complexation efficiencies for liraglutide with the amine functionalized PCL copolymer (AFCP-1) prepared in Example 2A as a function of polymer to peptide ratio are provided in FIG. 2.

Example 6: Complexation of Liraglutide with Functionalized Complexation Polymer (AFCP-2)

Complexes between liraglutide and functionalized complexation polymers were prepared as set forth below.

Preparation of Lyophilized Powder of Complexed Liraglutide: 107.3 mg of liraglutide were placed in a 60 mL wide-mouth glass bottle. 10.7 mL of 50 mM NH$_4$HCO$_3$ (pH 8.12) solution were added, and the mixture was stirred at 400 rpm for 30 min at room temperature (until it became a visibly clear solution).

276.4 mg of Amine-functionalized cornplexation polymer, AFCP-2 (Example 2A, 44 kD) were then added to 27.6 mL of deionized water, and the mixture was stirred at 400 rpm (until it became a visibly clear solution). The weight ratios of peptide to polymer were 1:0.3, 1:0.6, 1:0.8 and 1:1.0, respectively. By way of example, 10.73 mL of 10 mg/mL AFCP-2 solution were added to liraglutide solution (1:1 ratio), stirred at 400 rpm (until it formed a white precipitate) and kept at −10° C. overnight to complete the precipitation. The whole suspension was centrifuged in a 50 mL Falcon™ tube, and the supernatant solution was removed for HPLC analysis to determine how much of active was free (not complexed). The resultant precipitate was resuspended in 50-100 mL of 50 mM NH$_4$HCO$_3$ solution, and the mixture was vortexed and sonicated for 10 min before placing it in a lyophilizer for lyophilization using the procedure in Example 3 above.

The complexation efficiencies for liraglutide with the amine functionalized PCL copolymer AFCP-2 prepared in Example 2A as a function of polymer to peptide ratio are provided in FIG. 2.

Example 7 (Control)

Complexation of Liraglutide with Zn/Protamine

Complexes between liraglutide and Zn/Protamine were prepared as set forth below.

Preparation of Spray Dried Powder of Liraglutide Complexed with Zn/Protamine: 104.9 mg of liraglutide were placed in a 60 mL wide-mouth glass jar. 6.5 mL of 50 mM NH$_4$HCO$_3$ (pH 8.13) solution were added, and the mixture was stirred at 400 rpm for 30 min at room temperature (until it became a visibly clear solution).

100 mM Zinc acetate dehydrate solution was added to 20 mL of deionized water. The molar ratio of peptide to Zn was 1:2. 556 µL of 100 mM Zinc acetate solution were added to the liraglutide solution, and the mixture was stirred at 400 rpm (until it formed a white precipitate). Subsequently, 6.2 mL of 10 mg/mL protamine sulfate solution in water were added to the Zinc-Lira suspension. The suspension was allowed to stir for 30 min before centrifuging the whole suspension in a 50 mL Falcon tube and removing the supernatant solution for HPLC analysis to determine how much of active was free (not complexed). The resultant precipitate was resuspended in 50-100 mL of 50 mM $NH_4HCO_3$ solution and was spray-dried.

Spray dry conditions:
Inlet temperature set up: 140° C.,
Actual outlet temperature: 50-80° C.,
Aspirator 100%,
Pump: 13%,
Nozzle Cleaner: 3 to 5 pulses

Example 8: In Vitro Analysis of Exenatide Complexed with an Amine-Functionalized Copolymer Dissolution experiments were conducted as set forth below to determine the in vitro release of exenatide from a polymer complex including an amine functionalized 50:50 copolymer (Example 2H).

Materials and Methods 1.00 g of exenatide powder was placed in a 150 mL wide-mouth glass jar. 100 mL of 50 mM $NH_4HCO_3$ solution were added, and the mixture was stirred at 400 rpm for 30 min at room temperature (until it became a visibly clear solution).

100 mL of a 10 mg/mL solution of functionalized complexation polymer were then prepared by stirring 1.00 g of polymer in 100 mL of MilliQ water at 400 rpm (until it became a clear solution).

The exenatide solution was combined with the complexation polymer solution at specific ratios as set forth below and monitored for precipitation. The combined materials were stirred for 30 min and then centrifuged in 50 mL Falcon™ tubes. The supernatant solution was removed for HPLC analysis to determine the quantity of free pharmaceutically active agent (not complexed). The resultant precipitate was resuspended in 50-100 mL of 50 mM $NH_4HCO_3$ solution and lyophilized according to the method described in Example 3.

Lyophilized complex powder was suspended in 1 mL ammonium bicarbonate (50 mM).

For dissolution or in vitro release testing, PBS (Phosphate buffered saline) pH~7.4 was used as the medium, and the complexed powder was dispersed into the dissolution medium. For the dissolution study, a known amount of complexed powder was placed into 2 mL conical shaped polypropylene vials. 1 mL release medium (0.01M PBS at pH 7.4 equilibrated at 37° C.) was added gently to each vial such that the surface of the formulation was not disturbed. The samples were placed at 37° C./100 rpm in an orbital shaker. At every time point essentially all the release medium was removed and replaced by fresh solution. The amount of exenatide in solution at each time point was determined by HPLC.

Results

The in vitro dissolution profile for exenatide from the polymer complex is provided in FIG. 3. The in vitro dissolution rate for exenatide:PεCL-$NH_2$ was somewhat increased relative to the exenatide:$Zn^{2+}$:protamine complex prepared as described in Example 7.

Example 9: In Vitro Analysis of a GLP-1 Analog Complexed with Amine-Functionalized Copolymers Dissolution experiments were conducted as set forth below to determine the in vitro release of a GLP-1 analog from polymer complexes including an amine-functionalized 50:50 copolymer (Example 2H) and an amine-functionalized homopolymer (Example 2G), respectively.

Materials and Methods 1.00 g of GLP-1 analog powder was placed in a 150 mL wide-mouth glass jar. 100 mL of 50 mM $NH_4HCO_3$ solution were added, and the mixture was stirred at 400 rpm for 30 min at room temperature (until it became a visibly clear solution).

100 mL of a 10 mg/mL solution of functionalized complexation polymer were then prepared by stirring 1.00 g of polymer in 100 mL of MilliQ water at 400 rpm (until it became a clear solution).

The GLP-1 analog solution was combined with the complexation polymer solution at specific ratios as set forth below and monitored for precipitation. The combined materials were stirred for 30 min and then centrifuged in 50 mL Falcon™ tubes. The supernatant solution was removed for HPLC analysis to determine the quantity of free pharmaceutically active agent (not complexed). The resultant precipitate was resuspended in 50-100 mL of 50 mM $NH_4HCO_3$ solution and spray dried according to the method described in Example 3.

Spray dried complex powder was suspended in 1 mL ammonium bicarbonate (50 mM).

For dissolution or in vitro release testing, PBS (Phosphate buffered saline) pH~7.4 was used as the medium, and the complexed powder was dispersed into the dissolution medium. For the dissolution study, a known amount of complexed powder was placed into 2 mL conical shaped polypropylene vials. 1 mL release medium (0.01 M PBS at pH 7.4 equilibrated at 37° C.) was added gently to each vial such that the surface of the formulation was not disturbed. The samples were placed at 37° C./100 rpm in an orbital shaker. At every time point essentially all the release medium was removed and replaced by fresh solution. The amount of GLP-1 analog in solution at each time point was determined by HPLC.

Results

Figure 4:
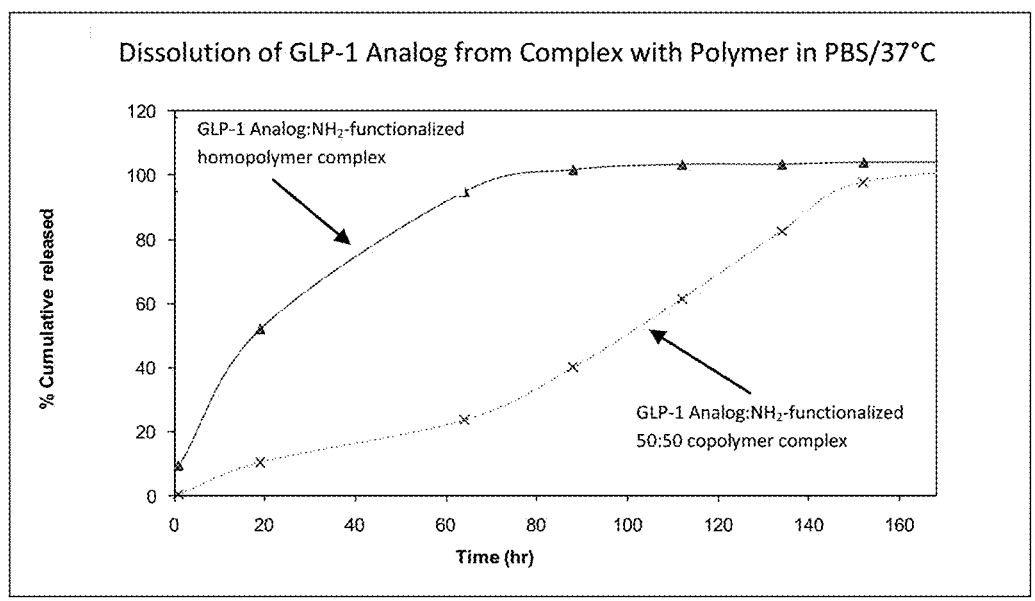
FIG. 4 is a graph showing the dissolution of a GLP-1 analog from a GLP-1:amine-functionalized 50:50 copolymer complex and a GLP-1:amine-functionalized homopolymer complex.

The in vitro dissolution profile for the GLP-1 analog from the polymer complexes is provided in FIG. 4. The in vitro dissolution rate for GLP-1 analog from the amine-functionalized homopolymer complex was increased relative to that for the amine-functionalized copolymer complex.

Example 10 (Control): In Vitro Analysis of Risperidone Mixed with a Carboxylate-Functionalized Copolymer Dissolution experiments were conducted as set forth below to determine the in vitro release from a mixture of risperidone and a carboxylate-functionalized 50:50 copolymer prepared as described in Example 2E. Although the risperidone and copolymer mixture was originally believed to involve a complex, further analysis indicated that the risperidone and copolymer precipitated separately at the relevant pH. This observation is mainly due to the limited solubilities of risperidone and the copolymer in the reaction mixture at pH~5.

Materials and Methods 1.00 g of a risperidone powder was placed in a 150 mL wide-mouth glass jar. 100 mL of 50 mM $NH_4COOCH_3$ solution were added, and the mixture was stirred at 400 rpm for 30 min at room temperature (until it became a visibly clear solution).

100 mL of a 10 mg/mL solution of functionalized polymer were then prepared by stirring 1.00 g of polymer in 100 mL of MilliQ water at 400 rpm (until it became a clear solution).

The pharmaceutically active agent solution was combined with the polymer solution at specific ratios as set forth below and monitored for precipitation. The combined materials were stirred for 30 min and then centrifuged in 50 mL Falcon™ tubes. The supernatant solution was removed for HPLC analysis to determine the quantity of free pharmaceutically active agent (not precipitated). The resultant precipitate was resuspended in 50-100 mL of 50 mM $NH_4COOCH_3$ solution and lyophilized according to the method described in Example 3.

Lyophilized powder was suspended in 1 mL ammonium bicarbonate (50 mM).

For dissolution or in vitro release testing, PBS (Phosphate buffered saline) pH~7.4 was used as the medium, and the powder was dispersed into the dissolution medium. For the dissolution study, a known amount of powder was placed into 2 mL conical shaped polypropylene vials. 1 mL release medium (0.01M PBS at pH 7.4 equilibrated at 37° C.) was added gently to each vial such that the surface of the formulation was not disturbed. The samples were placed at 37° C./100 rpm in an orbital shaker. At every time point essentially all the release medium was removed and replaced by fresh solution. The amount of risperidone in solution at each time point was determined by HPLC.

Results

Figure 5:
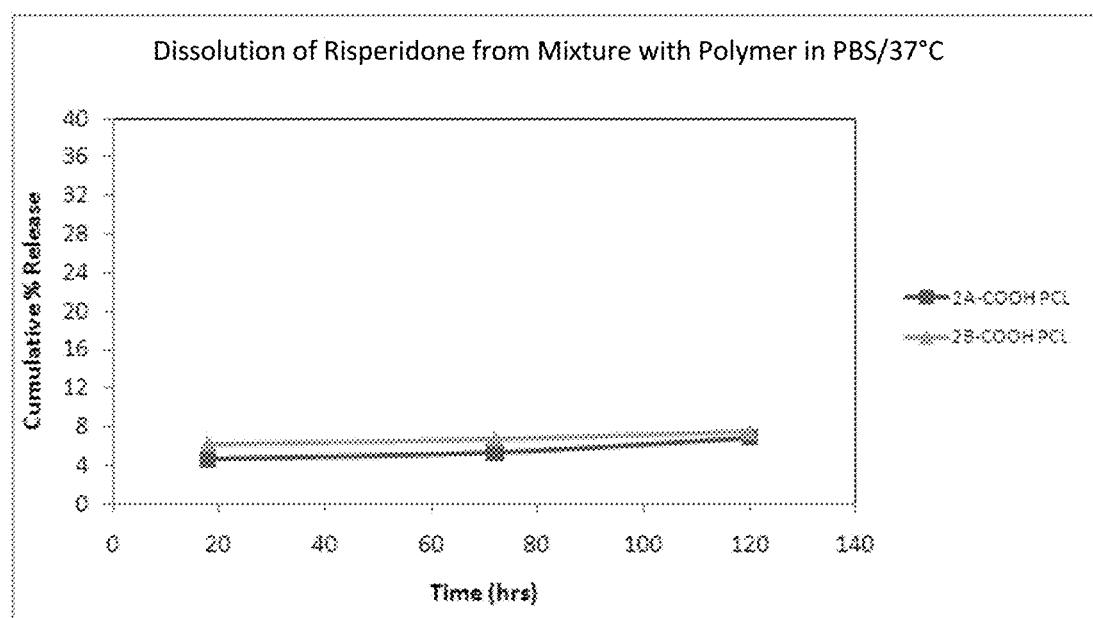
FIG. 5 is a graph showing the dissolution of risperidone from two different mixtures of risperidone and carboxylate-functionalized 50:50 copolymer in which the polymers have a molecular weight of 5.6 kDa ($M_w$ of precursor polymer) (2A) and 12 kDa ($M_w$ of precursor polymer) (2B), respectively.

The in vitro dissolution profile for risperidone from the mixture with the polymer is provided in FIG. 5. The in vitro dissolution rate was relatively low with a cumulative release of between 4% and 8% out to 130 hours. Most of the release from risperidone polymer mixture is due to slow dissolution of risperidone at pH 7.4

Example 11: In Vitro Analysis of Liraglutide Complexed with Amine-Functionalized Copolymers Dissolution experiments were conducted as set forth below to determine the in vitro release of liraglutide from a polymer complex including an amine-functionalized 50:50 copolymer.

Materials and Methods 1.00 g of liraglutide powder was placed in a 150 mL wide-mouth glass jar. 100 mL of 50 mM $NH_4HCO_3$ solution were added, and the mixture was stirred at 400 rpm for 30 min at room temperature (until it became a visibly clear solution).

100 mL of a 10 mg/mL solution of functionalized complexation polymer were then prepared by stirring 1.00 g of polymer in 100 mL of MilliQ water at 400 rpm (until it became a clear solution).

The liraglutide solution was combined with the complexation polymer solution at specific ratios as set forth below and monitored for precipitation. The combined materials were stirred for 30 min and then centrifuged in 50 mL Falcon™ tubes. The supernatant solution was removed for HPLC analysis to determine the quantity of free pharmaceutically active agent (not complexed). The resultant precipitate was resuspended in 50-100 mL of 50 mM $NH_4HCO_3$ solution and spray dried according to the method described in Example 3.

Complexes based on four different amine-functionalized 50:50 copolymers were tested as described below. Three of these copolymers were prepared according to Example 2C, the precursor polymers having molecular weights of 5.4 kDa, 11.4 kDa, and 16.8 kDa, respectively. In addition, a complex based on the amine-functionalized 50:50 copolymer (Example 2H, prepared using 16.0 kDa precursor polymer) was tested.

Spray dried complex powder was suspended in 1 mL ammonium bicarbonate (50 mM).

For dissolution or in vitro release testing, PBS (Phosphate buffered saline) pH~7.4 was used as the medium, and the complexed powder was dispersed into the dissolution medium. For the dissolution study, a known amount of complexed powder was placed into 2 mL conical shaped polypropylene vials. 1 mL release medium (0.01M PBS at pH 7.4 equilibrated at 37° C.) was added gently to each vial such that the surface of the formulation was not disturbed. The samples were placed at 37° C./100 rpm in an orbital shaker. At every time point essentially all the release medium was removed and replaced by fresh solution. The amount of liraglutide in solution at each time point was determined by HPLC.

Results

Figure 6:
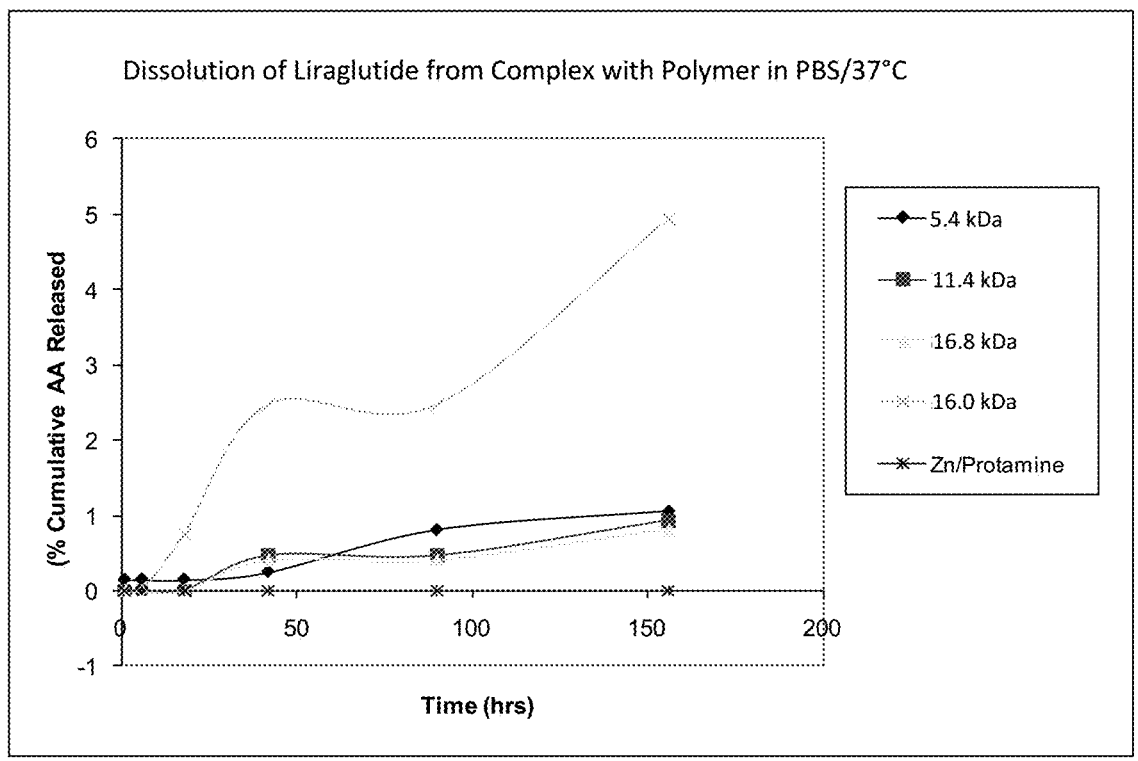
FIG. 6 is a graph showing the dissolution of liraglutide (AA) from several liraglutide:amine-functionalized 50:50 copolymer complexes. Dissolution of liraglutide from a liraglutide:Zn/Protamine complex is shown for comparison.

The in vitro dissolution profiles for liraglutide from the polymer complexes are provided in FIG. 6. The in vitro dissolution rates for liraglutide from the complexes based on copolymers prepared using the 5.4 kDa, 11.4 kDa, and 16.8 kDa precursor polymers were reduced relative to the dissolution rate for liraglutide from the complex based on the Example 2H copolymer prepared using the 16.0 kDa precursor polymer, but greater than that for liraglutide from a Zn:Protamine based complex prepared according to Example 7.

Example 12: In Vitro Analysis of Decitabine and AzaCytidine Complexed with an Amine-Functionalized Copolymer Dissolution experiments were conducted as set forth below to determine the in vitro release of decitabine and azacytidine from a polymer complex including an amine functionalized copolymer (Example 2H).

Materials and Methods 1.00 g of decitabine or azacytidine powder was placed in a 150 mL wide-mouth glass jar. 100 mL of 50 mM $NH_4HCO_3$ solution were added, and the mixture was stirred at 400 rpm for 30 min at room temperature (until it became a visibly clear solution).

100 mL of a 10 mg/mL solution of functionalized complexation polymer were then prepared by stirring 1.00 g of polymer in 100 mL of MilliQ water at 400 rpm (until it became a clear solution).

The decitabine or azacytidine solution was combined with the complexation polymer solution at specific ratios as set forth below and monitored for precipitation. The combined materials were stirred for 30 min and then centrifuged in 50 mL Falcon™ tubes. The supernatant solution was removed for HPLC analysis to determine the quantity of free pharmaceutically active agent (not complexed). The resultant precipitate was resuspended in 50-100 mL of 50 mM $NH_4HCO_3$ solution and lyophilized according to the method described in Example 3.

Lyophilized complex powder was suspended in 1 mL ammonium bicarbonate (50 mM).

For dissolution or in vitro release testing, PBS (Phosphate buffered saline) pH~7.4 was used as the medium, and the complexed powder was dispersed into the dissolution medium. For the dissolution study, a known amount of complexed powder was placed into 2 mL conical shaped polypropylene vials. 1 mL release medium (0.01M PBS at pH 7.4 equilibrated at 37° C.) was added gently to each vial such that the surface of the formulation was not disturbed. The samples were placed at 37° C./100 rpm in an orbital shaker. At every time point essentially all the release medium was removed and replaced by fresh solution. The amount of decitabine or azacytidine in solution at each time point was determined by HPLC.

Results

Figure 7:
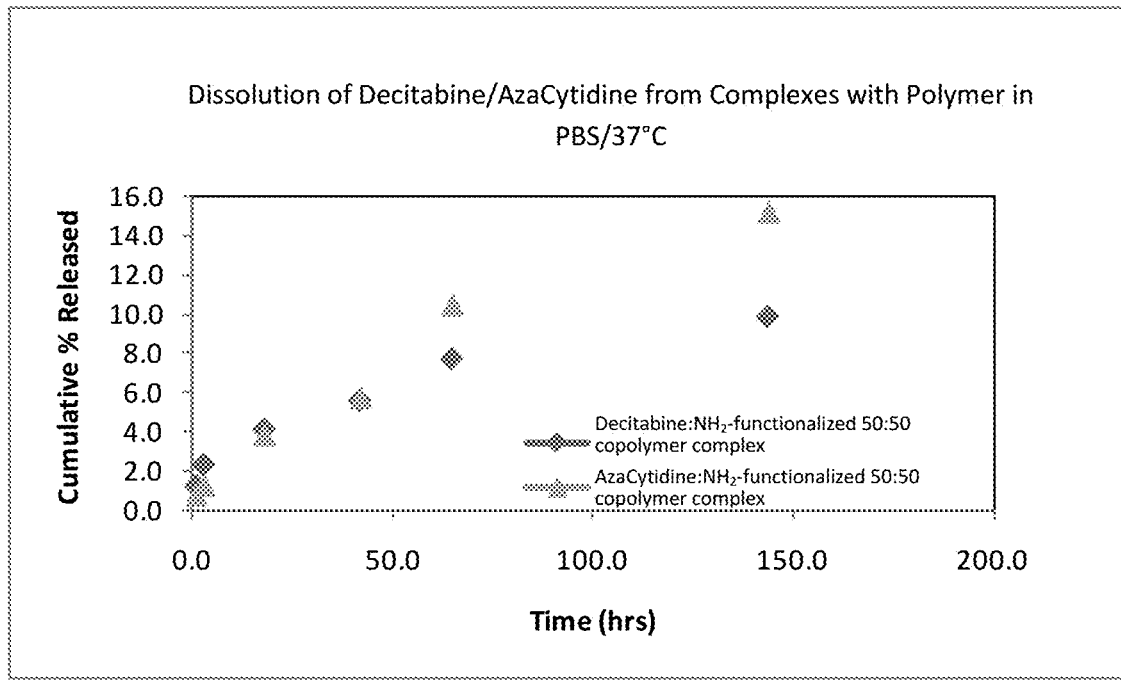
FIG. 7 is a graph showing the dissolution of decitabine and azacytidine from their respective complexes with amine-functionalized 50:50 copolymer.

The in vitro dissolution profiles for decitabine and azacytidine from the polymer complexes are provided in FIG. 7. However, under the tested conditions, decitabine and azacytidine are believed to be significantly degraded, possibly due to the relative instability of these compounds in water. Accordingly, the curves in FIG. 7 do not accurately represent the dissolution of intact decitabine and azacytidine from the polymer complex. Further analysis of decitabine complexation and dissolution was performed as described below in Example 13.

Example 13: Complexation of Decitabine with Functionalized Copolymers and Dissolution Analysis in Connection with Same Complexation of decitabine with various functionalized copolymers was attempted, and the resulting product was analyzed for in vitro dissolution characteristics as described below.

Materials and Methods

Decitabine powder (5 mg each) was dissolved in 100 μL of DMSO and mixed with different weight ratios (e.g., 5.0 mg for a 1:1 ratio) of complexation polymer in 1 mL of water for each of AFCP-1, AFCP-2, CFCP-1 and CFCP-4. The weight ratios of decitabine to polymer were 1:1, 1:1, 1:1 and 1:4, respectively.

After mixing each solution was vortexed for 20s and centrifuged to separate the precipitate from any un-reacted polymer and decitabine in the supernatant.

The precipitates were lyophilized to dryness. Known amounts of decitabine-polymer complex were dispersed in 1 mL of PBS and placed on an orbital shaker at 37° C./100 rpm. Dissolution of the complex was monitored over time, with complete replacement of the aqueous medium at every time point.

Results

Figure 9:
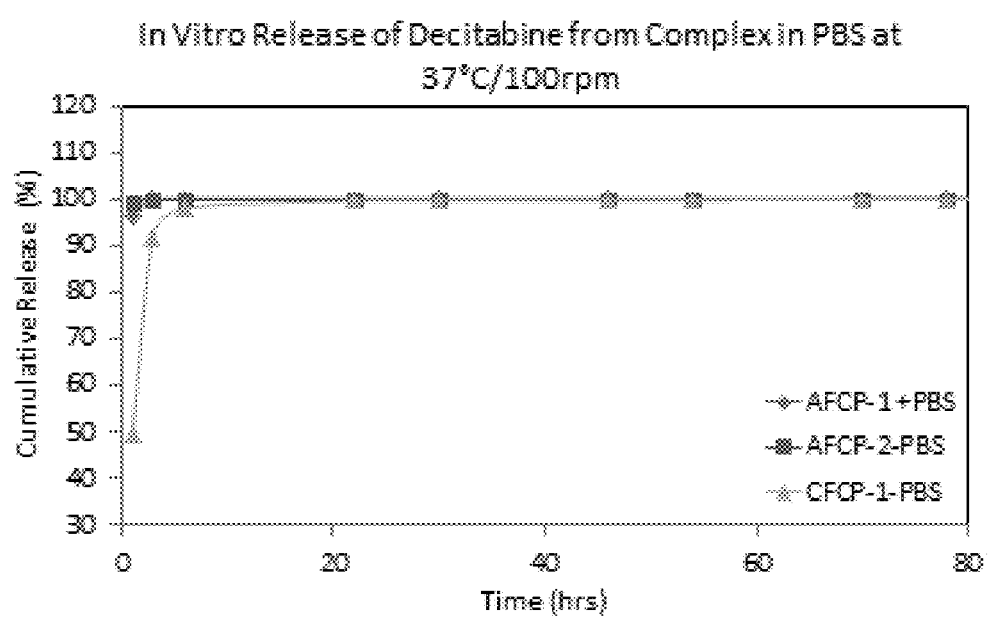
FIG. 9 is a graph showing the % cumulative release of decitabine for an attempted complexation with various amine or carboxylate functionalized copolymers.
Figure 10:
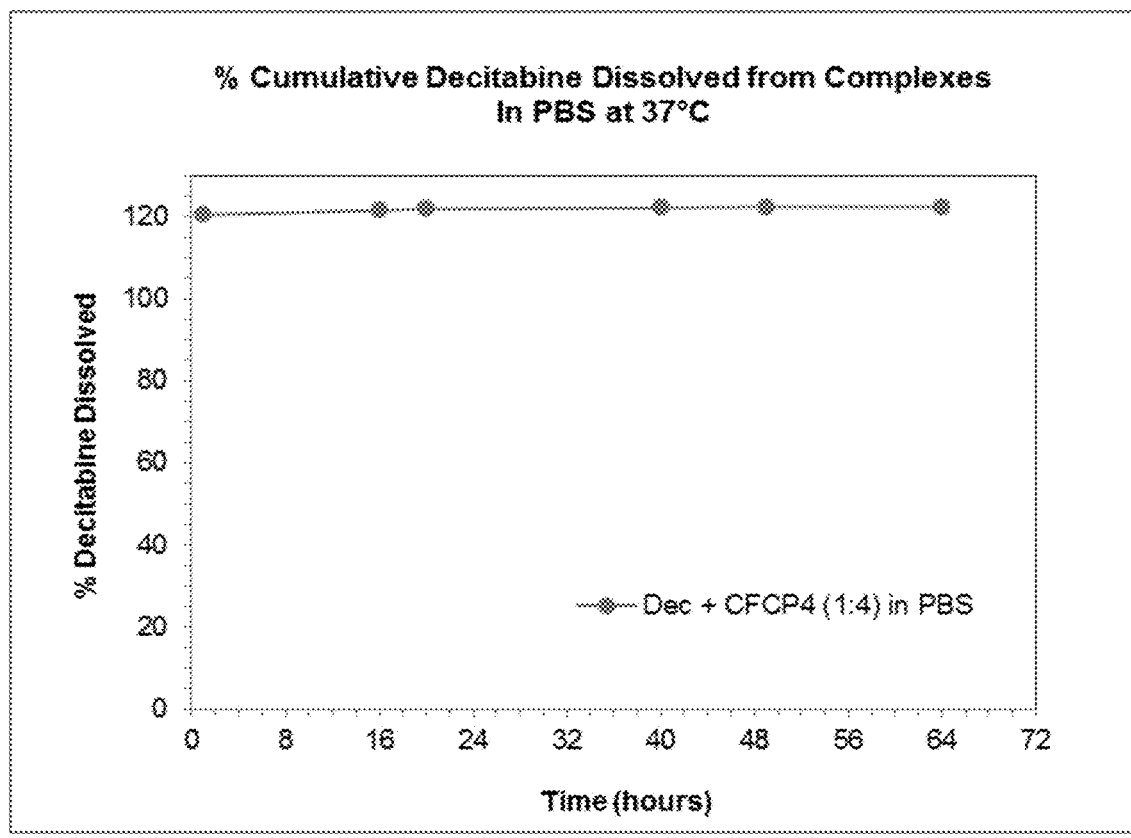
FIG. 10 is a graph showing the % cumulative release of decitabine from an attempted complexation with a carboxylate functionalized copolymer.

The tested complexation conditions resulted in relatively poor decitabine complex yields. The results of the dissolution assay are provided in FIGS. 9 and 10 and further demonstrate the unstable nature of decitabine complexed with both amine-functionalized and carboxyl-functionalized complexable polymers (AFCP and CFCP). While the AFCP-decitabine complexes dissolved faster in PBS at 37° C. than the CFCP-decitabine complex, both complexes were relatively unstable under the tested aqueous conditions.

Example 14: In Vitro Analysis of GLP-1 Analog Complexed with a Non-Click Chemistry-Based Functionalized Polymer Dissolution experiments were conducted as set forth below to determine the in vitro release of a GLP-1 analog from a polymer complex including a non-click chemistry based hydrazide-functionalized polymer ($NH_2$—NH—PLGA-NH—$NH_2$, 5 kDa) available from Polyscitech, West Lafayette, Ind.

Materials and Methods 1.00 g of GLP-1 analog powder was placed in a 150 mL wide-mouth glass jar. 100 mL of 50 mM $NH_4HCO_3$ solution were added, and the mixture was stirred at 400 rpm for 30 min at room temperature (until it became a visibly clear solution).

100 mL of a 10 mg/mL solution of functionalized complexation polymer were then prepared by stirring 1.00 g of polymer in 100 mL of MilliQ water at 400 rpm (until it became a clear solution).

The GLP-1 analog solution was combined with the complexation polymer solution at specific ratios as set forth below and monitored for precipitation. The combined materials were stirred for 30 min and then centrifuged in 50 mL Falcon™ tubes. The supernatant solution was removed for HPLC analysis to determine the quantity of free pharmaceutically active agent (not complexed). The resultant precipitate was resuspended in 50-100 mL of 50 mM $NH_4HCO_3$ solution and spray dried according to the method described in Example 3.

Spray dried complex powder was suspended in 1 mL ammonium bicarbonate (50 mM).

For dissolution or in vitro release testing, PBS (Phosphate buffered saline) pH~7.4 was used as the medium, and the complexed powder was dispersed into the dissolution medium. For the dissolution study, a known amount of complexed powder was placed into 2 mL conical shaped polypropylene vials. 1 mL release medium (0.01M PBS at pH 7.4 equilibrated at 37° C.) was added gently to each vial such that the surface of the formulation was not disturbed. The samples were placed at 37° C./100 rpm in an orbital shaker. At every time point essentially all the release medium was removed and replaced by fresh solution. The amount of GLP-1 analog in solution at each time point was determined by HPLC.

Results

Figure 8:
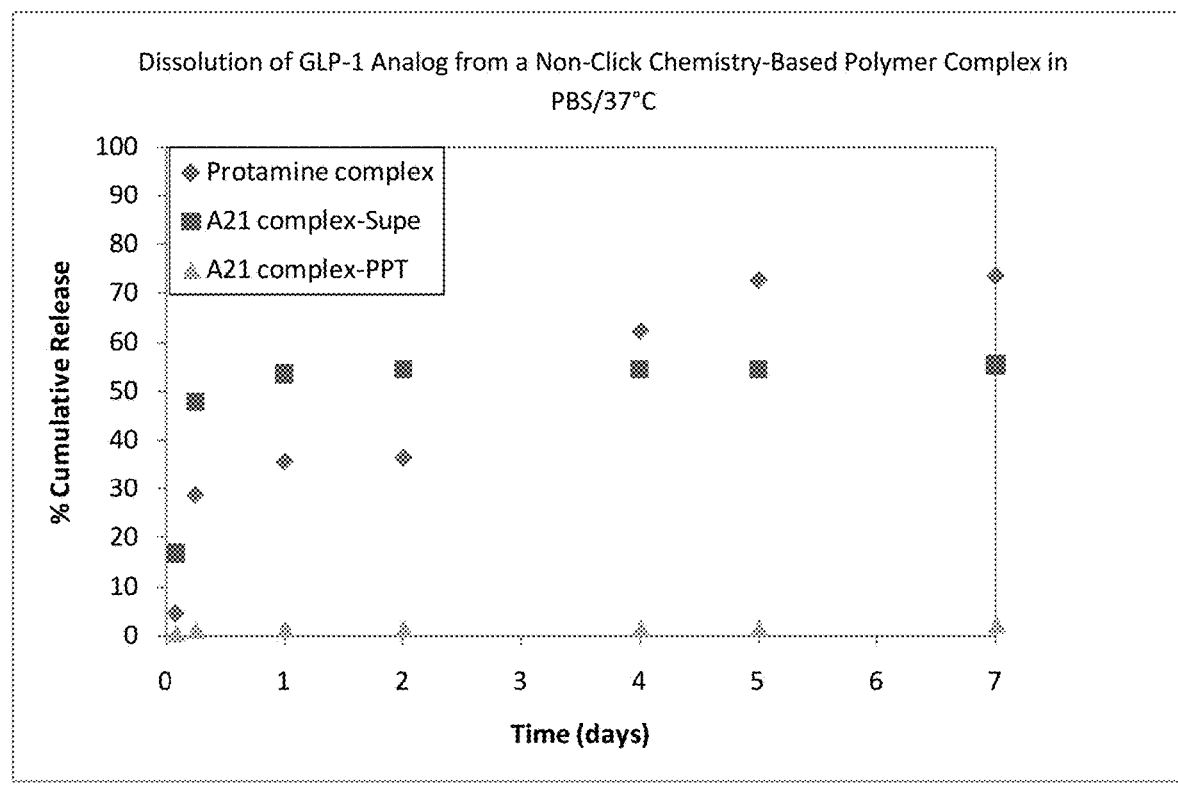
FIG. 8 is a graph showing the dissolution of the GLP-1 analog from a non-click chemistry-based complex (A21 complex-PPT). Dissolution of the GLP-1 analog from a protamine complex and a supernatant obtained following precipitation of the complex (A21 complex-Supe) is shown for comparison.

The in vitro dissolution profiles for the GLP-1 analog from the polymer complexes are provided in FIG. 8 along with the dissolution profile of the GLP-1 analog from a Zn:protamine complex prepared as described in Example 7. In FIG. 8, "SUPE"=supernatant and "PPT"=precipitate, where PPT represents polymer complexed with the GLP-1 analog and SUPE represents primarily GLP-1 analog+uncomplexed polymer. The PPT (complex) showed controlled release up to 7 days, while the SUPE showed a significantly more rapid release.

Example 15: In Vitro Analysis of Liraglutide Complexed with Additional Amine-Functionalized Copolymers Dissolution experiments were conducted as set forth below to determine the in vitro release of liraglutide from a polymer complex including an amine-functionalized copolymer.

Materials and Methods 1.00 g of liraglutide powder was placed in a 150 mL wide-mouth glass jar. 100 mL of 50 mM $NH_4HCO_3$ solution were added, and the mixture was stirred at 400 rpm for 30 min at room temperature (until it became a visibly clear solution).

100 mL of a 10 mg/mL solution of functionalized complexation polymer were then prepared by stirring 1.00 g of polymer in 100 mL of MilliQ water at 400 rpm (until it became a visibly clear solution). The functionalized complexation polymers were two different amine-functionalized PCL copolymers, which were prepared according to Example 2A (AFCP-1 and AFCP-2).

The liraglutide solution was combined with the complexation polymer solution at specific ratios as set forth below and monitored for precipitation. The combined materials were stirred for 30 min and then centrifuged in 50 mL Falcon™ tubes. The supernatant solution was removed for HPLC analysis to determine the quantity of free pharmaceutically active agent (not complexed). The resultant precipitate was resuspended in 50-100 mL of 50 mM $NH_4HCO_3$ solution and lyophilized according to the method described in Example 3.

Lyophilized complex powder was suspended in 1 mL ammonium bicarbonate (50 mM).

For dissolution or in vitro release testing, PBS (Phosphate buffered saline) pH~7.4 was used as the medium, and the complexed powder was dispersed into the dissolution medium. For the dissolution study, a known amount of complexed powder was placed into 2 mL conical shaped polypropylene vials. 1 mL release medium (0.01M PBS at pH 7.4 equilibrated at 37° C.) was added gently to each vial such that the surface of the formulation was not disturbed. The samples were placed at 37° C./100 rpm in an orbital shaker. At every time point essentially all the release medium was removed and replaced by fresh solution. The amount of liraglutide in solution at each time point was determined by HPLC.

Results

Figure 11:
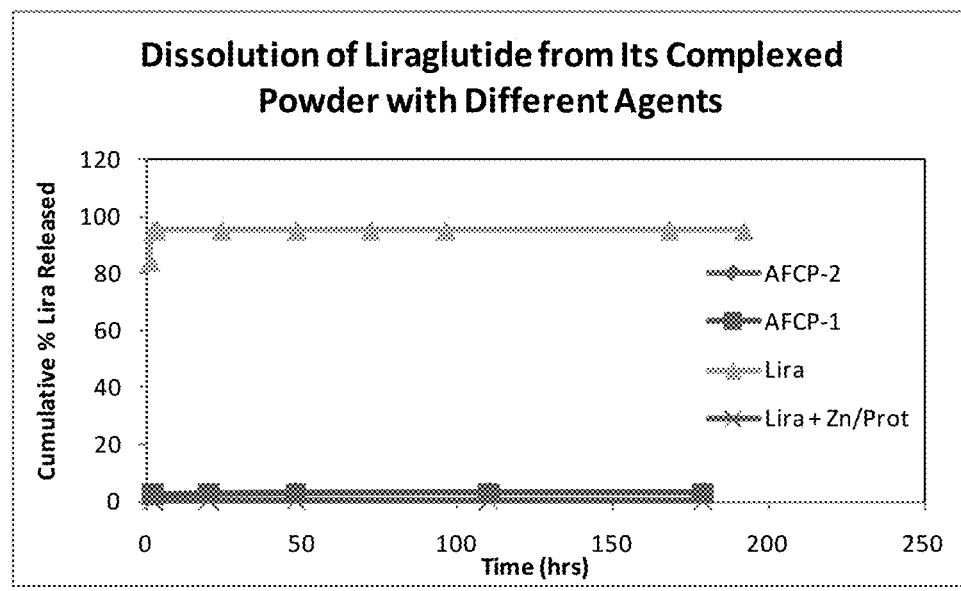
FIG. 11 is a graph showing the dissolution of liraglutide per se (Lira) and liraglutide from two different liraglutide:amine-functionalized 50:50 copolymer complexes (AFCP-1 and AFCP-2). The dissolution of liraglutide from a liraglutide:Zn/protamine complex (Lira+Zn/Prot) is shown for comparison.
Figure 12:
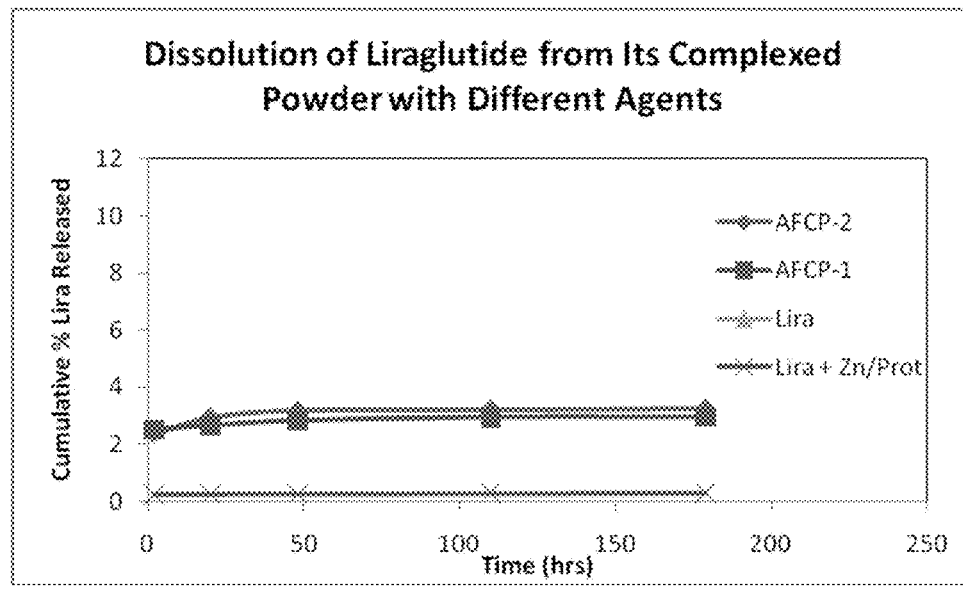
FIG. 12 is a graph showing the same data as FIG. 11 on a different scale.

The in vitro dissolution profiles for liraglutide from the polymer complexes are provided in FIGS. 11 and 12 relative to those for uncomplexed liraglutide (Lira) and liraglutide complexed with Zn:Protamine prepared in accordance with Example 7.

Example 16: In Vivo Analysis of Liraglutide Complexed with Amine-Functionalized Copolymers The following materials and methods were utilized in rat PK studies.

Materials and Methods 1.00 g of liraglutide powder was placed in a 150 mL wide-mouth glass jar. 100 mL of 50 mM $NH_4HCO_3$ solution were added, and the mixture was stirred at 400 rpm for 30 min at room temperature (until it became a visibly clear solution).

For each of two polymers, 100 mL of a 10 mg/mL solution of functionalized complexation polymer were then prepared by stirring 1.00 g of polymer in 100 mL of MilliQ water at 400 rpm (until it became a clear solution). The functionalized complexation polymers were two different amine-functionalized copolymers, which were prepared according to Example 2A (AFCP-1 and AFCP-2).

The liraglutide solution was combined with the complexation polymer solution at specific ratios as set forth below and monitored for precipitation. The combined materials were stirred for 30 min and then centrifuged in 50 mL Falcon™ tubes. The supernatant solution was removed for HPLC analysis to determine the quantity of free pharmaceutically active agent (not complexed). The resultant precipitate was resuspended in 50-100 mL of 50 mM $NH_4HCO_3$ solution and lyophilized according to the method described in Example 3.

Lyophilized complex powder was suspended in 1 mL ammonium bicarbonate (50 mM) or a vehicle comprising benzyl benzoate (BB)/poly (DL-Lactide) (Mw 15,100 Da) (PLA) in a 90/10 weight ratio, which was previously prepared by mixing BB and PLA in the desired ratio.

Liraglutide complexed powders were reconstituted in aqueous and non-aqueous vehicles prior to SC injections in rats. The following formulations were prepared for use in the in vivo experiments.

F1. aqueous solution of Liraglutide (Bachem) in 50 mM $NH_4HCO_3$

F2. aqueous slurry of Lira-Zn/Pro(1/2/0.3, m/m) in 50 mM $NH_4HCO_3$

F3. aqueous slurry of Lira-AFCP-1 (1/1 wt/wt) in 50 mM $NH_4HCO_3$

F4. aqueous slurry of Lira-AFCP-2 (1/1 wt/wt) in 50 mM $NH_4HCO_3$

F5. non-aqueous slurry of Lira-AFCP-1 (1/1 wt/wt) in BB/PLA (90/10)

F6. non-aqueous slurry of Lira-AFCP-2 (1/1 wt/wt) in BB/PLA (90/10)

F7. non-aqueous slurry of Lira-Zn/Pro(1/2/0.3, m/m) in BB/PLA (90/10)

The targeted dosing regimen for the in vivo experiments was as provided below in Table 3.

TABLE 3

| Group No. | No. and Sex of Animals | Treatment | Dose (mg/rat)* | Dose Volume (μL/rat)* | Dose Regimen and Route | Blood Collection (n = 5 per timepoint) |
|---|---|---|---|---|---|---|
| 1 | 5M | Liraglutide in Buffer (SQ Bolus) | 2 | 100 | Once, SC | Pre-dose (−24 hr), 15, 30 min, 1, 2, 4, 8, 12 hours, 1, 2, 3, 5, and 7 days |
| 2 | 5M | Liraglutide + Zn/Protamine in Buffer | Target = 2 | 100 | Once, SC | Pre-dose (−24 hr), 15, 30 min, 1, 2, 4, 8, 12 hours, 1, 2, 3, 5, and 7 days |
| 3 | 5M | Liraglutide + AFCP-1 in Buffer | Target = 2 | 100 | Once, SC | Pre-dose (−24 hr), 30 min, 1, 2, 4, 8, 12 hours, 1, 2, 3, 5, 7, 10, 14 and 29 days |
| 4 | 5M | Liraglutide + AFCP-2 in Buffer | Target = 2 | 100 | Once, SC | Pre-dose (−24 hr), 30 min, 1, 2, 4, 8, 12 hours, 1, 2, 3, 5, 7, 10, 14 and 29 days |

TABLE 3-continued

| Group No. | No. and Sex of Animals | Treatment | Dose (mg/rat)* | Dose Volume (μL/rat)* | Dose Regimen and Route | Blood Collection (n = 5 per timepoint) |
|---|---|---|---|---|---|---|
| 5 | 5M | Liraglutide + AFCP-1 + BB/PLA (90/10) | Target = 2 | 100 | Once, SC | Pre-dose (−24 hr), 30 min, 1, 2, 4, 8, 12 hours, 1, 2, 3, 5, 7, 10, 14 and 29 days |
| 6 | 5M | Liraglutide + AFCP-2 + BB/PLA (90/10) | Target = 2 | 100 | Once, SC | Pre-dose (−24 hr), 30 min, 1, 2, 4, 8, 12 hours, 1, 2, 3, 5, 7, 10, 14 and 29 days |
| 7 | 5M | Liraglutide + Zn/Protamine + BB/PLA (90/10) | Target = 2 | 100 | Once, SC | Pre-dose (−24 hr), 30 min, 1, 2, 4, 8, 12 hours, 1, 2, 3, 5, 7, 10, 14 and 29 days |

Buffer = 50 mM Ammonium Bicarbonate (pH ~8.1)
*The target 1 week dose of Liraglutide in human is 14 mg. The Victoza dose is 0.6-1.8 mg/day in 200-300 μL.

Results

Figure 13:
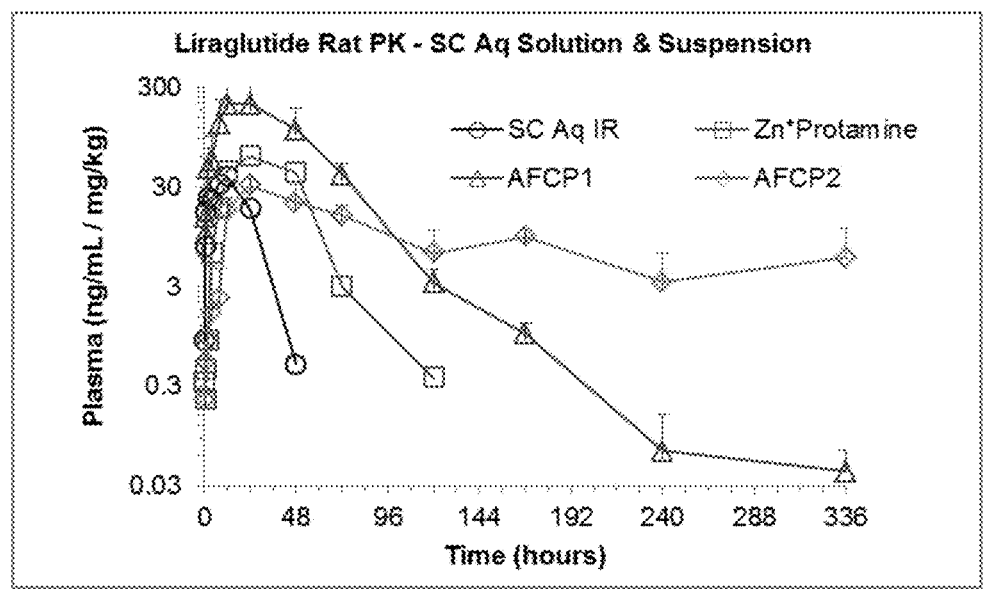
FIGS. 13 and 14 provide geometric mean data for the in vivo plasma concentration of liraglutide following administration of aqueous and BB:PLA vehicle suspended liraglutide complexes, respectively. Data for an aqueous solution of Liraglutide (Bachem) in 50 mM $NH_4HCO_3$, and a liraglutide:Zn/protamine complex in aqueous suspension or BB:PLA vehicle are provided for comparison as discussed in Example 16.
Figure 14:
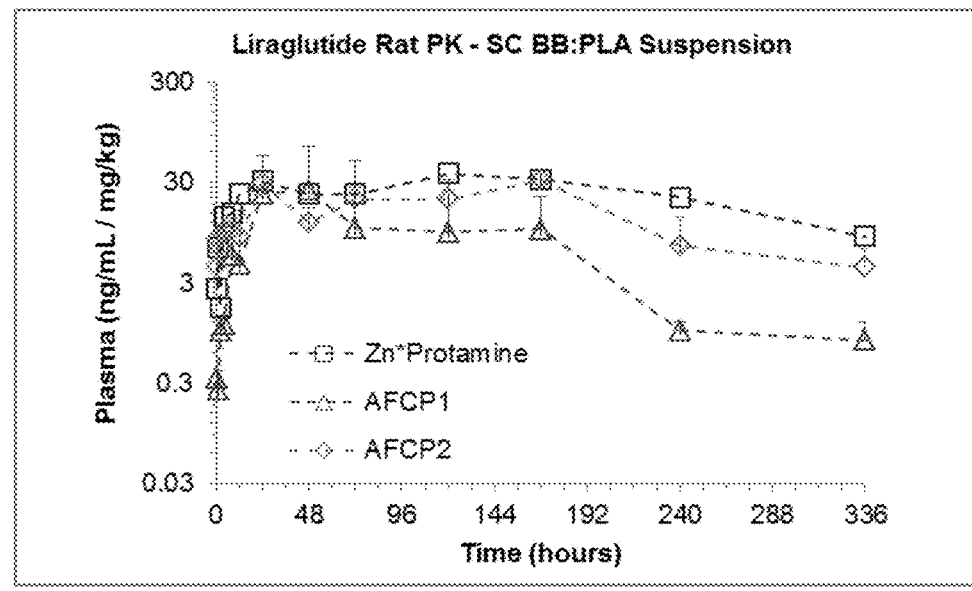

PK profiles for liraglutide complexed with amine-functionalized copolymers are provided in FIGS. 13 and 14. Dosing rates (mg/kg) varied across the test groups and among animals within a given test group. Accordingly, the plasma data provided in FIGS. 13 and 14 has been dose rate normalized to allow a fairer comparison of the performance of the formulations.

FIGS. 13 and 14 provide geometric mean data for the aqueous and BB:PLA vehicle suspensions of the liraglutide-counter-ion complexes, respectively. A clear progression emerges in the ability of the counter-ions to control the dissolution of the complexes in aqueous suspension: AFCP2>AFCP1>Zn2+/protamine (FIG. 13).

A progression also emerges in the contribution of the depot vehicle (or complex+vehicle) to overall control of peptide delivery: AFCP2<AFCP1<Zn2+/protamine (FIG. 14).

These data suggest preliminarily that an aqueous suspension of Lira:AFCP2 would be an adequate formulation for weekly delivery.

FIG. 14 emphasizes that the contribution the BB:la-PLA 90:10 (%, w/w) vehicle makes to the control of liraglutide delivery depends strongly on the particular complex suspended in the vehicle. The vehicle makes a strong contribution in the case of the $Zn^{2+}$/protamine complex, a moderate contribution for AFCP1, and a small (though important) contribution for AFCP2.

Figure 15:
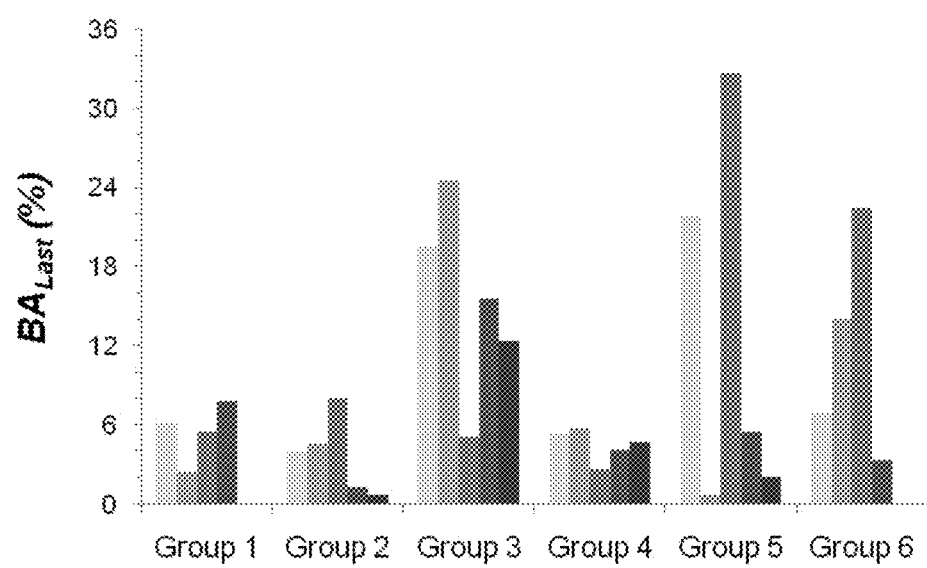
FIG. 15 is a graph showing the calculated BA of liraglutide from treatment Groups 1-6 of Example 16.

Using iv bolus data, the absolute BA of liraglutide obtained from these formulations was calculated up to the last time point for which quantifiable data were available for each animal. These results are provided in FIG. 15. Except for several animals, BA was generally <12%, which is consistent with results obtained in rats for several liraglutide formulations that comprised free peptide suspended in vehicles comprising sucrose acetate isobutyrate (absolute BA ranged from 5-28%).

Example 17: Local Tolerability Following Injection in Rats

Histopathological assessment of skins from the rats injected in Example 15 was performed using standard procedures. In general, there was minimal to mole inflammation present in the deep dermis in all groups at both the vehicle and active sites. This indicates that there is some nonspecific local multifocal inflammation induced by all of the vehicles and the test article. There were also low numbers of small granulomas present in the deep dermis in a few animals in most groups in both the vehicle and active groups. These are considered to be a resolving foreign body reaction or granuloma formulation reaction to the test and vehicle articles. This indicates that both the test article and the various vehicles alone or with test article will induce a small local foreign body reaction or granuloma formation particularly in Groups 3, 5, and 6.

Example 18: Preparation of Amine Functionalized Copolymer (30:70 Poly (α-Cl-ε-caprolactone-co-DL-lactide)) (AFCP-3)

The precursor polymer utilized in this Example was the 31.8 kDa polymer prepared according to the method described in Example 1B above.

A solution of the precursor poly(α-chloro-ε-caprolactone-co-DL-lactide) in DMF (4 mL solvent/g polymer) was evacuated and back-filled with nitrogen five times. Sodium azide ($NaN_3$, 1.2 equiv.) was added and stirred overnight at room temperature via a magnetic stir bar. The presence of a new organic azide moiety was confirmed by FT-IR (at 2107 $cm^{-1}$). The flask was cooled to 0° C. in an ice bath and was evacuated and back-filled with nitrogen five times. Under a stream of nitrogen, propargyl amine (1.0 equiv.) and sodium ascorbate (0.12 equiv.) were added sequentially. The flask was again evacuated and back-filled with nitrogen 5 times, then copper sulfate (0.05 equiv.) was added, followed by one additional evacuate/back-fill cycle. The reaction was stirred at 0° C. for 1 hour, then overnight at room temperature under nitrogen. FT-IR confirmed the disappearance of the organic azide peak at ~2107 $cm^{-1}$, indicating the reaction was complete. DMF was removed under vacuum, and the thick green polymer ball was then directly dissolved in 0.01 N HCl and dialyzed using regenerated cellulose tubing with MWCO=3500 against 0.01 N HCl for two days, changing the dialysate 2 times. The polymer solution was then freeze-dried until dry.

Analysis of the polymer indicated it was impure, so it was then redissolved in 0.01 N HCl. A metal scavenger (SiliaMetS® Thiol, 8 equiv.) was added to the polymer solution, and the mixture was stirred overnight. The scavenger was filtered out, and the resulting filtrate was purified via ultrafiltration in a stirred cell using 1.5 diavolumes of purified water as the dialysate. The purified polymer solution was then transferred to VirTis® jars, shell-frozen, and lyophilized until dry. The resulting amine functionalized copolymer had a $M_w$ of 31.8 kDa ($M_w$ of precursor polymer), a Pendant/Polymer ratio of $1.81 \times 10^{-3}$ mol/g, and a % substitution of ~30.

Example 19: Preparation of Amine Functionalized Copolymer (12.5:87.5 Poly(α-Cl-ε-caprolactone-co-DL-lactide)) (AFCP-4)

The precursor polymer utilized in this Example was the 5.6 kDa polymer prepared according to the method described in Example 1B above.

To a solution of the precursor poly(α-Cl-ε-caprolactone-co-DL-lactide) in N-methylpyrrolidone (NMP; 5 mL solvent/g polymer) was added sodium azide (NaN$_3$, 1.2 equiv.) with vigorous stirring via a magnetic stir bar. The flask was evacuated and back-filled with nitrogen five times and was stirred overnight at room temperature. The presence of a new organic azide moiety was confirmed by FT-IR (at ~2100 cm$^{-1}$). The flask was cooled to 0° C. in an ice bath and was evacuated and back-filled with nitrogen five times. Under a stream of nitrogen, propargyl amine (1.0 equiv.), triethylamine (0.1 equiv.), and copper iodide (0.1 equiv.) were added sequentially. The flask was again evacuated and back-filled with nitrogen. The exothermic reaction stirred at 0° C. for an hour; the ice bath was then removed, and the reaction continued to stir vigorously overnight under nitrogen. FT-IR confirmed the disappearance of the organic azide at ~2100 cm$^{-1}$, indicating the reaction was complete. The solids were filtered out of the reaction mixture and were washed with ample DMF. The filtrate was diluted with 0.01N hydrochloric acid until the solution was homogeneous and the pH was 4-5. A metal scavenger (SiliaMetS® Thiol, 8 equiv.) was added to the polymer solution, and the mixture was stirred overnight. The scavenger was filtered out, and the resulting filtrate was purified via ultrafiltration in a stirred cell using 1.5 diavolumes of purified water as the dialysate. The purified polymer solution was then transferred to VirTis® jars, shell-frozen, and lyophilized until dry.

The resulting amine functionalized copolymer had a $M_w$ of 5.6 kDa ($M_w$ of precursor polymer), a Pendant/Polymer ratio of $7.59 \times 10^{-4}$ mol/g, and a % substitution of 12.5. The resulting amine functionalized copolymer was marginally soluble in aqueous medium at pH 5.

Example 20: Preparation of Amine Functionalized Copolymer (25:60:15 Poly(α-Cl-ε-caprolactone-co-DL-lactide-co-glycolide)) (AFCP-5)

The precursor polymer utilized in this Example was the 17.5 kDa polymer prepared according to the method described in Example 1G above.

To a solution of the precursor poly(α-Cl-ε-caprolactone-co-DL-lactide-co-glycolide) in N-methylpyrrolidone (NMP; 5 mL solvent/g polymer) was added sodium azide (NaN$_3$, 1.2 equiv.) with vigorous stirring via a magnetic stir bar. The flask was evacuated and back-filled with nitrogen five times and was stirred overnight at room temperature. The presence of a new organic azide moiety was confirmed by FT-IR (at ~2100 cm$^{-1}$). The flask was cooled to 0° C. in an ice bath and was evacuated and back-filled with nitrogen five times. Under a stream of nitrogen, propargyl amine (1.0 equiv.), triethylamine (0.1 equiv.), and copper iodide (0.1 equiv.) were added sequentially. The flask was again evacuated and back-filled with nitrogen. The exothermic reaction stirred at 0° C. for an hour; the ice bath was then removed, and the reaction continued to stir vigorously overnight under nitrogen. FT-IR confirmed the disappearance of the organic azide at ~2100 cm$^{-1}$, indicating the reaction was complete. The solids were filtered out of the reaction mixture and were washed with ample DMF. The filtrate was diluted with 0.01N hydrochloric acid until the solution was homogeneous and the pH was 4-5. A metal scavenger (SiliaMetS® Thiol, 8 equiv.) was added to the polymer solution, and the mixture was stirred overnight. The scavenger was filtered out, and the resulting filtrate was purified via ultrafiltration in a stirred cell using 1.5 diavolumes of purified water as the dialysate. The purified polymer solution was then transferred to VirTis® jars, shell-frozen, and lyophilized until dry.

The resulting amine functionalized copolymer had a $M_w$ of 17.5 kDa ($M_w$ of precursor polymer), a Pendant/Polymer ratio of $1.48 \times 10^{-3}$ mol/g, and a % substitution of 25. The resulting amine functionalized copolymer was insoluble at any pH in purely aqueous media. It was purified as a solution in 1:1 Acetone/Water.

Example 21: Preparation of Carboxylate Functionalized Copolymer (CFCP-4)

The precursor polymer utilized in this Example was the 15.7 kDa polymer prepared according to the method described in Example 1E above.

A solution of the precursor poly(α-chloro-ε-caprolactone-co-ε-caprolactone) in NMP (4 mL solvent/g polymer) was evacuated and back-filled with nitrogen five times. Sodium azide (NaN$_3$, 1.2 equiv.) was added and stirred overnight at room temperature via a magnetic stir bar. The presence of a new organic azide moiety was confirmed by FT-IR (at 2105 cm$^{-1}$). The flask was cooled to 0° C. in an ice bath and was evacuated and back-filled with nitrogen five times. Under a stream of nitrogen, 5-hexynoic acid (1.2 equiv.) and triethylamine (1.3 equiv.) were added sequentially. The flask was again evacuated and back-filled with nitrogen 5 times and copper iodide (0.1 equiv.) was added, followed by one additional evacuate/back-fill cycle. The reaction was stirred at 0° C. for 2 hours, then overnight at room temperature under nitrogen. FT-IR confirmed the disappearance of the organic azide peak, indicating the reaction was complete. The reaction was filtered through a 0.45 μm hydrophilic PTFE membrane using a pressure filter; the solid bed was rinsed with an equal amount of NMP, and the resulting solution was slowly and carefully dissolved (with excessive foaming) in a saturated aqueous solution of sodium bicarbonate until the resulting pH=8. Activated charcoal (Norit® PK3-5, 4-14 mesh, granular; 1:1 carbon to polymer, w:w, ratio) was added and stirred vigorously for 5 hours as an attempt to decolorize the solution. The mixture was refrigerated overnight; it was then warmed to room temperature and filtered through a bed of celite and medium porosity filter paper. The filtrate was purified via TFF with a 3 kDa MWCO membrane cassette using deionized water as the dialysate. After purification for two days (3.5 diavolumes), the green color still remained. The solution was then treated with a metal scavenger (SiliaMetS® Thiol, 10 equiv.), and the color began to fade almost immediately; the mixture was stirred at room temperature overnight. The scavenger was filtered out, and the resulting filtrate was purified via tangential flow filtration (TFF) using a 3 kDa MWCO membrane and deionized water as the dialysate. Purification continued until the pH of the permeate solution was neutral; a total of 9 diavolumes of deionized water was used. The purified polymer solution was then transferred to VirTis® jars, shell-frozen, and lyophilized until dry.

The resulting carboxylate functionalized copolymer had a $M_w$ of 15.7 kDa ($M_w$ of precursor polymer), a Pendant/Polymer ratio of $2.64 \times 10^{-3}$ mol/g, and a % substitution of 44.

Example 22: Preparation of Carboxylate Functionalized Copolymer (CFCP-5)

The precursor polymer utilized in this Example was the 44.0 kDa polymer prepared according to the method described in Example 1F above.

A solution of the precursor poly($\alpha$-chloro-$\varepsilon$-caprolactone-co-$\varepsilon$-caprolactone) in NMP (4 mL solvent/g polymer) was evacuated and back-filled with nitrogen five times. Sodium azide ($NaN_3$, 1.2 equiv.) was added and stirred overnight at room temperature via a magnetic stir bar. The presence of a new organic azide moiety was confirmed by FT-IR (at 2104 $cm^{-1}$). The flask was cooled to 0° C. in an ice bath and was evacuated and back-filled with nitrogen five times. Under a stream of nitrogen, 5-hexynoic acid (1.2 equiv.) and triethylamine (0.1 equiv.) were added sequentially. The flask was again evacuated and back-filled with nitrogen 5 times and copper iodide (0.1 equiv.) was added, followed by one additional evacuate/back-fill cycle. The reaction was stirred at 0° C. for 3 hours, then overnight at room temperature under nitrogen. FT-IR showed the organic azide peak at ~2104 $cm^{-1}$ was less intense, but was still present. Triethylamine (1.1 equiv.) was added; the flask was evacuated/back-filled with nitrogen 3 times; and copper iodide (0.01 equiv.) was again added. After stirring for three additional days, FT-IR confirmed the disappearance of the organic azide peak, indicating the reaction was complete. The reaction was filtered through a 0.45 µm hydrophilic PTFE membrane using a pressure filter; the solid bed was rinsed with an equal amount of NMP, and the resulting solution was slowly and carefully dissolved (with excessive foaming) in a saturated aqueous solution of sodium bicarbonate until the resulting pH=8. A metal scavenger (SiliaMetS® Thiol, 10 equiv.) was added to the polymer solution, and the mixture was stirred overnight. The scavenger was filtered out, and the resulting filtrate was purified via tangential flow filtration (TFF) using a 3 kDa MWCO membrane and deionized water as the dialysate. Purification continued until the pH of the permeate solution was neutral; a total of 15 diavolumes of deionized water was used. The purified polymer solution was then transferred to VirTis® jars, shell-frozen, and lyophilized until dry.

The resulting carboxylate functionalized copolymer had a $M_w$ of 44.0 kDa ($M_w$ of precursor polymer), a Pendant/Polymer ratio of $2.7 \times 10^{-3}$ mol/g, and a % substitution of 44.

Example 23: Complexation of Human Growth Hormone (hGH) with Amine Functionalized Copolymers and Dissolution Analysis of Complexed hGH HGH was complexed with various amine functionalized copolymers and analyzed for in vitro dissolution characteristics as described below.

Materials and Methods

Recombinant hGH powder (5 mg each) was dissolved in 1 mL of 50 mM Ammonium Bicarbonate (pH~8.1) and mixed with different weight ratios (2.5, 5, 10 and 20 mg) (1:0.5, 1:1, 1:2 and 1:4) of complexable polymers including AFCP-2, AFCP-3 and AFCP-5 in 1 mL of water.

After mixing, each solution was vortexed for 20 sec and centrifuged to remove supernatant containing unreacted polymer and hGH from the precipitate.

The precipitate was lyophilized until dry and known amounts of hGH complexed with polymer were dispersed in 1 mL of PBS at 37° C./100 rpm in an orbital shaker to assess dissolution. The PBS media was replenished at every time point.

Results

Figure 16:
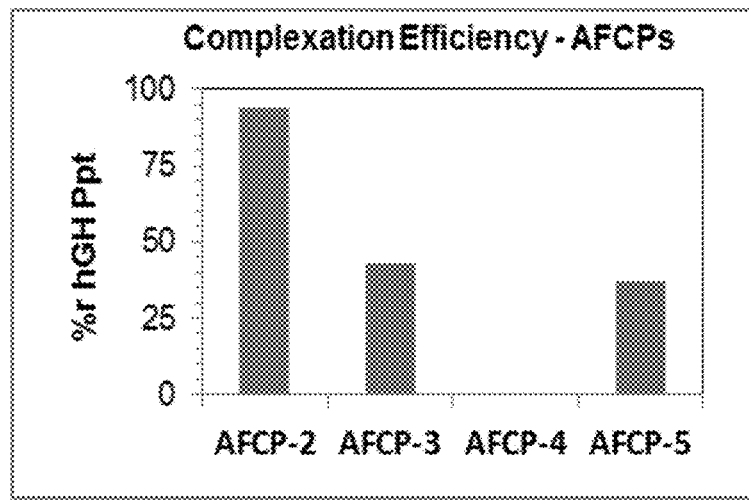
FIG. 16 is a graph showing the complexation efficiency of each of AFCP-2, AFCP-3, AFCP-4, and AFCP-5 amine functionalized copolymers with recombinant human growth hormone (rhGH).
Figure 17:
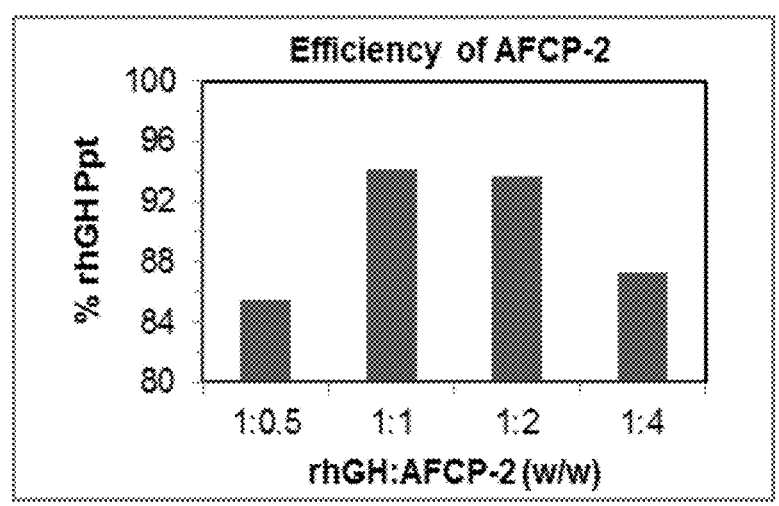
FIG. 17 is a graph showing the complexation efficiency for AFCP-2 with rhGH at various weight ratios.

The results of the complexation reactions are shown in FIGS. 16 and 17. As shown, AFCP-2 exhibited the highest complexation efficiency with respect to hGH with over 90% of the hGH precipitated. AFCP-3 and AFCP-5 each exhibited a complexation efficiency between 30% and 50%. As shown, AFCP-4 did not form a complex under these conditions. Without intending to be bound by any particular theory, it is possible that the relatively low level of amine substation in AFCP-4 was insufficient for complexation with hGH. FIG. 17 shows the complexation efficiency of AFCP-2 with hGH at various w/w ratios. As shown, ratios of 1:1 and 1:2 resulted in over 92% of the hGH precipitated.

Figure 18:
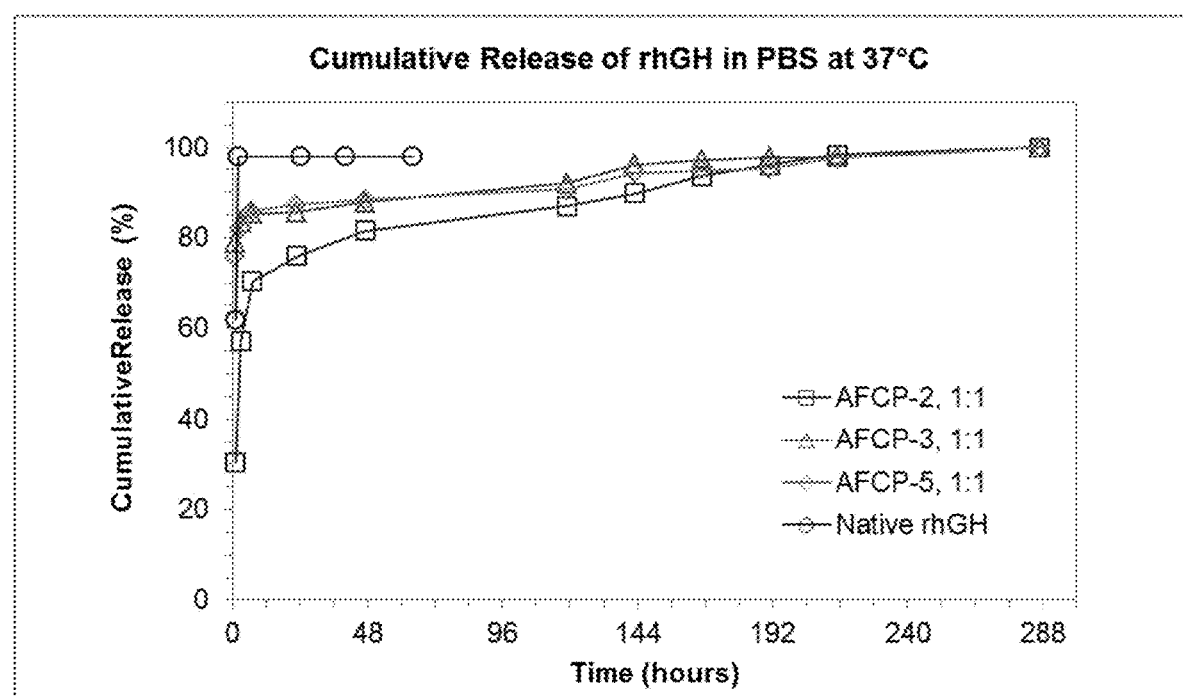
FIG. 18 is a graph showing the dissolution of rhGH from AFCP-2, AFCP-3 and AFCP-5 complexes. Native rhGH is plotted as a control.

The results of the in vitro dissolution analysis are provided in FIG. 18. As shown, each of the AFCP-2-hGH, AFCP-3-hGH, and AFCP-5-hGH complexes provided for lower initial release of hGH (within the first 24 hours) relative to native hGH, with the AFCP-2-hGH complex providing a significantly lower initial release than AFCP-3-hGH or AFCP-5-hGH complex.

Example 24: Complexation of Liraglutide with Amine Functionalized Copolymers AFCP-2 and AFCP-3

Liraglutide was complexed with AFCP-2 and AFCP-3 amine functionalized copolymers at different weight ratios and complexation efficiency was determined.

Materials and Methods

Liraglutide (5 mg) was dissolved in 1 mL of 50 mM $NH_4HCO_3$ (pH 8.1) and mixed with AFCP-2 or AFCP-3 in 1 mL of water, at weight ratios 1:0.25, 1:0.5, 1:1 and 1:2. AFCP-2 is 45% functionalized, $M_w$~44 kD PCL; AFCP-3 is 30% functionalized, 30:70 PCLL, $M_w$~32 kD.

After mixing, each preparation was vortexed for 20s and centrifuged to separate supernatant containing un-reacted peptide and polymer from the precipitate. Supernatant samples were diluted 10× in water to quantify un-reacted peptide via RP-HPLC.

Results

Figure 19:
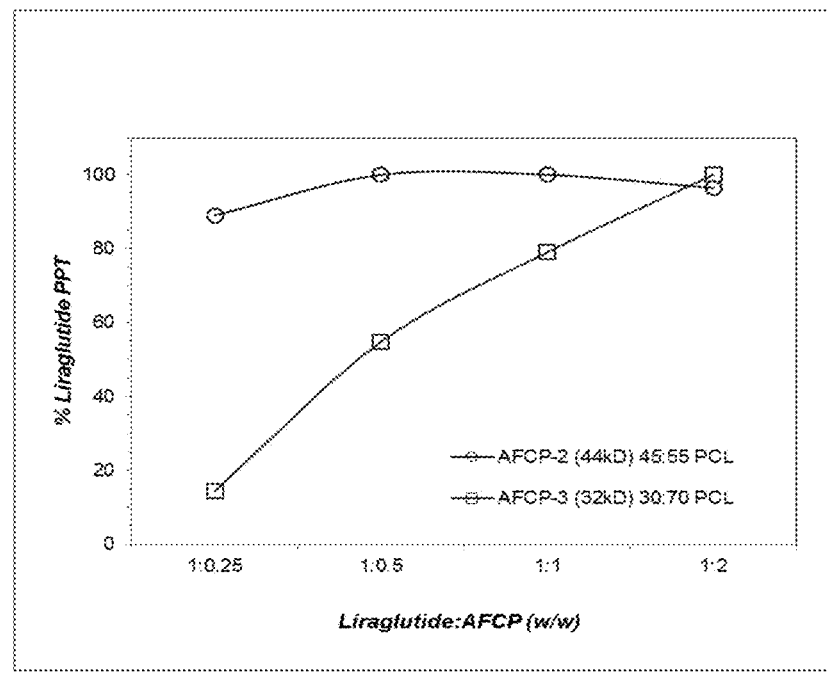
FIG. 19 is a graph showing the complexation efficiency of AFCP-2 amine functionalized copolymer with Liraglutide at various w/w ratios.
Figure 20:
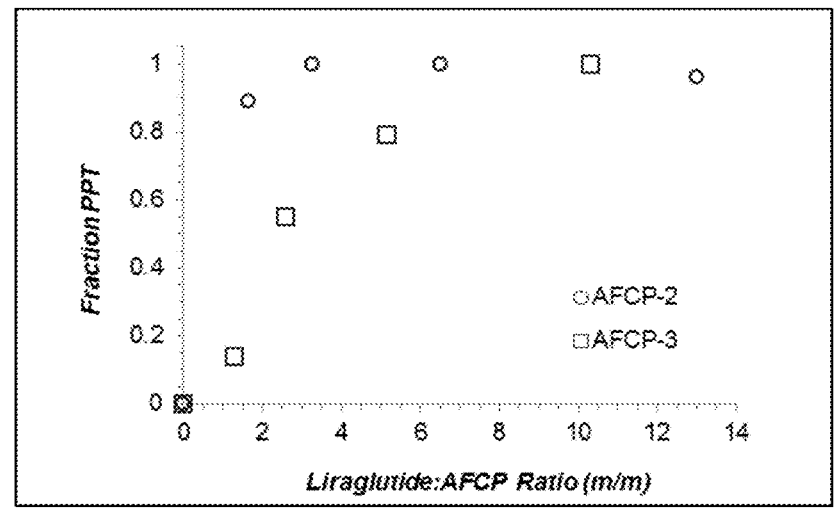
FIG. 20 is a graph showing the fraction precipitated for the complexation of Liraglutide with AFCP-2 and AFCP-3 based on the molar ratio Liraglutide to AFCP-2 and AFCP-3.

The results of the complexation reactions are shown in FIGS. 19 and 20. FIG. 19 shows the % Liraglutide precipitated using AFCP-2 and AFCP-3 at the various weight ratios. As shown, the % Liraglutide precipitated using AFCP-2 was relatively constant across the different weight ratios, while the complexation efficiency of AFCP-3 increased with an increase in the relative amount of the AFCP-3 polymer. FIG. 20 shows the fraction precipitated based on the molar ratio Liraglutide to AFCP-2 and AFCP-3.

Example 25: Complexation of Immunoglobulin G (IgG) with Amine Functionalized Copolymers and Dissolution Analysis of Complexed IgG IgG was complexed with various amine functionalized copolymers and analyzed for in vitro dissolution characteristics as described below.

Materials and Methods

IgG powder (5 mg each) was dissolved in 1 mL of 50 mM $NH_4HCO_3$ (pH 8.1) and mixed with a different amine functionalized PCL polymer (AFCP-2, AFCP-3, AFCP-4 and AFCP-5) at 5 mg in 1 mL of water.

After mixing, each solution was vortexed for 20 sec and centrifuged to remove supernatant containing unreacted polymer and IgG from the precipitate.

The precipitate was lyophilized until dry and known amounts of IgG-polymer complex were dispersed in 1 mL of PBS at 37° C./100 rpm in an orbital shaker to assess dissolution. The PBS media was replenished at every time point.

Results

Figure 21:
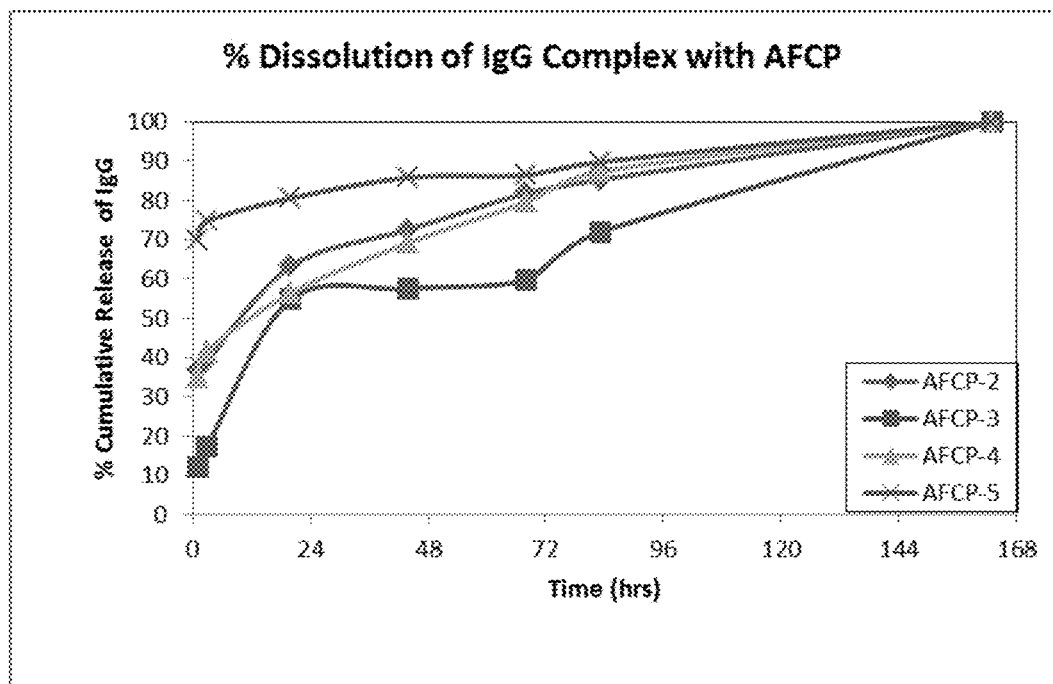
FIG. 21 is a graph showing the dissolution of IgG from AFCP-2, AFCP-3, AFCP-4, and AFCP-5 complexes.

The results of the dissolution assays are shown in FIG. 21. Initial release of IgG (within the first 24 hours) was lowest for AFCP-3. Initial release of IgG for AFCP-2 and AFCP-4 complexes was higher than for AFCP-3, but lower than for AFCP-5, which showed a relatively high initial release of IgG (about 80% cumulative release within the first 24 hours).

Example 26: Complexation of a Somatostatin Analogue with a Carboxylate Functionalized Copolymer and Dissolution Analysis of Complexed Somatostatin Analogue A synthetic somatostatin analogue was complexed with a carboxylate functionalized copolymer (CFCP-1) and analyzed for in vitro dissolution characteristics as described below.

Materials and Methods

Somatostatin analogue powder (5 mg) was dissolved in 1 mL of $NH_4HCO_3$ and mixed 1:1 (w/w) with COOH-functionalized CFCP-1(50% pendant, Mw~15.9 kDa PCL ($M_w$ of precursor polymer)) in 1 mL of water.

After mixing, each preparation was vortexed for 20 sec and centrifuged to remove supernatant containing unreacted polymer and somatostatin analogue from the precipitate.

The precipitate was lyophilized until dry and a known amount of somatostatin analogue-CFCP-1 complex was suspended in 1 mL of PBS at 37° C./100 rpm in an orbital shaker to assess dissolution. The PBS media was replenished at every time point.

Results

Figure 22:
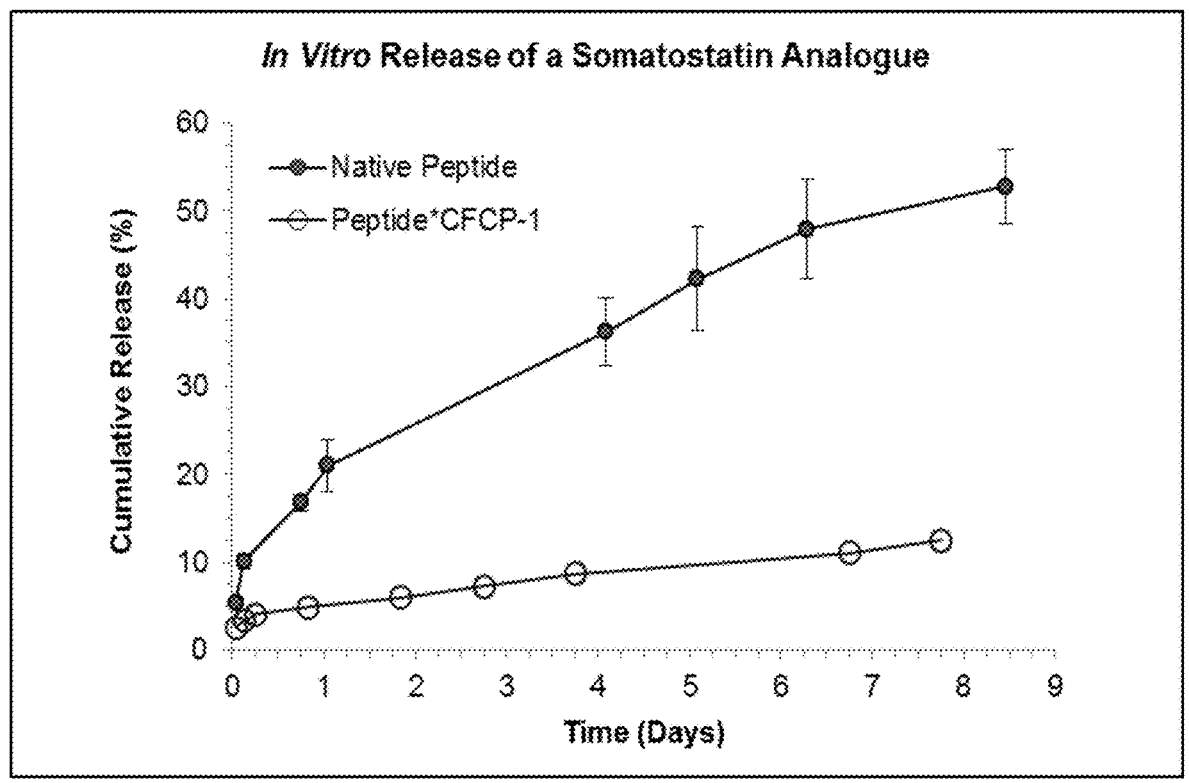
FIG. 22 is a graph showing the dissolution of somatostatin analogue from a CFCP-1 carboxylate functionalized copolymer complex.

The results of the dissolution assay are shown in FIG. 22, which compares the % cumulative release of the somatostatin analogue from the somatostatin analogue-CFCP-1 complex relative to the somatostatin analogue alone in powder form. As seen in FIG. 22, the somatostatin analogue-CFCP-complex powder dissolves in PBS at a slower rate than the somatostatin analogue alone in powder form, making the complex a viable option for an extended release depot, e.g., for the delivery of a somatostatin analogue over a one month period.

Example 27: Complexation of Cromolyn with a Amine Functionalized Copolymers and Dissolution Analysis of Complexed Cromolyn Cromolyn was complexed with various amine functionalized copolymers and analyzed for in vitro dissolution characteristics as described below.

Materials and Methods

Cromolyn powder (5 mg each) was dissolved in 1 mL of Ammonium Acetate and mixed with 5.0 mg (1:1) of complexable polymer (AFCP-2, AFCP-3, AFCP-4 and AFCP-5) in 1 mL of water.

After mixing, each preparation was vortexed for 20s, then centrifuged to separate supernatant, containing un-reacted cromolyn and polymer, from the precipitate.

Recovered precipitate was then lyophilized to dryness, and its dissolution rate in aqueous medium assessed: A known amount of Cromolyn-AFCP complex was suspended in 1 mL of PBS at 37° C. on an orbital shaker. The % cumulative release of cromolyn over time was followed, with complete medium replacement at every time point.

Results

Figure 23:
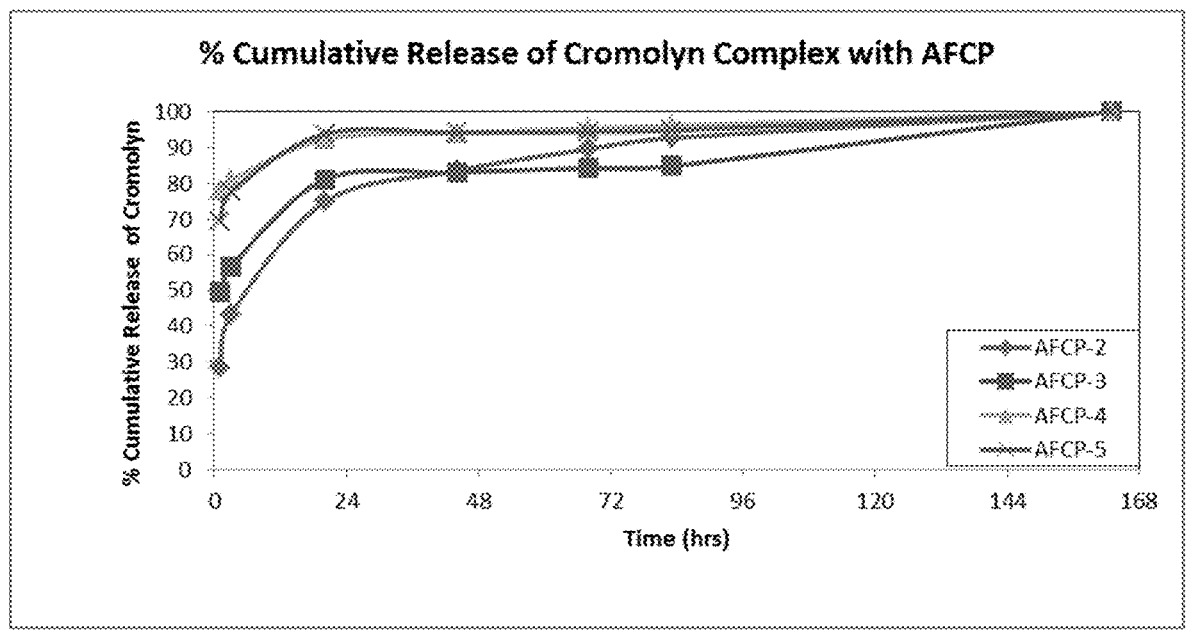
FIG. 23 is a graph showing the dissolution of cromolyn from various amine functionalized polymer complexes.
Figure 24:
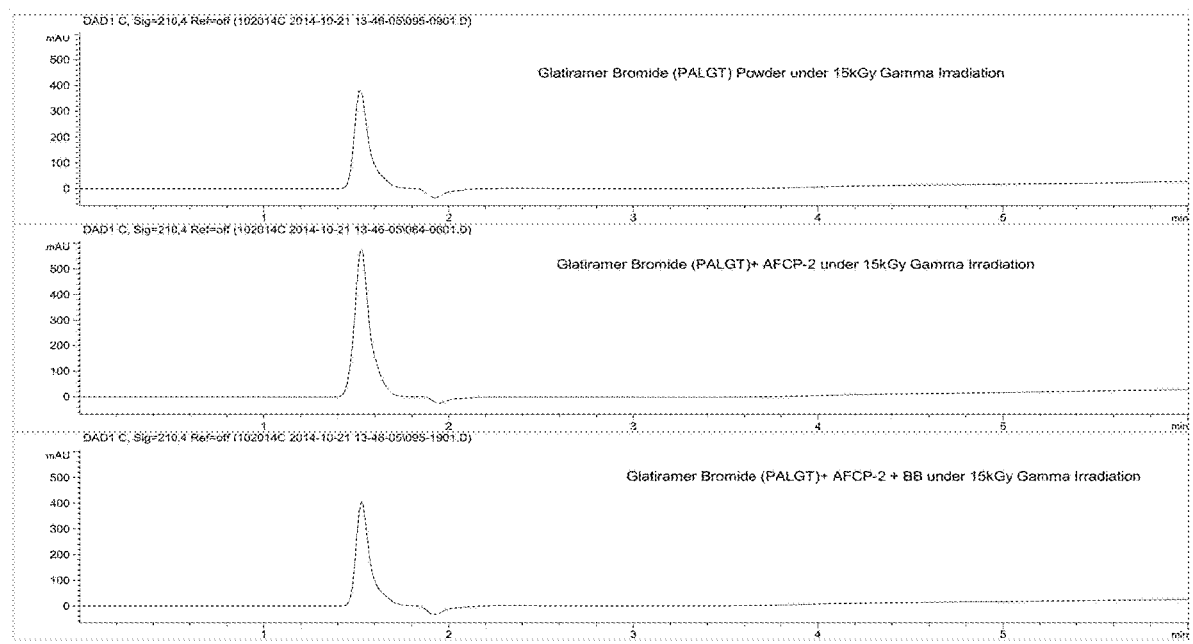
FIG. 24 provides reverse phase high pressure liquid chromatography (RPLC) spectra showing the stability of glatiramer bromide (uncomplexed powder—top, complexed with AFCP-2—middle, and complexed with AFCP-2 in benzyl benzoate (BB)—bottom) following gamma irradiation at a dose of 15 kGy.
Figure 25:
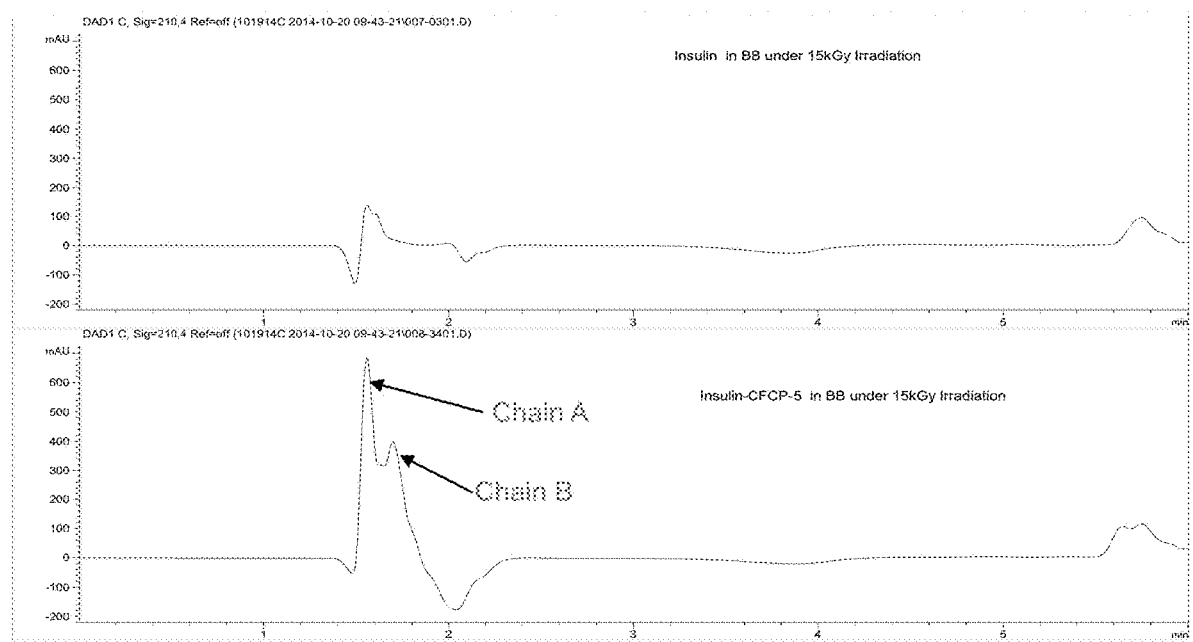
FIG. 25 provides RPLC spectra showing the stability of insulin (uncomplexed in BB—top and complexed with CFCP-5 in BB—bottom) following gamma irradiation at a dose of 15 kGy.
Figure 26:
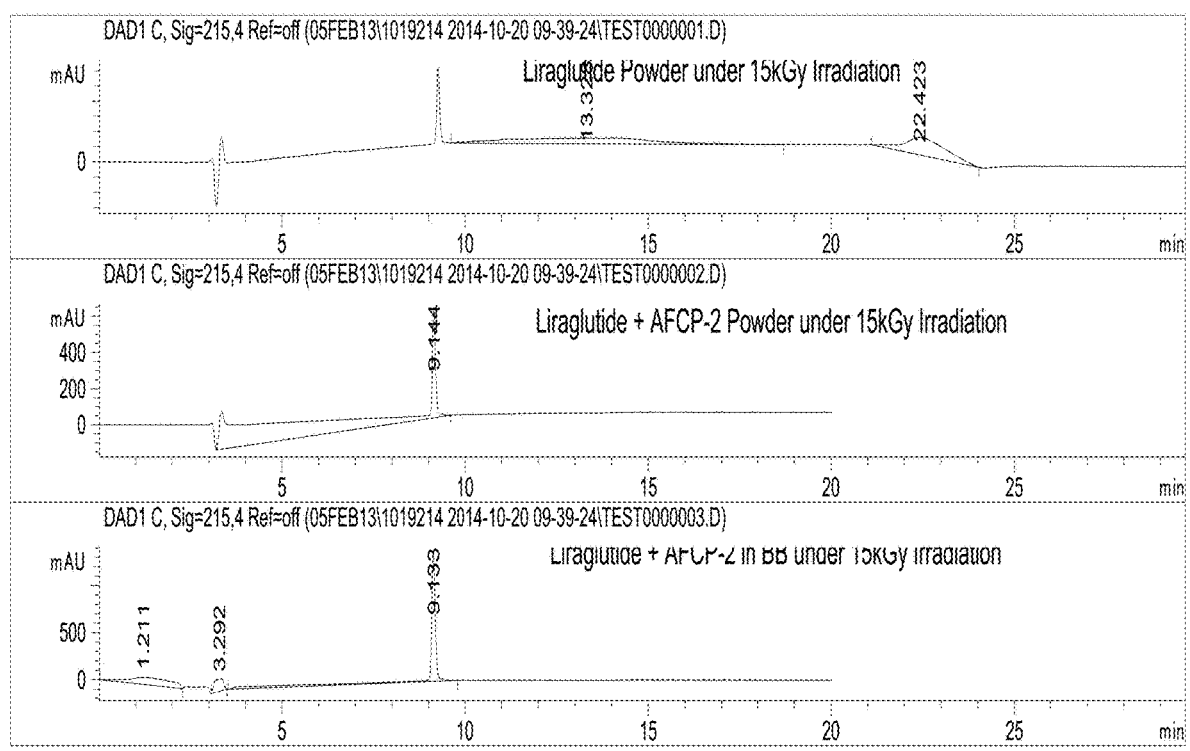
FIG. 26 provides RPLC spectra showing the stability of liraglutide (uncomplexed powder—top, complexed with AFCP-2—middle, and complexed with AFCP-2 in benzyl benzoate (BB)—bottom) following gamma irradiation at a dose of 15 kGy.
Figure 27:
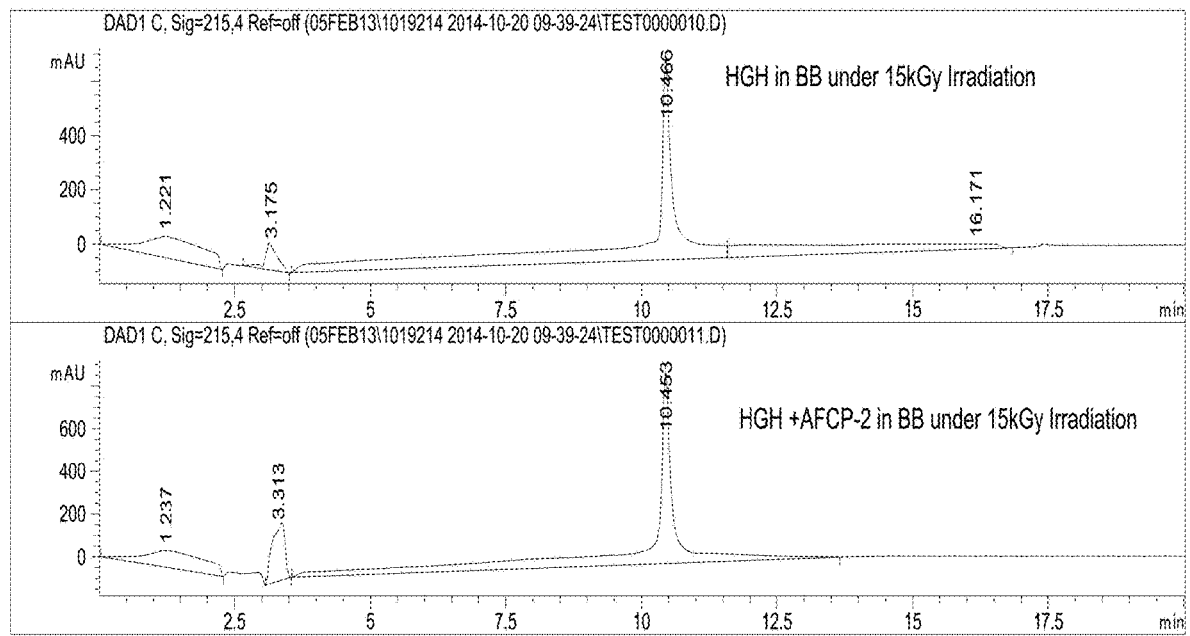
FIG. 27 provides RPLC spectra showing the stability of hGH (uncomplexed in BB—top and complexed with AFCP-2 in BB—bottom) following exposure to gamma irradiation at a dose of 15 kGy.

The results of the dissolution assays are shown in FIG. 23. Cromolyn complexed with AFCP2 dissolves in PBS at 37° C. at a slower rate than cromolyn complexed with the other AFCP complexes (30% initial release compared to 50-80%), which makes it a viable option for a depot administered on a weekly basis.

Example 28: Solubility of AFCP-2 and CFCP-1

Solubility of AFCP-2 and CFCP-1 copolymers in water at various pH values was determined.

Materials and Methods

~40 mg/mL of AFCP-2 or CFCP-1 in water was provided at room temperature and sonicated for 10 min. To the above solutions, either 0.05 N sodium Hydroxide solution or 0.05N Hydrochloric acid solution was added to increase or decrease the pH of the starting solutions as measured by Orion 3 Star pH Benchtop (Thermo Electron Corporation). The physical appearance was observed visually.

Results

The results of the above measurements are provided in Table 4 below.

TABLE 4

| AFCP-2 (40 mg/mL) | | CFCP-1 (40 mg/mL) | |
| --- | --- | --- | --- |
| pH | Physical Appearance | pH | Physical Appearance |
| 2.6 | Solution | 1.3 | Colloidal |
| 2.9 | Solution | 2.6 | Colloidal |
| 3.0 | Solution | 3.3 | Colloidal |
| 3.4 | Solution | 5.9 | Colloidal |
| 7.0 | Solution | 6.1 | Colloidal |
| 9.4 | Solution | 6.7 | Solution |
| 11.9 | Solution | 8.2 | Solution |
|  | Solution | 9.1 | Solution |

Example 29: Computational Toxicology Assessment

Degradation products for select amine and carboxylate functionalized polymers containing a 1,2,3 triazole were analyzed using Derek Nexus software in the Lhasa Knowledge Suite available from Lhasa Limited, Leeds, U.K. The Derek Nexus prediction includes an overall conclusion about the likelihood of toxicity in a structure and detailed reasoning information for the likelihood. The prediction is generated by applying expert knowledge rules in toxicology to the data returned from the certified Lhasa knowledge base.

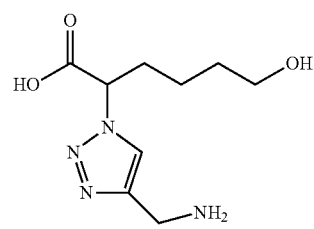

-continued

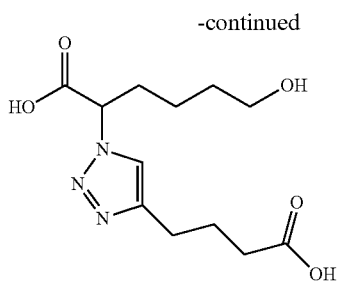

The above structures were analyzed using the Derek Nexus software, and no alerts for mutagenicity, genotoxicity, chromosomal damage or carcinogenicity were present in connection with the_1,2,3 triazole degradation products.

Example 30: Stability of AFCP and CFCP-complexed Active Agents Following Exposure to Gamma Radiation Glatiramer bromide, insulin, liraglutide, and human growth hormone (hGH) were complexed with AFCP-2, CFCP-5, AFCP-2, and AFCP-2 respectively and analyzed for stability following exposure to gamma radiation.

Materials and Methods

Active pharmaceutical ingredients (APIs) including Liraglutide (Bachem, >99% pure), Human Growth Hormone (HGH, Biosolutions, >95% pure), Poly (AGLT) Bromide (Sigma, >99% pure) and Insulin (Sigma, >95% pure) were obtained from their respective vendors and dissolved ammonium bicarbonate buffer (pH ~8) in appropriate concentrations. Amine-functionalized complexable polymer (AFCP-2) and carboxyl-functionalized complexable polymer (CFCP-5) were synthesized and dissolved in MilliQ water in appropriate concentrations (10-20 mg/mL). The APIs were mixed with the complexable polymers at a ratio of 1:1, 1:4 or 1:10. The instantaneous precipitation was separated from reaction media (ammonium bicarbonate in water) and dried via lyophilization. The dried powder or the dried powder suspended in Benzyl Benzoate were loaded either in glass vial or plastic syringes (Intervene) and packed in aluminum pouches. These samples were exposed to gamma radiation (12.5 kGy-17.5 kGy) for more than 8 hrs at room temperature with radiation indicator sticker (Sterigenics, Corona, Calif.). These gamma irradiated samples were then analyzed for purity using reverse phase liquid chromatography (RPLC) in reference to non-gamma irradiated samples.

Results

The results of the stability analyses are provided in FIGS. 24-27. The above active agents each showed good stability following exposure to 15 kGy gamma radiation as evidenced by the relative lack of degradants shown in the RPLC spectra. As seen in the Figures, non-complexed APIs such as Liraglutide, HGH, Poly(AGLT) bromide (Glatiramer bromide) and Insulin degraded faster (with a corresponding reduction in potency) after 15 kGy gamma irradiation. These APIs complexed either with AFCP or CFCP showed Gamma irradiation stability (15 kGy) as seen in FIGS. 24-27. RPLC spectra for the uncomplexed, non-irradiated APIs are provided in FIGS. 28 and 29.

The foregoing embodiments and advantages are merely exemplary and are not to be construed as limiting the present invention. The description of the present invention is intended to be illustrative, and not to limit the scope of the claims. Many alternatives, modifications, and variations will be apparent to those skilled in the art.

Having now fully described this invention, it will be understood to those of ordinary skill in the art that the methods of the present invention can be carried out with a wide and equivalent range of conditions, formulations, and other parameters without departing from the scope of the invention or any embodiments thereof.

Aspects, including embodiments, of the present subject matter described herein may be beneficial alone or in combination, with one or more other aspects or embodiments. Without limiting the foregoing or subsequent description, certain non-limiting aspects of the disclosure numbered 1-123 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below.

ASPECTS OF THE INVENTION

1. A complex comprising:
   a pharmaceutically active agent, and
   a functionalized polymer, the functionalized polymer comprising repeat units, the repeat units comprising ionizable repeat units comprising at least one ionizable side group, a plurality of the at least one ionizable side groups forming a plurality of non-covalent bonds with the pharmaceutically active agent,
   wherein at least 10% of the repeat units comprise at least one ionizable side group,
   wherein the functionalized polymer is optionally synthetic,
   wherein the functionalized polymer is optionally a polyester,
   wherein the functionalized polymer is optionally linear, and
   wherein the functionalized polymer optionally has a weight average molecular weight greater than 15,000 Daltons, as measured by gel permeation chromatography.
2. The complex of 1, wherein the at least one ionizable side group comprises at least one member selected from ammonium, carboxylate, hydrazinium, guanidinium, sulfate, sulfonate, phosphonate, and phosphate.
3. A complex comprising:
   a pharmaceutically active agent; and
   a functionalized polymer, the functionalized polymer comprising repeat units, the functionalized polymer comprising at least one of: (a) ionizable repeat units comprising at least one ionizable side group, wherein the at least one ionizable side group comprises at least one member selected from ammonium, carboxylate, hydrazinium, guanidinium, sulfate, sulfonate, phosphonate, and phosphate; and (b) at least one ionizable end group;
   wherein a plurality of the at least one ionizable groups form a plurality of non-covalent bonds with the pharmaceutically active agent,
   wherein the functionalized polymer is optionally synthetic,
   wherein the functionalized polymer is optionally a polyester,
   wherein the functionalized polymer is optionally linear, and wherein the functionalized polymer optionally has a weight average molecular weight greater than 15,000 Daltons, as measured by gel permeation chromatography.

4. The complex of 3, wherein at least 10% of the repeat units comprise at least one ionizable side group.

5. The complex of any one of 1-4, wherein at least 20% of the repeat units comprise at least one ionizable side group.

6. The complex of any one of 1-5, wherein at least 40% of the repeat units comprise at least one ionizable side group.

7. The complex of any one of 1-6, wherein less than 100% of the repeat units comprise at least one ionizable side group.

8. The complex of any one of 1-4, wherein the percentage of the repeat units comprising at least one ionizable side group ranges from 10% to 90%.

9. The complex of any one of 1-4, wherein the percentage of the repeat units comprising at least one ionizable side group ranges from 20% to 80%.

10. The complex of any one of 1-9, wherein the at least one ionizable side group is covalently bound to the polymer through click chemistry.

11. The complex of any one of 1-10, wherein the at least one ionizable side group is covalently bound to the polymer through click chemistry catalyzed with copper.

12. The complex of any one of 1-11, wherein the non-covalent bonds comprise electrostatic interactions.

13. The complex of any one of 1-11, wherein the non-covalent bonds comprise steric interactions.

14. The complex of any one of 1-11, wherein the non-covalent bonds comprise hydrogen bonding.

15. The complex of any one of 1-11, wherein the non-covalent bonds comprise van der Waals forces.

16. The complex of any one of 1-15, wherein the complex is a salt.

17. The complex of any one of 1-16, wherein the pharmaceutically active agent comprises at least one member selected from a peptide, protein, and small molecule, the small molecule having a molecular weight less than 500 Daltons.

18. The complex of any one of 1-17, wherein the at least one ionizable side group comprises a positively ionizable side group.

19. The complex of any one of 1-17, wherein the functionalized polymer has a net positive charge.

20. The complex of any one of 1-17, wherein the at least one ionizable side group comprises a negatively ionizable side group.

21. The complex of any one of 1-17, wherein the functionalized polymer has a net negative charge.

22. The complex of any one of 1-21, wherein the repeat units comprise repeat units comprising at least one pendant hydrophilicity modifier.

23. The complex of 22, wherein the at least one pendant hydrophilicity modifier is selected from polyethyleneglycol (PEG), hydroxyl and hydroxyalkyl.

24. The complex of any one of 1-23, wherein the functionalized polymer has a weight average molecular weight ranging from 1000 Daltons to 200,000 Daltons, as measured by gel permeation chromatography.

25. The complex of any one of 1-24, wherein the functionalized polymer has a weight average molecular weight ranging from 2000 Daltons to 50,000 Daltons, as measured by gel permeation chromatography.

26. The complex of any one of 1-25, wherein the functionalized polymer has a number average molecular weight ranging from 5000 Daltons to 45,000 Daltons, as measured by NMR spectroscopy.

27. The complex of any one of 1-26, wherein the functionalized polymer has a solubility in water of at least 0.01 mg/ml and less than or equal to 10 mg/ml at 25° C. and pH 7.4.

28. The complex of any one of 1-27, wherein the functionalized polymer is biodegradable.

29. The complex of any one of 1-28, wherein the complex has a solubility of less than 0.01 mg/mL in water at 25° C. at pH 7.4.

30. The complex of any one of 1-29, wherein the ratio of the amount of the pharmaceutically active agent to the amount of the functionalized polymer in the complex is from 1:1 to 1:10 by weight.

31. The complex of any one of 1-30, wherein the functionalized polymer comprises at least one ionizable end group comprising at least one member selected from ammonium, carboxylate, hydrazinium, guanidinium, sulfate, sulfonate, and phosphate.

32. The complex of any one of 1-31, wherein the ionizable repeat units comprise one or more ionizable side groups that comprise an optionally substituted heteroarylene ring.

33. The complex of 32, wherein the optionally substituted heteroarylene ring is a 1,2,3-triazole ring.

34. The complex of any one of 1-33, wherein the functionalized polymer is a polyester.

35. The complex any one of 1-34, wherein the repeat units comprise repeat units of the formula (I):

$$\left[ \begin{matrix} O \\ \parallel \\ C \end{matrix} \left( \begin{matrix} \\ R^1 \ R^2 \end{matrix} \right)_m O \right]$$ (I)

wherein
m is an integer from 1 to 10, and
each $R^1$ and $R^2$ is independently selected from hydrogen, hydroxyl, optionally substituted alkyl, optionally substituted alkenyl, optionally substituted alkynyl, optionally substituted alkoxy, optionally substituted carbocyclyl, optionally substituted aryl, optionally substituted heterocyclyl, optionally substituted heteroaryl, and a ionizable side group.

36. The complex of 35, wherein the repeat units comprise repeat units of the formula (I) wherein each $R^1$ and $R^2$ is independently selected from hydrogen, $C_{1-5}$ alkyl and a ionizable side group.

37. The complex of 35 or 36, wherein the repeat units comprise repeat units of the formula (I) wherein m is an integer from 1 to 5.

38. The complex of any one of 35-37, wherein the repeat units comprise repeat units of the formula (I) wherein one of the $R^1$s and $R^2$s is a ionizable side group and all of the remaining $R^1$s and $R^2$s are not ionizable side groups.

39. The complex of any one of 35-38, wherein the repeat units comprise repeat units of the formula (I) wherein m is 5, one $R^1$ is a ionizable side group and all of the remaining $R^1$s and $R^2$s are hydrogen.

40. The complex of any one of 35-39, wherein the ionizable side group comprises a positively charged side group.

41. The complex of any one of 35-39, wherein the ionizable side group comprises a negatively charged side group.

42. The complex of any one of 35-39, wherein the ionizable side group comprises ammonium, carboxylate, guanidinium, sulfate, or phosphate.
43. The complex of any one of 35-42, wherein the ionizable side group comprises an optionally substituted heteroarylene ring.
44. The complex of any one of 35-43, wherein the ionizable side group has the formula (II):

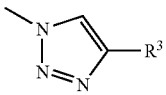

(II)

wherein $R^3$ comprises a ionizable functional group.
45. The complex of 44, wherein $R^3$ comprises at least one member selected from ammonium, carboxylate, guanidinium, sulfate and phosphate.
46. The complex of any one of 35-45, wherein the repeat units comprise repeat units of the formula (I) wherein m is 5 and all of the $R^1$ and $R^2$s are hydrogen.
47. The complex of any one of 35-46, wherein the repeat units comprise repeat units of the formula (I) wherein m is 1, $R^1$ is hydrogen and $R^2$ is hydrogen.
48. The complex of any one of 35-47, wherein the repeat units comprise repeat units of the formula (I) wherein m is 1, $R^1$ is methyl and $R^2$ is hydrogen.
49. The complex of any one of 35-48, wherein the repeat units comprise repeat units of the formula (I) wherein m is 2, the $R^1$ and $R^2$ alpha to the carbonyl group in formula (I) are each hydrogen, the $R^1$ beta to the carbonyl group is methyl and the $R^2$ beta to the carbonyl group is hydrogen.
50. The complex of any one of 35-49, wherein the repeat units comprise repeat units of the formula (I) wherein m is 3 and all of the $R^1$ and $R^2$s are hydrogen.
51. The complex of any one of 35-50, wherein the repeat units comprise repeat units of the formula (I) wherein m is 4, and all of the $R^1$ and $R^2$s are hydrogen.
52. The complex of any one of 35-51, wherein the repeat units comprise repeat units of the formula (I) wherein m is 3, the $R^1$ and $R^2$ alpha to the carbonyl group in formula (I) are each hydrogen, the $R^1$ and $R^2$ beta to the carbonyl group are each hydrogen, and the $R^1$ gamma to the carbonyl group is methyl and the $R^2$ gamma to the carbonyl group is hydrogen.
53. The complex of any one of 35-52, wherein the functionalized polymer is a homopolymer of repeat units of formula (I).
54. The complex of any one of 35-52, wherein the functionalized polymer is a copolymer comprising at least two different repeat units.
55. The complex of 54, wherein each of said at least two different repeat units is of formula (I).
56. A composition comprising:
a complex comprising:
a pharmaceutically active agent, and
a functionalized polymer complexed with the pharmaceutically active agent through non-covalent bonding; and
a vehicle,
wherein the functionalized polymer is optionally synthetic,
wherein the functionalized polymer is optionally a polyester,
wherein the functionalized polymer is optionally linear, and
wherein the functionalized polymer optionally has a weight average molecular weight ranging from 2000 Daltons to 20,000 Daltons, as measured by gel permeation chromatography.
57. The composition of 56, wherein the complex is a complex of any one of 1-55.
58. The composition of 56 or 57, wherein the amount of the functionalized polymer present in the composition is less than 50% by weight based on the total weight of the composition.
59. The composition of any one of 56-58, wherein the amount of the functionalized polymer present in the composition is less than 40% by weight based on the total weight of the composition.
60. The composition of any one of 56-59, wherein the amount of the functionalized polymer present in the composition is less than 30% by weight based on the total weight of the composition.
61. The composition of any one of 56-60, wherein the amount of the functionalized polymer present in the composition is less than 20% by weight based on the total weight of the composition.
62. The composition of any one of 56-61, wherein the amount of the functionalized polymer present in the composition is less than 10% by weight based on the total weight of the composition.
63. The composition of any one of 56-62, wherein the amount of the functionalized polymer present in the composition is less than 5% by weight based on the total weight of the composition.
64. The composition of 56 or 57, wherein the amount of the functionalized polymer present in the composition ranges from 1% by weight to 50% by weight based on the total weight of the composition.
65. The composition of 56 or 57, wherein the amount of the functionalized polymer present in the composition ranges from 5% by weight to 50% by weight based on the total weight of the composition.
66. The composition of 56 or 57, wherein the amount of the pharmaceutically active agent present in the composition ranges from 1% to 30% by weight based on the total weight of the composition.
67. The composition of any one of 56-66, wherein the vehicle comprises a vehicle polymer that is different from the functionalized polymer.
68. The composition of 67, wherein the vehicle polymer is present in the vehicle in an amount from about 5% to about 40% by weight of the vehicle.
69. The composition of any one of 56-68 or 120, wherein the vehicle comprises a solvent.
70. The composition of 69, wherein the solvent is present in an amount ranging from 60% to 100% by weight of the vehicle.
71. The composition of 69 or 70, wherein the solvent is a hydrophobic solvent.
72. The composition of 69 or 70, wherein the solvent is a hydrophilic solvent.
73. The composition of 69 or 70, wherein the solvent comprises at least one member selected from water, buffered aqueous system, dimethylsulfoxide (DMSO), benzyl alcohol (BA), benzyl benzoate (BB), hydrogenated castor oil, polyethoxylated castor oil, dimethylacetamide, ethanol, ethyl acetate, glycofurol, isopropyl myristate, ethyl benzoate, caprylic/capric triglyceride, n-methyl-pyrrolidone, propylene glycol monocaprylate, propylene carbonate, diethyl carbonate, 2-pyrrolidone, triacetin, and triethyl citrate.

74. The composition of 69 or 70, wherein the solvent comprises water.

75. The composition of any one of 56-68, wherein the vehicle comprises a buffered aqueous system.

76. The composition of 75, wherein the buffered aqueous system comprises at least one of phosphate buffered saline (PBS), ammonium bicarbonate, cresols, HPMC, ammonium acetate, sulfuric acid, and HCl.

77. The composition of any one of 56-76, comprising at least one member selected from sucrose acetate isobutyrate (SAIB), sucrose, mannitol, trehalose, surfactant, and antioxidant.

78. The composition of any one of 56-77, wherein the composition is free of other complexing agents.

79. The composition of any one of 56-78, wherein the composition is free of protamine and, optionally, wherein the composition is free of polymer other than the functionalized polymer.

80. The composition of any one of 56-79, wherein the composition is free of divalent metal ions.

81. The composition of any one of 56-80, wherein the composition is free of zinc.

82. The composition of any one of 56-81, wherein the composition is free of carboxymethylcellulose (CMC).

83. A method comprising:
providing a precursor polymer comprising repeat units, the repeat units comprising functionalizable repeat units comprising at least one functionalizable side group;
obtaining a functionalized polymer by transforming, using click chemistry, said functionalizable repeat units into ionizable repeat units comprising at least one ionizable side group; and
combining the functionalized polymer with a pharmaceutically active agent to form a complex in which a plurality of the at least one ionizable side groups form a plurality of non-covalent bonds with the pharmaceutically active agent.

84. The method of 83, 121 or 122, wherein the complex is a complex of any one of 1-55.

85. The method of 83 or 84, wherein said transforming, using click chemistry, comprises effecting a cycloaddition reaction.

86. The method of 85 wherein said cycloaddition reaction is a Diels-Alder cycloaddition reaction.

87. The method of 85, wherein said cycloaddition reaction is a Huisgen 1,3-dipolar cycloaddition reaction.

88. The method of 85, wherein said cycloaddition reaction is a cycloaddition reaction between an azide and an alkyne to form a linkage comprising a 1,2,3-triazole.

89. The method of any one of 83 to 88, wherein the functionalizable side group is an azido group and wherein the transforming, using click chemistry, comprises reacting the precursor polymer with an alkyne to form the functionalized polymer, the functionalized polymer comprising at least one 1,2,3-triazole ring.

90. The method of any one of 83 to 88, wherein the functionalizable side group is a leaving group and wherein the transforming, using click chemistry, comprises: (a) transforming the leaving group into an azido group and thereby providing a polymer intermediate; and (b) reacting the polymer intermediate with an alkyne to form the functionalized polymer, the functionalized polymer comprising at least one 1,2,3-triazole ring.

91. The method of 90, wherein the leaving group is a halogen group.

92. The method of 90 or 91, wherein the leaving group is transformed into an azido group by reacting the precursor polymer with sodium azide.

93. The method of any one of 89-92, wherein the alkyne is a terminal alkyne.

94. The method of any one of 83 to 88, wherein the functionalizable side group is an alkynyl group and wherein the transforming, using click chemistry, comprises reacting the precursor polymer with an azide to form the functionalized polymer, the functionalized polymer comprising at least one 1,2,3-triazole ring.

95. The method of 94, wherein the alkynyl group is a terminal alkynyl group.

96. The method of any one of 83-95, wherein the transforming, using click chemistry, comprises a monovalent copper catalyzed reaction or a ruthenium catalyzed reaction.

97. The method of 96, wherein the transforming, using click chemistry, comprises a monovalent copper catalyzed reaction, and wherein a monovalent copper catalyst is provided in the reaction through the ionization of copper iodide or copper bromide.

98. The method of any one of 83-97, wherein the transforming, using click chemistry, comprises a copper catalyzed azide-alkyne cycloaddition reaction.

99. The method of any one of 83-98, wherein the transforming, using click chemistry, comprises occurs at least partially under degassing conditions.

100. The method of any one of 83-99, wherein the combining occurs at a temperature ranging from 10° C. to 40° C.

101. The method of any one of 83-99, wherein the precursor polymer comprises repeat units of the formula (I'):

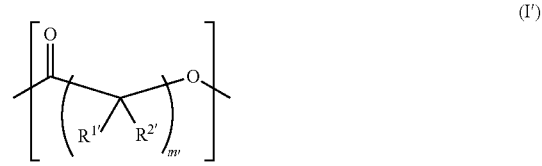

wherein
m' is an integer from 1 to 10, and
each $R^{1'}$ and $R^{2'}$ is independently selected from hydrogen, hydroxyl, optionally substituted alkyl, optionally substituted alkenyl, optionally substituted alkynyl, optionally substituted alkoxy, optionally substituted carbocyclyl, optionally substituted aryl, optionally substituted heterocyclyl, optionally substituted heteroaryl, a ionizable side group, and a functionalizable side group.

102. The method of 101, wherein the precursor polymer comprises functionalizable repeat units of the formula (I') wherein at least one of the $R^{1'}$'s and $R^{2'}$'s is a functionalizable side group.

103. The method of 101 or 102, wherein the precursor polymer comprises repeat units of the formula (I') wherein each $R^{1'}$ and $R^{2'}$ is independently selected from hydrogen, $C_{1-5}$ alkyl and a functionalizable side group.

104. The method of any one of 101-103, wherein the precursor polymer comprises repeat units of the formula (I') wherein m' is an integer from 1 to 5.

105. The method of any one of 101-104, wherein the precursor polymer comprises repeat units of the formula (I') wherein one of the $R^{1'}$'s and $R^{2'}$'s is a functionalizable side group and all of the remaining $R^{1'}$'s and $R^{2'}$'s are not functionalizable side groups.

106. The method of any one of 101-105, wherein the precursor polymer comprises repeat units of the formula (I') wherein m' is 5, one $R^{1'}$ is a functionalizable side group and all of the remaining $R^{1'}$'s and $R^{2'}$'s are hydrogen.
107. The method of any one of 101-106, wherein the precursor polymer comprises repeat units of the formula (I') wherein m' is 5 and all of the $R^{1'}$'s and $R^{2'}$'s are hydrogen.
108. The method of any one of 101-107, wherein the precursor polymer comprises repeat units of the formula (I') wherein m' is 1, $R^{1'}$ is hydrogen and $R^{2'}$ is hydrogen.
109. The method of any one of 101-108, wherein the precursor polymer comprises repeat units of the formula (I') wherein m' is 1, $R^{1'}$ is methyl and $R^{2'}$ is hydrogen.
110. The method of any one of 101-109, wherein the precursor polymer comprises repeat units of the formula (I') wherein m' is 2, the $R^{1'}$ and $R^{2'}$ alpha to the carbonyl group in formula (I') are each hydrogen, the $R^{1'}$ beta to the carbonyl group is methyl and the $R^{2'}$ beta to the carbonyl group is hydrogen.
111. The method of any one of 101-110, wherein the repeat units comprise repeat units of the formula (I') wherein m is 3 and all of the $R^{1'}$'s and $R^{2'}$'s are hydrogen.
112. The method of any one of 101-111, wherein the precursor polymer comprises repeat units of the formula (I') wherein m' is 4, and all of the $R^{1'}$'s and $R^{2'}$'s are hydrogen.
113. The method of any one of 101-112, wherein the repeat units comprise repeat units of the formula (I') wherein m is 3, the $R^{1'}$ and $R^{2'}$ alpha to the carbonyl group in formula (I') are each hydrogen, the $R^{1'}$ and $R^{2'}$ beta to the carbonyl group are each hydrogen, and the $R^{1'}$ gamma to the carbonyl group is methyl and the $R^{2'}$ gamma to the carbonyl group is hydrogen.
114. The method of any one of 101-113, wherein the functionalizable group is selected from a leaving group, an azido group or an alkynyl group.
115. The method of any one of 101-114, wherein the precursor polymer is a homopolymer of repeat units of formula (I') wherein at least one of the $R^{1'}$'s and $R^{2'}$'s is a functionalizable side group.
116. The method of any one of 101-114, wherein the precursor polymer is a copolymer comprising at least two different repeat units.
117. The method of 116, wherein each of said at least two different repeat units is of formula (I') and wherein at least one of said at least two different repeat units has a formula (I') in which at least one of the $R^{1'}$'s and $R^{2'}$'s is a functionalizable side group.
118. A complex as defined in any one of 1-55 for use as a medicament.
119. A composition as defined in any one of 56-82 for use as a medicament.
120. The composition of 67 or 68, wherein the vehicle polymer is a biodegradable polymer.
121. A method comprising:
   combining a functionalized polymer with a pharmaceutically active agent, the functionalized polymer comprising ionizable repeat units comprising at least one ionizable side group, to form a complex in which a plurality of the at least one ionizable side groups form a plurality of non-covalent bonds with the pharmaceutically active agent.
122. The method of 121, comprising preparing the functionalized polymer from a precursor polymer, the precursor polymer comprising repeat units, the repeat units comprising functionalizable repeat units comprising at least one functionalizable side group, wherein the preparing comprises transforming, using click chemistry, said functionalizable repeat units into ionizable repeat units comprising at least one ionizable side group.
123. The complex of any one of 1-55, wherein the functionalized polymer is not a polyamino acid.

What is claimed is:
1. A complex comprising:
   a pharmaceutically active agent, and
   a functionalized polymer, the functionalized polymer comprising repeat units, the repeat units comprising ionizable repeat units comprising at least one ionizable side group, a plurality of the at least one ionizable side groups forming a plurality of non-covalent bonds with the pharmaceutically active agent,
   wherein at least 10% of the repeat units comprise at least one ionizable side group, and
   wherein the ionizable repeat units comprise one or more ionizable side groups that comprise (1) an optionally substituted heteroarylene ring that is a 1,2,3-triazole ring and (2) at least one member selected from ammonium, carboxylate, hydrazinium, guanidinium, sulfate, sulfonate, phosphonate, and phosphate.
2. The complex of claim 1, wherein the percentage of the repeat units comprising at least one ionizable side group ranges from 20% to 80%.
3. The complex of claim 1, wherein the functionalized polymer is synthetic.
4. The complex of claim 1, wherein the functionalized polymer is a polyester.
5. The complex of claim 1, wherein the at least one ionizable side group is covalently bound to the polymer through click chemistry.
6. The complex of claim 1, wherein the plurality of non-covalent bonds comprise electrostatic interactions.
7. The complex of claim 1, wherein the pharmaceutically active agent comprises at least one member selected from a peptide, protein, and small molecule, the small molecule having a molecular weight less than 500 Daltons.
8. The complex of claim 1, wherein the at least one ionizable side group comprises a negatively ionizable side group.
9. The complex of claim 1, wherein the functionalized polymer has a weight average molecular weight ranging from 1000 Daltons to 200,000 Daltons, as measured by gel permeation chromatography.
10. The complex of claim 1, wherein the functionalized polymer has a solubility in water of at least 0.01 mg/ml and less than or equal to 10 mg/ml at 25° C. and pH 7.4.
11. The complex of claim 1, wherein the complex has a solubility of less than 0.01 mg/mL in water at 25° C. at pH 7.4.
12. The complex of claim 1, wherein the ratio of the amount of the pharmaceutically active agent to the amount of the functionalized polymer in the complex is from 1:1 to 1:10 by weight.
13. The complex of claim 1, wherein the functionalized polymer is not a polyamino acid.
14. The complex of claim 1, wherein the functionalized polymer is linear.
15. The complex of claim 1, wherein the functionalized polymer has a weight average molecular weight greater than 15,000 Daltons, as measured by gel permeation chromatography.

16. The complex of claim 1, wherein at least 40% of the repeat units comprise at least one ionizable side group.

* * * * *